United States Patent
Ahlem et al.

[11] Patent Number: 6,156,884
[45] Date of Patent: Dec. 5, 2000

[54] BIFUNCTIONAL BORONIC COMPOUND COMPLEXING REAGENTS AND COMPLEXES

[75] Inventors: Clarence N. Ahlem, La Jolla, Calif.; Robert J. Kaiser, Bothell, Wash.; Kevin P. Lund, Lynnwood, Wash.; Mark L. Stolowitz, Woodinville, Wash.

[73] Assignee: Prolinx, Inc., Bothell, Wash.

[21] Appl. No.: 09/222,468

[22] Filed: Dec. 29, 1998

Related U.S. Application Data

[60] Continuation-in-part of application No. 08/956,196, Oct. 22, 1997, Pat. No. 5,877,297, which is a division of application No. 08/691,930, Aug. 5, 1996, Pat. No. 5,777,148, and a continuation-in-part of application No. 08/956,194, Oct. 22, 1997, Pat. No. 5,872,224, which is a division of application No. 08/689,283, Aug. 5, 1996, Pat. No. 5,837,878.

[51] Int. Cl.$^7$ ............................................. C07F 5/04
[52] U.S. Cl. .............. 530/391.1; 530/345; 530/350; 530/402; 558/289; 558/298; 560/42; 562/622
[58] Field of Search .................... 558/289, 298; 560/42; 562/622; 530/391.1, 345, 350, 402

[56] References Cited

U.S. PATENT DOCUMENTS

| | | | |
|---|---|---|---|
| 2,548,257 | 7/1948 | Goldberg et al. | 562/453 |
| 4,269,605 | 5/1981 | Dean | 436/67 |
| 4,281,181 | 7/1981 | Nagasawa et al. | 562/453 |
| 4,496,722 | 1/1985 | Gallop et al. | 544/69 |
| 4,713,346 | 12/1987 | Gallop et al. | 436/86 |
| 4,783,487 | 11/1988 | Brune | 514/563 |
| 4,851,443 | 7/1989 | Brune | 514/563 |
| 4,894,229 | 1/1990 | Polson et al. | 424/92 |
| 4,910,300 | 3/1990 | Urdea et al. | 536/287 |
| 5,002,883 | 3/1991 | Bieniarz et al. | 435/176 |
| 5,045,451 | 9/1991 | Uhr et al. | 435/6 |
| 5,093,232 | 3/1992 | Urdea et al. | 435/7.23 |
| 5,183,653 | 2/1993 | Linder et al. | 424/1.1 |
| 5,464,861 | 11/1995 | Dobrusin et al. | 514/414 |

FOREIGN PATENT DOCUMENTS

| | | |
|---|---|---|
| 9013818 | 11/1990 | WIPO . |
| 9208722 | 5/1992 | WIPO . |
| 9420858 | 9/1994 | WIPO . |

Primary Examiner—Richard L. Raymond
Attorney, Agent, or Firm—Blakely, Sokoloff, Taylor & Zafman

[57] ABSTRACT

Reagents suitable for the modification of a bioactive species for the purpose of incorporating a bifunctional boronic compound complexing moiety for subsequent conjugation to a different (or the same) bioactive species having pendant phenylboronic acid moieties of General Formula 1, General Formula I

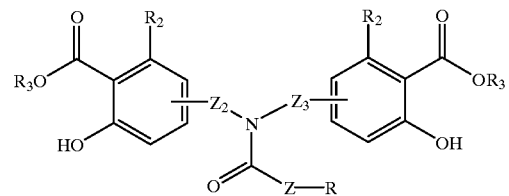

wherein group R is an electrophilic or nucleophilic moiety suitable for reaction of the putative bifunctional boronic compound complexing reagent with a bioactive species, wherein group $R_2$ is selected from one of H and OH moieties, and wherein group $R_3$ is selected from one of an alkyl and a methylene bearing an electronegative substituent. Group Z is a spacer selected from $(CH_2)_n$ and $CH_2O(CH_2CH_2O)_{n_2}$, wherein n is an integer of from 1 to 5, and wherein $n_2$ is an integer of from 1 to 4. Each of group $Z_2$ and $Z_3$ is a spacer selected from $CH_2Ar$, $CH_2CONHCH_2Ar$, $CH_2CONH(CH_2)_{n_3}CO$—$NHCH_2Ar$, and $(CH_2)_{n_4}NHCO(CH_2)_{n_5}CONHCH_2Ar$, wherein the group Ar represents the aromatic ring in the reagent of General Formula I to which the spacer $Z_2$ or $Z_3$ is appended, wherein $n_3$ is an integer of from 1 to 5, wherein $n_4$ is an integer selected from one of 2 and 3, and wherein $n_5$ is an integer of from 1 to 4. Reaction of a reagent of General Formula I with a bioactive species affords a conjugate having pendant putative bifunctional boronic compound complexing moieties. (one or more) The conjugate may be further reacted with hydroxylamine ($NH_2OH$) by amidation of the benzoic acid ester moiety to afford a class of bifunctional boronic compound complexing conjugate, e.g., conjugate with one or more pendant bifunctional boronic compound complexing moieties.

12 Claims, 11 Drawing Sheets

BIFUNCTIONAL BORONIC COMPOUND COMPLEXING REAGENTS AND COMPLEXES

CROSS-REFERENCE TO RELATED APPLICATIONS

This application is a continuation-in-part of U.S. patent application Ser. No. 08/956,196, filed Oct. 22, 1997, now U.S. Pat. No. 5,877,297, which is a divisional application of U.S. Pat. No. 5,777,148 (corresponding to Ser. No. 08/691,930, filed Aug. 5, 1996), and a continuation-in-part of U.S. patent application Ser. No. 08/956,194, filed Oct. 22, 1997, now U.S. Pat. No. 5,872,224 which is a divisional application of U.S. Pat. No. 5,837,878 (corresponding to Ser. No. 08/689,283, filed Aug. 5, 1996).

FIELD OF THE INVENTION

The present invention relates to the field of bioconjugate preparation, and more particularly, to a class of bifunctional boronic compound complexing reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormones, nucleic acids, liposomes and cells, with each other or with any other molecular species that add useful properties, including, but not limited to, drugs, radionuclides, toxins, haptens, inhibitors, chromophores, fluorophores, ligands, etc. Immobilization of biological macromolecules is also considered a special case of bioconjugation in which the macromolecule is conjugated, either reversibly or irreversibly, to an insoluble solid phase support. Bioconjugation is utilized extensively in biochemical, immunochemical and molecuar biological research. Major applications of bioconjugation include; detection of gene probes, enzyme-linked immuno solid-phase assay, monoclonal antibody drug targeting and medical imaging.

Bioconjugates are generally classified as either direct or indirect conjugates. Direct conjugates encompass those in which two or more components are joined by direct covalent chemical linkages. Alternatively, indirect conjugates encompass those in which two or more components are joined via an intermediary complex involving a biological macromolecule. The system described herein is the first to enable the formation of indirect conjugates without dependence upon an intermediary biological macromolecule.

Avidin-Biotin System

Although numerous methods of indirect bioconjugate preparation have been described, a significant number of those reported in the literature have been prepared by exploiting the Avidin-Biotin system, in which, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin possess four Biotin binding sites of very high affinity ($K_a = 10^{15} M^{-1}$).

The Avidin-Biotin system has been utilized extensively for enzyme-linked immuno solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., (1990) *Methods in Enzymology*, 184).

Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

Digoxigenin Anti-Digoxigenin System

An alternative indirect bioconjugation system designed to overcome some of the limitations associated with the Avidin-Biotin system has recently been developed for the detection of gene probes by ELISA (Kessler, C., Hoôtke, H.-J., Seibl, R., Burg, J. and Mühlegger, K., (1990) *Biol. Chem. Hoppe-Seyler*, 371, 917–965). This system involves the use of the steroid hapten Digoxigenin, an alkaloid occuring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the non-specific binding observed in Avidin-Biotin systems. Digoxigenin-labeled DNA and RNA probes can detect single-copy sequences in human genomic Southern blots. The development of the Digoxigenin anti-Digoxigenin system has recently been reviewed (Kessler, C. (1990) in Advances in Mutagenesis Research (Obe, G. ed.) pp. 105–152, Springer-Verlag, Berlin/Heidelberg). The Digoxigenin anti-Digoxigenin system is the most recent representative of several hapten-antibody systems now utilized extensively for bioconjugation.

Immobilized Phenylboronates

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or phenylboronate anion. Consequently, immobilized phenylboronic acids have been exploited as chromatographic supports to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in several reviews (Singhal, R. P. and DeSilva, S. S. M. (1992) *Adv. Chromatog.*, 31, 293–335; Mazzeo, J. R. and Krull, I. S. (1989) *BioChromatog.*, 4, 124–130; and Bergold, A. and Scouten, W. H. (1983) in Solid Phase Biochemistry (Scouten, W. H. ed.) pp. 149–187, John Wiley & Sons, New York).

Phenylboronic acid, like boric acid, is a Lewis acid, and ionizes not by direct deprotonation, but by hydration to give the tetrahedral phenylboronate anion ($pK_a$=8.86). Phenylboronic acid is three times as strong an acid as boric acid. Ionization of phenylboronic acid is an important factor in complex formation, in that, upon ionization, boron changes from trigonal coordination (having average bond angles of 120° and average bond lengths of 1.37 angstroms) to the tetrahedral coordinated anion (having average bond angles of 109° and average bond lengths of 1.48 angstroms).

Molecular species having cis or coaxial 1,2-diol and 1,3-diol functionalities, and particularly carbohydrates, are known to complex with immobilized phenylboronate anion, to form cyclic esters under alkaline aqueous conditions (Lorand, J. P. and Edwards, J. O. (1959) *J. Org. Chem.,* 24, 769).

Acidification of 1,2-diol and 1,3-diol complexes to neutral pH is know to release the diol containing species, presumably due to hydrolysis of the cyclic ester. Coplanar aromatic 1,3-diols, like 1,8-dihydroxynaphthalene, are known to complex even under acidic conditions due to the hydrolytic stability of six-membered cyclic boronic acid esters (Sienkiewicz, P. A. and Roberts, D. C. (1980) *J. Inorg. Nucl. Chem.,* 42, 1559–1571). Molecular species having pendant 1,2-hydroxylamine, 1,3-hydroxylamine, 1,2-hydroxyamide, 1,3-hydroxyamide, 1,2-hydroxy-oxime and 1,3-hydroxyoxime functionalities are also known to reversibly complex with phenylboronic acid under alkaline aqueous conditions similar to those associated with the retention of diol containing species (Tanner, D. W. and Bruice, T. C. (1967) *J. Amer. Chem. Soc.,* 89, 6954).

Phenylboronate Bioconjugates

Ortho-substituted acetamidophenylboronic acids have been proposed as potential linkers for selective bioconjugation via the vicinal diol moieties of the carbohydrate residues associated with glycoproteins (Cai, S. X. and Keana, J. F. W. (1991) *Bioconjugate Chem.,* 2, 317–322). Phenylboronic acid bioconjugates derived from 3-isothiocyanatophenylboronic acid have been successfully utilized for appending radioactive technetium dioxime complexes to monoclonal antibodies for use in medical imaging (Linder, K. E., Wen, M. D., Nowotnik, D. P., Malley, M. F., Gougoutas, J. Z., Nunn, A. D. and Eckelman, W. C. (1991) *Bioconjugate Chem.,* 2, 160–170; Linder, K. E., Wen, M. D., Nowotnik, D. P., Ramalingam, K., Sharkey, R. M., Yost, F., Narra, R. K. and Eckelman, W. C. (1991) *Bioconjugate Chem.,* 2, 407–414). 3-Aminophenylboronic acid has been covalently appended to proteins by a variety of chemical methods and the resulting phenylboronic acid bioconjugates tested for their binding of D-sorbitol, D-mannose and glycated hemoglobin (GHb). The interactions proved to be reversible and of very low affinity rendering the bioconjugates of very limited practical use. Similarly, an alkaline phosphatase phenylboronic acid bioconjugate used in an attempted enzyme-linked assay for the detection of GHb failed to detect the presence of glycated protein (Frantzen, F., Grimsrud, K., Heggli, D. and Sundrehagen, E. (1995) *Journal of Chromatography B,* 670, 37–45).

Phenylboronic Acid Complexing Reagents

A novel class of phenylboronic acid reagents and phenylboronic acid complexing reagents have been developed for conjugating biologically active species by exploiting indirect bioconjugation through a reversible boron complex. These reagents and associated conjugates may be used in a manner analogous to Avidin-Biotin and Digoxigenin-anti-Digoxigenin systems. However, unlike the Avidin-Biotin and Digoxigenin-anti-Digoxigenin systems, wherein the viability of the biological macromolecule must be maintained to preserve requisite binding properties, the bioconjugate formed through the boron complex is generally insensitive to significant variations in ionic strength, temperature, the presence of organic solvents, and the presence of chaotropic agents (protein denaturants).

Phenylboronic acid reagents, phenylboronic acid complexing reagents, their conjugates and bioconjugates, as well as methods for their preparation and use are the subject of U.S. Pat. Nos. 5,594,111, 5,623,055, 5,668,258, 5,648,470, 5,594,151, 5,668,257, 5,677,431, 5,688,928, 5,744,627, 5,777,148, 5,831,045, 5,831,046 and 5,837,878.

SUMMARY OF THE INVENTION

The present invention relates to a novel class of bifunctional boronic compound complexing reagents useful for the preparation of bioconjugates, and the method of making and using such reagents. In one embodiment, the boron compound is phenylboronic acid, or derivatives thereof, which complex with the complexing reagents of the present invention. In a second embodiment, the boron compound is phenyldiboronic acid, or derivatives thereof, which complex with the complexing reagents of the present invention. Unless otherwise noted, the phrase bifunctional boronic compound complexing reagent is used herein to include the broader class of boron compound complexing reagents which complex with boron compounds, and the phrase phenylboronic acid is used herein to include the broader class of boron compounds which complex with the boron compound complexing reagents, including bifunctional boronic compound complexing reagents. In the present invention, in the place of prior art Avidin-Biotin and Digoxigenin anti-Digoxigenin systems, bifunctional boronic compound complexing reagents comprised of two boron compound complexing moieties can be utilized in conjunction with the boron compound, such as phenylboronic acid reagents (many of which are known in the prior art) to facilitate chemical conjugation and prepare bioconjugates without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, solid-phase supports, and boron compound complexing reagents conjugates. These various components utilized in bioconjugate preparation will collectively and individually be termed biologically active species or bioactive species.

Two alternative methods for the preparation of bioconjugates derived from bifunctional boronic compound complexing reagents are disclosed below. In the first method, which is comprised of three steps, a reagent having putative boronic compound complexing moieties is first prepared, and then converted into a boronic compound complexing conjugate prior to reaction with a phenylboronic acid conjugate to afford a bioconjugate. In the second method, which is comprised of two steps, a boronic compound complexing conjugate is prepared in a single step, and then reacted with a phenylboronic acid conjugate to afford a bioconjugate.

THREE-STEP METHOD OF BIOCONJUGATE PREPARATION

Reagents suitable for the modification of a bioactive species for the purpose of incorporating a bifunctional boronic compound complexing moiety for subsequent conjugation to a different (or the same) bioactive species having pendant phenylboronic acid moieties are of General Formula I, General Formula I

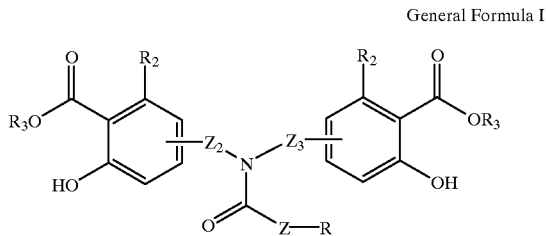

wherein group R is an electrophilic or nucleophilic moiety suitable for reaction of the putative bifunctional boronic compound complexing reagent with a bioactive species, wherein group $R_2$ is selected from one of H and OH moieties, and wherein group $R_3$ is selected from one of an alkyl (e.g., methyl, ethyl, etc.) and a methylene bearing an electronegative substituent.

Group Z is a spacer selected from $(CH_2)_n$ and $CH_2O(CH_2CH_2O)_{n_2}$, wherein n is an integer of from 1 to 5, and wherein $n_2$ is an integer of from 1 to 4. Each of group $Z_2$ and $Z_3$ is a spacer selected from $CH_2Ar$, $CH_2CONHCH_2Ar$, $CH_2CONH(CH_2)_{n_3}CO$—$NHCH_2Ar$, and $(CH_2)_{n_4}NHCO(CH_2)_{n_5}CONHCH_2Ar$, wherein the group Ar represents the aromatic ring in the reagent of General Formula I to which the spacer $Z_2$ or $Z_3$ is appended, wherein $n_3$ is an integer of from 1 to 5, wherein $n_4$ is an integer selected from one of 2 and 3, and wherein $n_5$ is an integer of from 1 to 4. It is to be appreciated that, for a given reagent of General Formula I, spacers $Z_2$ and $Z_3$ need not be the same moiety.

Reaction of a reagent of General Formula I with a bioactive species affords a conjugate having pendant putative bifunctional boronic compound complexing moieties (one or more) of General Formula II, General Formula II

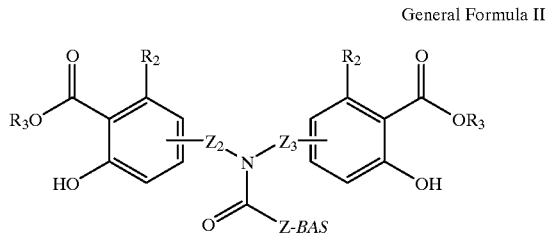

wherein groups $R_2$, $R_3$, Z, $Z_2$ and $Z_3$ are as were previously defined, and wherein the symbol labeled BAS represents a biologically active species (or bioactive species) that may or may not contain a portion of a reactive moiety (which may itself have a spacer) used to attach the bioactive species to the reagent.

It will be appreciated that, in many embodiments, several identical reagents of General Formula I will react with a single BAS molecule. For example, if the BAS is a protein, many bifunctional boronic compound complexing reagents will react with the protein, each reacting at one of the several sites on the protein which are reactive with the R group.

The conjugate of General Formula II may be further reacted with hydroxylamine ($NH_2OH$) by amidation of the benzoic acid ester moiety to afford a class of bifunctional boronic compound complexing conjugate, e.g., conjugate with one or more pendant bifunctional boronic compound complexing moieties of General Formula III,-

General Formula III

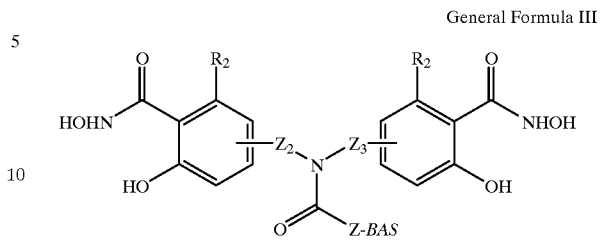

wherein groups $R_2$, Z, $Z_2$, $Z_3$ and BAS are as were previously defined.

Phenylboronic acid reagents, many of which are known in the prior art, as well as those described in greater detail in my copending application, titled "Phenyldiboronic Acid Reagents and Complexes", filed Aug. 21, 1998, Ser. No. 09/138,105, which is incorporated herein by reference, may be appended to a biologically active species to afford a conjugate having pendant phenylboronic acid moieties (one or more) of the general formula of General Formula IV, General Formula IV

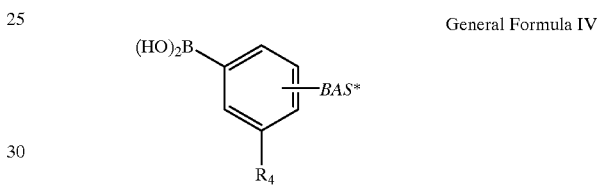

wherein group $R_4$ is selected form one of H and $B(OH)_2$ moieties, and wherein the symbol labeled BAS* represents a second bioactive species, that may include a linker portion and that may differ from the bioactive species labeled BAS. The BAS* may also include a portion of a reactive moiety used to attach the bioactive species to the phenylboronic acid reagent.

A conjugate of General Formula III, with at least one biologically active species and having pendent bifunctional boronic compound complexing moieties (one or more), may be complexed with a conjugate of General Formula IV, prepared from a second bioactive species BAS* and having pendant phenylboronic acid moieties (one or more), to afford a bioconjugate of General Formula V, General Formula V

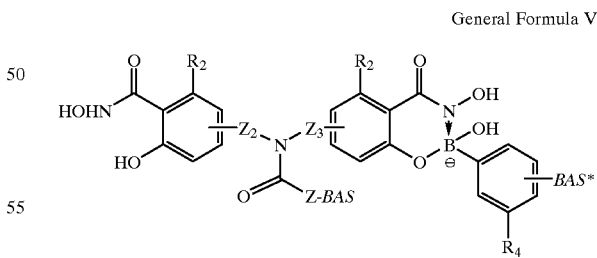

wherein the symbols labeled BAS and BAS*, and groups $R_2$, $R_4$, Z, $Z_2$ and $Z_3$, are as were previously defined. In this manner, biological macromolecules may be conjugated to one another or with other functionalities that impart useful properties.

Two-Step Method of Bioconjugate Preparation

Alternatively, a second class of reagents suitable for the modification of a bioactive species for the purpose of incorporating a bifunctional boronic compound complexing moiety for subsequent conjugation to a different (or the same) bioactive species having pendant phenylboronic acid moieties are of General Formula VI, General Formula VI

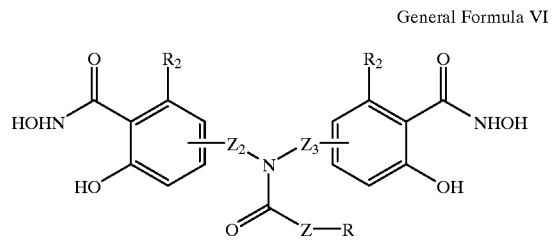

wherein group $R_1$ is a reactive electrophilic or nucleophilic moiety suitable for reaction of the putative bifunctional boronic compound complexing reagent with a bioactive species, and wherein group $R_2$ is selected from one of H and OH moieties. Group Z is a spacer selected from $(CH_2)_n$ and $CH_2O(CH_2CH_2O)_{n_2}$, wherein n is an integer of from 1 to 5, and wherein $n_2$ is an integer of from 1 to 4. Each of group $Z_2$ and group $Z_3$ is a spacer selected from $CH_2Ar$, $CH_2CONHCH_2Ar$, $CH_2CONH(CH_2)_{n_3}CONHCH_2Ar$, and $(CH_2)_{n_4}NHCO(CH_2)_{n_5}CONHCH_2Ar$, wherein the group Ar represents the aromatic ring in the reagent of General Formula VI to which the spacer $Z_2$ or $Z_3$ is appended, wherein $n_3$ is an integer of from 1 to 5, wherein $n_4$ is an integer selected from one of 2 and 3, and wherein $n_5$ is an integer of from 1 to 4. It is to be appreciated that, for a given reagent of General Formula VI, spacers $Z_2$ and $Z_3$ need not be the same moiety.

Reaction of a reagent of General Formula VI with a bioactive species affords a conjugate having pendant boronic compound complexing moieties (one or more) of General Formula VII, General Formula VII

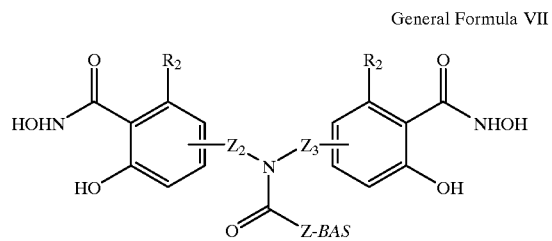

wherein groups $R_2$, Z, $Z_2$, and $Z_3$ are as were previously defined, and wherein the symbol BAS represents the bioactive species that may or may not contain a portion of a reactive moiety used to attach the bioactive species.

In a manner indistinguishable from that described above for the three-step method, a conjugate of General Formula VII (which is comparable to a conjugate of General Formula III), may be complexed with a conjugate of General Formula IV, to afford a bioconjugate of General Formula V, General Formula V

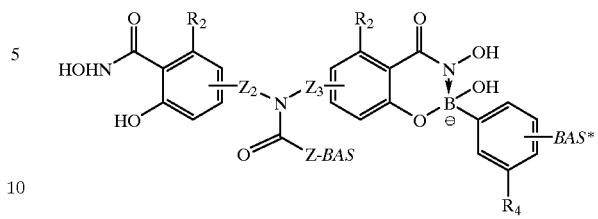

wherein the symbols labeled BAS and BAS*, and groups $R_2$, $R_4$, Z, $Z_2$ and $Z_3$ are as were previously defined. In this manner, biological macromolecules may be conjugated to one another or with other functionalities that impart useful properties.

Bioconjugates of General Formula V, whether formed, for example, in accordance with either the three-step method or the two-step method described above, may be prepared in buffered aqueous solution or organic solvents. The bioconjugate is formed within a few minutes over a range of temperatures from about 4° C. to 70° C. The stability of the bioconjugate in aqueous solution at a given pH and temperature is significantly influenced by substituent group $R_2$. Bioconjugates of General Formula V, wherein group $R_4$ is H, are stable in aqueous solutions of approximate pH greater than 3.5 and less than 12,5. Bioconjugates of General Formula V, wherein group $R_2$ is OH, are stable in aqueous solutions of approximate pH greater than 1.5 and less than 12.5.

DETAILED DESCRIPTION OF THE INVENTION

Figure 1:
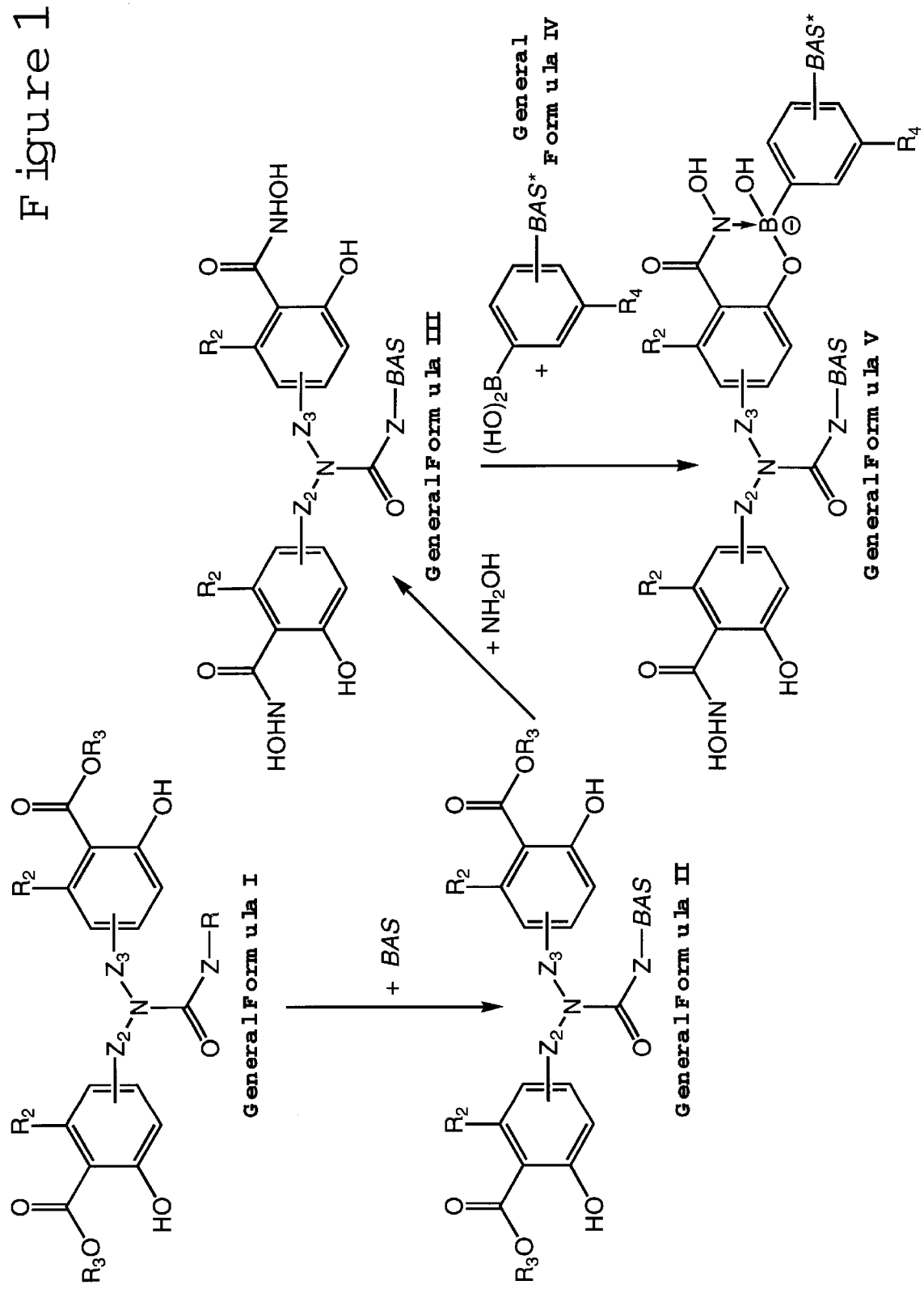
FIG. 1 illustrates the utilization of putative bifunctional boronic compound complexing reagents of General Formula I to prepare conjugates of General Formula III, which may, in turn, be utilized to prepare bioconjugates of General Formula V.

The three-step method which utilizes reagents of General Formula I for the preparation of bioconjugates is summarized in FIG. 1. Initially, a reagent of General Formula I is selected that is comprised of an appropriate electrophilic or nucleophilic group R suitable for reaction with the desired biologically active species.

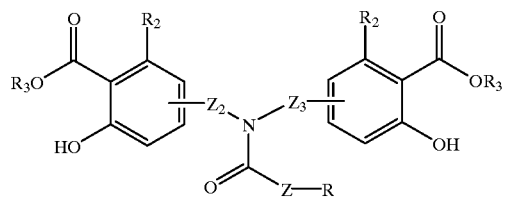

General Formula I

Group R is an electrophilic or nucleophilic moiety suitable for reaction of the putative bifunctional boronic compound complexing reagent with a bioactive species, and is preferably selected from, but not limited to, one of acrylamido, bromo, dithiopyridyl, bromoacetamido, chloro, chloroacetamido, hydrazido, N-hydroxysuccinimido ester, N-hydroxysulfosuccinimido ester, imido ester, imidazolido iodo, iodoacetamido, maleimido amino and thiol moieties.

Group R$_2$ is selected from one of H and OH moieties.

Group R$_3$ is selected from one of an alkyl (e.g., methyl, ethyl, etc.) and a methylene bearing an electronegative substituent. An electronegative substituent is a substituent with a negative dipole moment, e.g., CN, COOH, etc. Group R$_3$ is preferably selected from one of CH$_3$, CH$_2$CH$_3$, CH$_2$CN, CH$_2$COOH, CH$_2$CONH$_2$ and CH$_2$OCH$_3$.

Group Z is a spacer selected from one of (CH$_2$)$_n$ and CH$_2$O(CH$_2$CH$_2$O)$_{n_2}$, wherein n is an integer of from 1 to 5, and wherein n$_2$ is an integer of from 1 to 4.

Each of group Z$_2$ and group Z$_3$ is a spacer selected from one of CH$_2$Ar, CH$_2$CONHCH$_2$Ar, CH$_2$CONH(CH$_2$)$_{n_3}$CONHCH$_2$Ar and (CH$_2$)$_{n_4}$NHCO(CH$_2$)$_{n_5}$CO—NHCH$_2$Ar, wherein the group Ar represents the aromatic ring in the reagent of General Formula I to which the spacer Z$_2$ or Z$_3$ is appended, wherein n$_3$ is an integer of from 1 to 5, wherein n$_4$ is an integer selected from one of 2 and 3, and wherein n$_5$ is an integer of from 1 to 4. It is to be appreciated that, for a given reagent of General Formula I, spacers Z$_2$ and Z$_3$ need not be the same moiety.

The next step in a three-step method for the preparation of bioconjugates is to condense the appropriate reagent with the bioactive species to yield a conjugate of General Formula II,

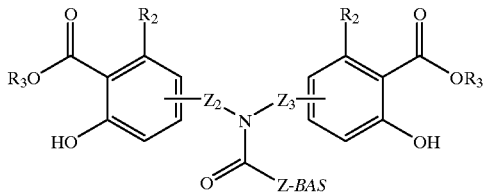

General Formula II wherein groups R$_2$, R$_3$, Z, Z$_2$ and Z$_3$ are as were previously defined, and wherein the symbol BAS represents a biologically active species which may or may not contain a portion of a reactive moiety used to attach the biologically active species to the reagent.

Next, the conjugate of the general formula of General Formula II is reacted with an excess of an aqueous solution of hydroxylamine to afford a conjugate of General Formula III, General Formula III

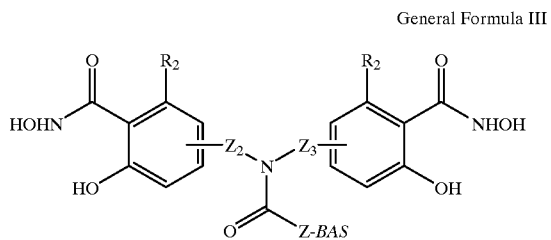

wherein groups Z, $Z_2$, $Z_3$, $R_2$ and BAS are as were previously defined.

Aqueous solutions of hydroxylamine ($NH_2OH$) suitable for use in the aforementioned reaction are in the concentration range 0.1 to 1 molar, and are prepared by addition of solid sodium hydroxide to an aqueous solution of hydroxylamine hydrochloride to obtain an approximate pH of 10. The reactivity of hydroxylamine toward the benzoate esters of General Formula II is determined by the choice of group $R_3$. When $R_3$ (in General Formula II) is an alkyl group, reaction overnight with 0.5 M hydroxylamine at room temperature may be required to insure complete conversion of the benzoate ester to the corresponding hydroxamic acid. However, when $R_3$ is a methylene group bearing an electronegative substituent, and is preferably the cyanomethyl group ($CH_2CN$), quantitative conversion of the benzoate ester to the corresponding hydroxamic acid is complete within 2 hours with 0.1 M hydroxylamine at 4° C.

The bifunctional boronic compound complexing conjugate of General Formula Ill is next complexed with a phenylboronic acid conjugate having the general formula of General Formula IV:

General Formula IV

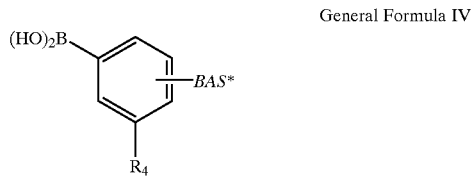

wherein group $R_4$ is selected from one of H and $B(OH)_2$ moieties, and wherein the symbol labeled BAS* represents a second biologically active species, that may include a linker portion and differ from the biologically active species labeled BAS of the complexing reagent. The BAS* may also include a portion of a reactive moiety used to attach the bioactive species to the phenylboronic acid reagent. The complexation reaction yields a bioconjugate of the general formula of General Formula V, General Formula V

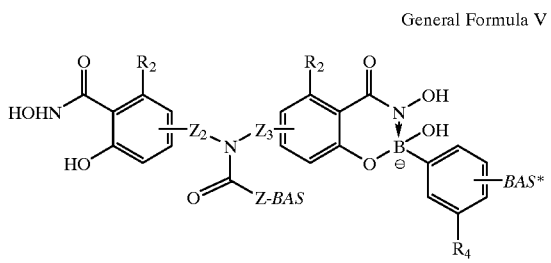

wherein groups Z, $Z_2$, $Z_3$, $R_2$, $R_4$, BAS and BAS* are as were previously defined.

Figure 2:
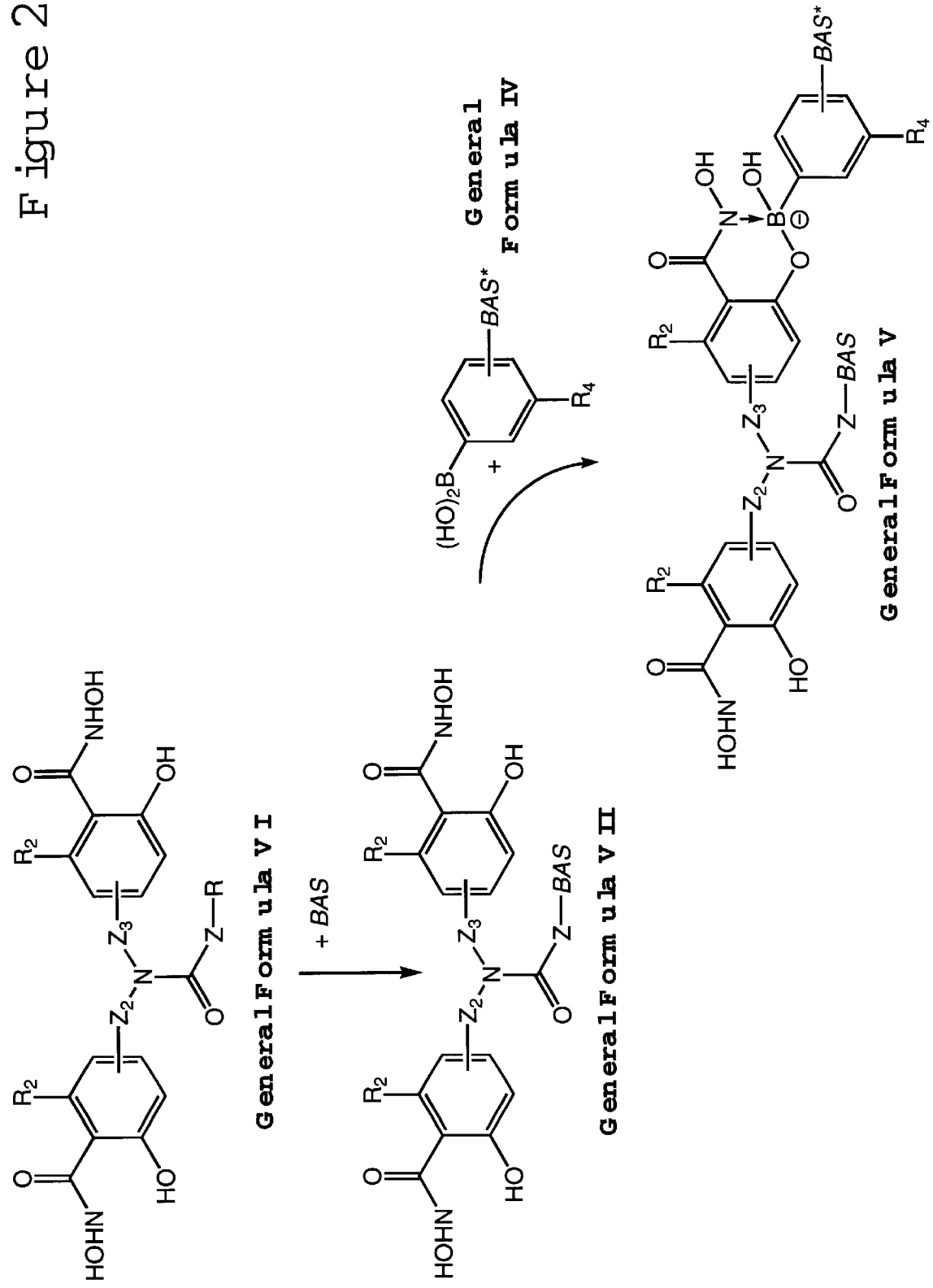
FIG. 2 illustrates the utilization of putative bifunctional boronic compound complexing reagents of General Formula VI to prepare conjugates of General Formula VII, which may, in turn, be utilized to prepare bioconjugates of General Formula V.

Alternatively, a two-step method which utilizes reagents of General Formula VI for the preparation of bioconjugates is summarized in FIG. 2. Initially, a reagent of General Formula VI is selected that is comprised of an appropriate reactive electrophilic or nucleophilic group $R_1$ suitable for reaction with the desired biologically active species.

General Formula VI

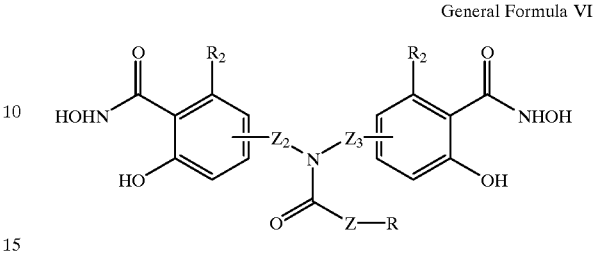

Group $R_1$ is an electrophilic or nucleophilic moiety suitable for reaction of the bifunctional boronic compound complexing reagent with a bioactive species. The presence of the hydroxamic acid moiety in general Formula VI may limit the potential scope of reactive electrophilic or nucleophilic moieties suitable for reaction of the reagent with a bioactive species, owing to the cross-reactivity known to occur between otherwise suitable moieties and the hydroxamic acid moiety. Consequently, in one embodiment group $R_1$ is preferably selected from, but not limited to, one of acrylamido, amino, dithiopyridyl, hydrazido, imidate ester, maleimido, and thiol moieties.

Group $R_2$ is selected from one of H and OH moieties.

Group Z is a spacer selected from one of $(CH_2)_n$ and $CH_2O(CH_2CH_2O)_{n_2}$, wherein n is an integer of from 1 to 5, and wherein $n_2$ is an integer of from 1 to 4.

Each of group $Z_2$ and group $Z_3$ is a spacer selected from one of $CH_2Ar$, $CH_2CONHCH_2Ar$, $CH_2CONH(CH_2)_{n_3}CONHCH_2Ar$ and $(CH_2)_{n_4}NHCO(CH_2)_{n_5}CO—NHCH_2Ar$, wherein the group Ar represents the aromatic ring in the reagent of General Formula VI to which the spacer $Z_2$ or $Z_3$ is appended, wherein $n_3$ is an integer of from 1 to 5, wherein $n_4$ is an integer selected from one of 2 and 3, and wherein $n_5$ is an integer of from 1 to 4.

The next step in a two-step process for the preparation of bioconjugates is to condense the appropriate reagent with the bioactive species to yield a conjugate of the general formula of General Formula VII, General Formula VII

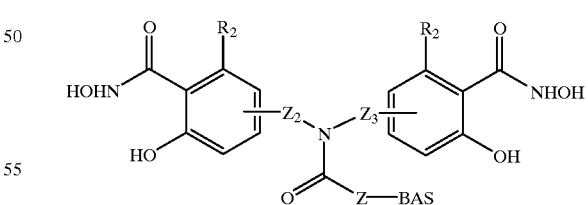

wherein groups $R_2$, Z, $Z_2$ and $Z_3$ are as were previously defined, and wherein the symbol labeled BAS represents a biologically active species which may or may not contain a portion of a reactive moiety used to attach the biologically active species to the reagent.

Finally, the boronic compound complexing conjugate of General Formula VII is complexed with a phenylboronic acid conjugate of General Formula IV to afford a bioconjugate of the general formula of General Formula V, General Formula V

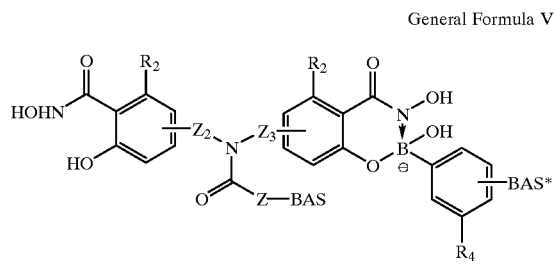

wherein group $R_4$ is selected from one of H and $B(OH)_2$ moieties. The symbol labeled BAS* represents a second biologically active species that may or may not contain a portion of a reactive moiety used to attach the biologically active species to the reagent. Groups $R_2$, Z, $Z_2$, $Z_3$, and BAS are as were previously defined.

Bioconjugates Comprised of Three Bioactive Species

Figure 3:
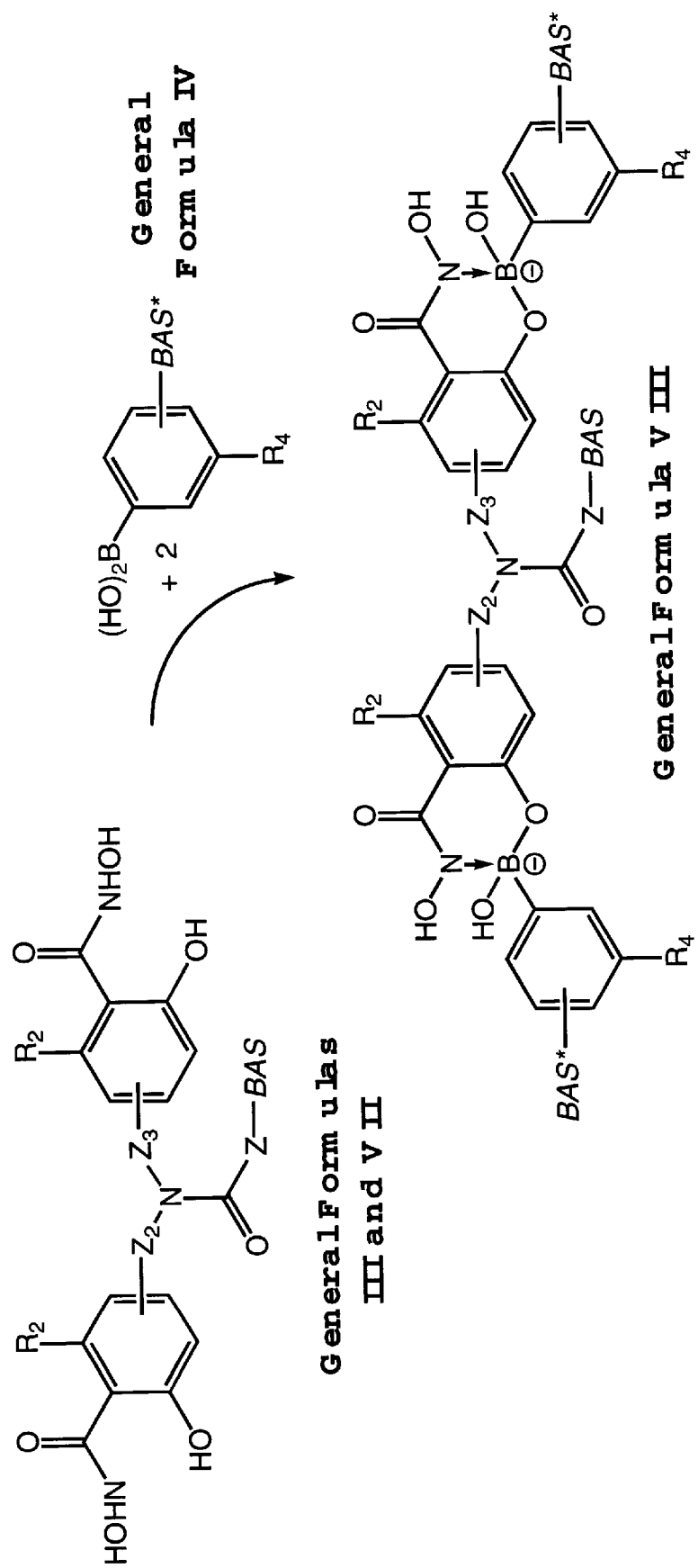
FIG. 3 illustrates the utilization of a bifunctional boronic compound complexing conjugate of either General Formula III or General Formula VII to prepare bioconjugates of General Formula VIII.

As illustrated in FIG. 3, the presence of two boronic compound complexing moieties in conjugates of General Formulas III and VII, enable the potential for the preparation of bioconjugates comprised of a single bifunctional boronic compound complexing conjugate and two phenylboronic acid conjugates of the general formula of General Formula VIII, formamide, which are incompatible with prior art indirect labeling systems wherein the structure of a biological macromolecule must be maintained to preserve requisite binding properties. Once formed, the bioconjugates are stable upon removal of water, and can be lyophilized for storage.

The stability of the bioconjugate in aqueous solutions at a given pH is determined to some extent by substituent group $R_2$. Phenylboronic acid complexes of General Formulas V and VIII, wherein group $R_2$ is H, are stable in buffered aqueous solutions over the approximate pH range 3.5 to 12.5. Phenylboronic acid complexes of General Formulas V and VIII, wherein group $R_2$ is OH, are stable in buffered aqueous solutions over the approximate pH range 1.5 to 12.5.

Synthesis of Reagents of General Formulas I and VI

Reagents of General Formulas I and VI are prepared from synthetic intermediates that are also utilized in the syntheses of the various monofunctional boronic acid complexing reagents which are described in U.S. Pat. Nos. 5,777,148, 5,744,627, and 5,837,878, as well as our copending applications: Ser. No. 08/689,341, titled Boronic Compound Complexing Reagents and Complexes, filed Aug. 5, 1996 now U.S. Pat. No. 5,847,192; Ser. No. 08/691,929, titled Boronic Compound Complexing Reagents and Highly Stable Complexes, filed Aug. 5, 1996 now U.S. Pat. No. 5,963,329; Ser. No. 08/689,283 (U.S. Pat. No. 5,837,878), titled Boronic Compound Complexing Reagents and Highly General Formula VIII

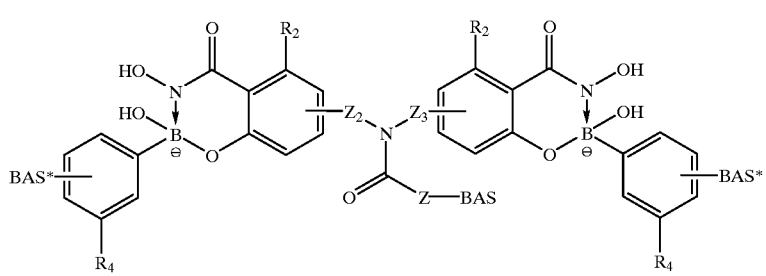

wherein groups $R_2$, $R_4$, Z, $Z_2$, $Z_3$, BAS and BAS* are as were previously defined.

Preparation of Bioconjugates of General Formulas V and VIII

Bioconjugates of General Formulas V and VIII may be prepared in buffered aqueous solutions or organic solvents. Preferred buffers include acetate, citrate, phosphate, carbonate and diglycine. Borate buffers should be avoided due to their ability to complex with the boronic compound complexing moiety. Trishydroxymethylaminomethane, β-hydroxyamine and β-hydroxyacid buffers should also be avoided due to their ability to complex with the phenylboronic acid. The bioconjugate is formed within a few minutes over a range of temperatures of from about 4° C. to 70° C. The bio-conjugation reaction (phenylboronic acid complexation) is insensitive to significant variations in ionic strength over the range 0.01 to 1 M, the presence of organic solvents including acetonitrile, methanol, ethanol, isopropanol, butanol, N,N-dimethylformamide and dimethylsulfoxide, the presence of detergents, and the presence of chaotropic agents (protein denaturants) including urea, guanidine hydrochloride, guanidine thiocyanate and Stable Complexes, filed Aug. 5, 1996; Ser. No. 08/691,930 (U.S. Pat. No. 5,837,878), titled Boronic Compound Complexing Reagents and Complexes, filed Aug. 5, 1996, which are incorporated herein by reference.

In particular, the aforementioned patents and copending applications detail the syntheses of the following compounds which are useful synthetic intermediates: methyl 4-aminomethyl-2-hydroxybenzoate hydrochloride, methyl 4-bromomethyl-2-hydroxybenzoate, methyl 4-aminomethyl-2,6-dihydroxybenzoate hydrochloride, methyl 4-bromomethyl-2,6-dihhydroxybenzoate, cyanomethyl 4-aminomethyl-2-hydroxybenzoate hydrochloride, ethyl (6-aminohexanoyl)aminomethyl-2-hydroxybenzoate trifluoroacetate, methyl (6-aminohexanoyl)aminomethyl-2, 6-dihydroxybenzoate hydrochloride, methyl 4-succinylaminomethyl-2-hydroxybenzoate succinimidyl ester, methyl (6-aminohexanoyl) aminomethyl-2-hydroxybenzoate hydrochloride, cyanomethyl 4-glutarylaminomethyl-2-hydroxybenzoate succinimidyl ester, and methyl 4-glutarylaminomethyl-2,6-dihydroxybenzoate succinimidyl ester.

The preparation of bifunctional boronic compound complexing reagents of General Formulas I and VI are summarized in FIGS. 4 through 10.

Figure 4:
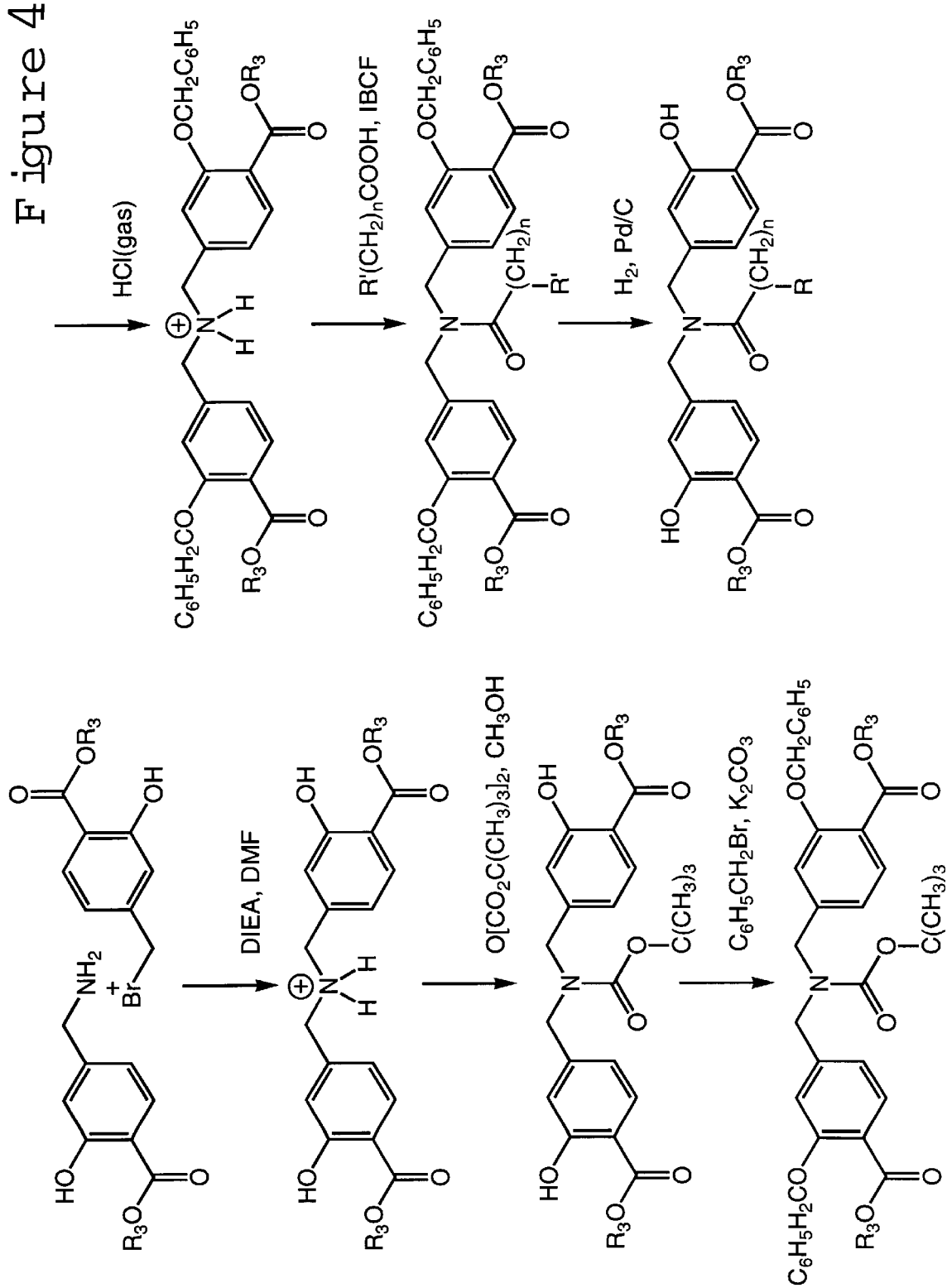
FIG. 4 summarizes a method for the preparation of reagents of General Formula I, wherein group Z is $(CH_2)_n$, wherein n is from 1 to 5, wherein group $Z_2$ and group $Z_3$ are each $CH_2$, and wherein group $R_3$ is an alkyl (e.g., methyl, ethyl, etc.) moiety.

FIG. 4 summarizes a method for the preparation of reagents of General Formula I, wherein group Z is $(CH_2)_n$, wherein groups $Z_2$ and $Z_3$ are each $CH_2Ar$, wherein the group Ar represents the aromatic ring to which the spacer $Z_2$ is appended, and wherein group $R_3$ is an alkyl (e.g., methyl, ethyl, etc.) moiety. Condensation of the benzylamine adduct with the benzylbromide adduct affords the secondary amine intermediate, which is isolated as the corresponding hydrochloride salt. It is to be appreciated that different moieties for spacers $Z_2$ and $Z_3$ may be formulated at this step by modifying the condensation reactants.

Neutralization of the amine hydrochloride produced by the condensation reaction and subsequent reaction with di-tert-butyldicarbonate affords the tert-butyloxycarbonyl (BOC) protected secondary amine. Alkylation of the phenolic hydroxyls associated with the BOC protected secondary amine with benzylbromide next affords the dibenzyl protected BOC secondary amine intermediate, which is reacted with anhydrous hydrogen chloride gas to effect removal of the BOC protecting group. The dibenzyl protected intermediate is next condensed with a carboxylic acid of the general formula $R'(CH_2)_nCOOH$, wherein group $R'$ is selected from one of a reactive electrophilic or nucleophilic moiety, and a protected reactive electrophilic or nucleophilic moiety having a protecting group which is subject to removal in the final step of the synthesis, and wherein n is from 1 to 5. The carboxylic acid is activated by reaction with isobutyl chloroformate prior to condensation with the dibenzyl protected intermediate. The reaction affords the dibenzyl protected penultimate product. Finally, the benzyl protecting groups, as well as any protecting groups associated with group $R'$, are removed by hydrogenation over palladium on carbon to afford a reagent of General Formula I.

Figure 5:
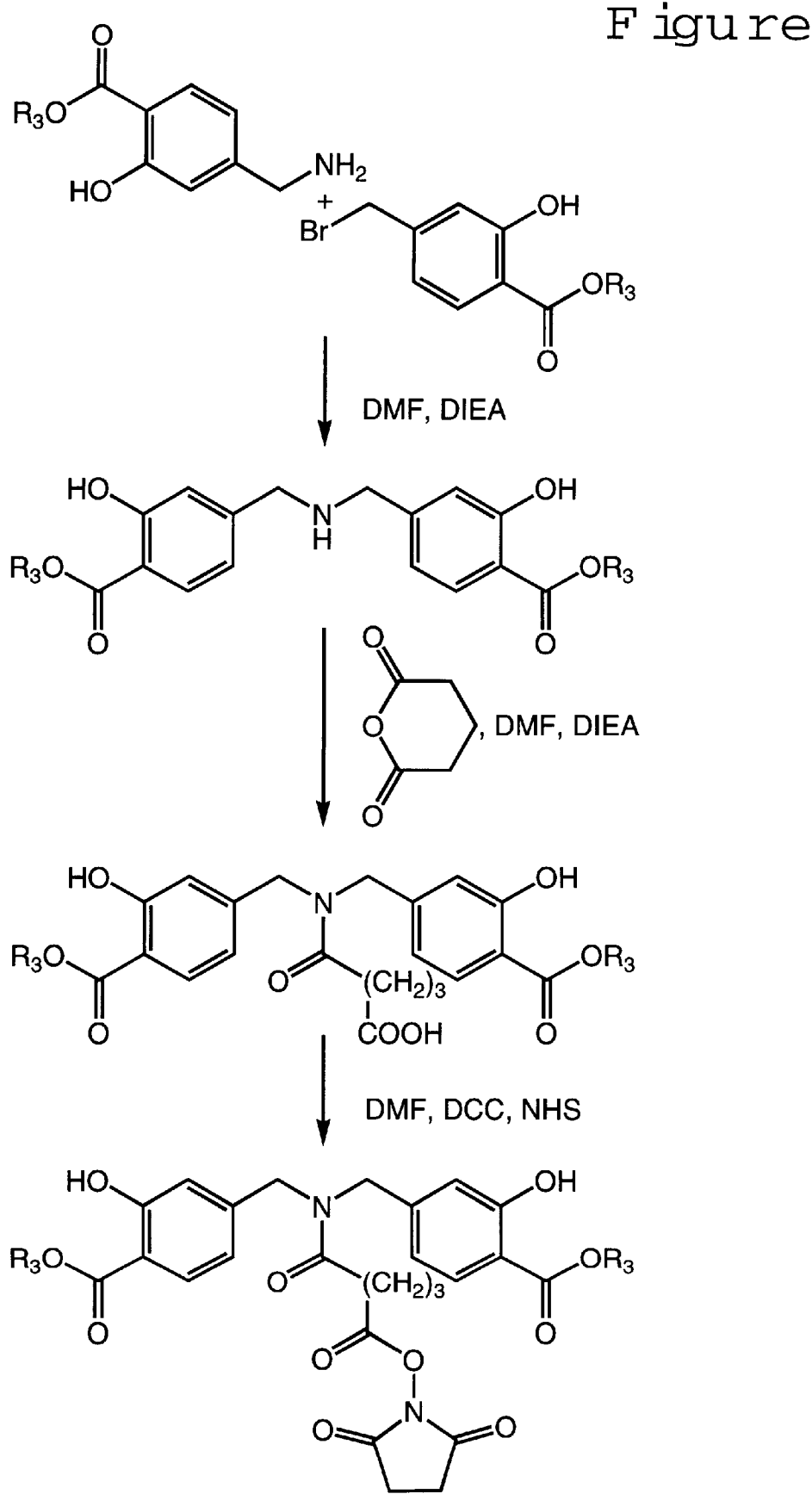
FIG. 5 summarizes a method for the preparation of reagents of General Formula I, wherein group R is a reactive electrophilic N-hydroxysuccinimidyl ester moiety, wherein group Z is $(CH_2)_3$, wherein group $Z_2$ and group $Z_3$ are each $CH_2$, and wherein group $R_3$ is an alkyl (e.g., methyl, ethyl, etc.) moiety.

FIG. 5 summarizes a method for the preparation of reagents of General Formula I, wherein group R is a reactive electrophilic N-hydroxysuccinimidyl ester moiety, wherein group Z is $(CH_2)_3$, wherein groups $Z_2$ and $Z_3$ are each $CH_2Ar$, wherein the group Ar represents the aromatic ring to which the spacer $Z_2$ or $Z_3$ is appended, and wherein group $R_3$ is an alkyl (e.g., methyl, ethyl, etc.) moiety. In the initial step of the synthesis, the secondary amine intermediate is prepared as described above with reference to FIG. 4. Condensation of the secondary amine intermediate with glutaric anhydride next affords the corresponding carboxylic acid intermediate, which is further functionalized by reaction with 1,3-dicyclohexylcarbodiimide and N-hydroxysuccinimide to afford a reagent of General Formula I, wherein R is a reactive electrophilic N-hydroxysuccinimidyl ester moiety.

Figure 6:
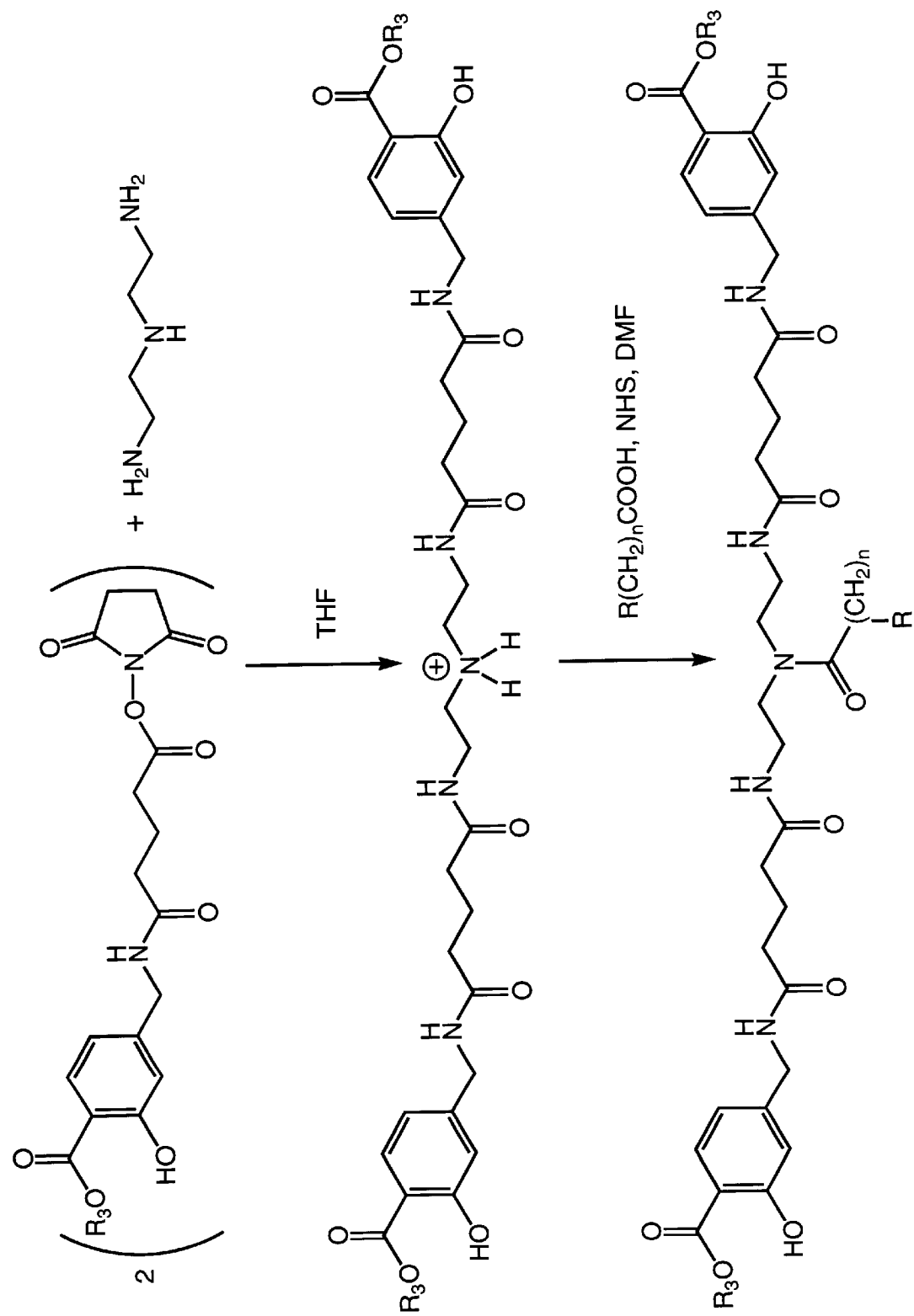
FIG. 6 summarizes a method for the preparation of reagents of General Formula I derived from diethylenetriamine, wherein group R is a reactive electrophilic or nucleophilic moiety, wherein group $R_3$ is selected from one of an alkyl (e.g., methyl, ethyl, etc.) and a methylene bearing an electronegative substituent, wherein group Z is $(CH_2)_n$, wherein n is from 1 to 5, and wherein group $Z_2$ and group $Z_3$ are each $CH_2CH_2NHCO(CH_2)_3$ CONHCH$_2$Ar, wherein the group Ar represents the aromatic ring to which the spacer Z$_2$ is appended.

FIG. 6 summarizes a method for the preparation of reagents of General Formula I, wherein group R is a reactive electrophilic or nucleophilic moiety, wherein group $R_3$ is selected from one of an alkyl (e.g., methyl, ethyl, etc.) and a methylene bearing an electronegative substituent, wherein group Z is $(CH_2)_n$, wherein n is from 1 to 5, and wherein groups $Z_2$ and $Z_3$ are each $CH_2CH_2NHCO(CH_2)_3CO$—$NHCH_2Ar$, wherein the group Ar represents the aromatic ring to which the spacer $Z_2$ or $Z_3$ is appended. Condensation of diethylenetriamine with two equivalents of a reagent selected from one of methyl, ethyl and cyanomethyl 4-glutarylaminomethyl-2-hydroxybenzoate succinimidyl ester affords the secondary amine intermediate, which is isolated as the corresponding N-hydroxysuccinimide salt. To afford different spacers for each of $Z_2$ and $Z_3$, one equivalent of a first succinimidyl ester may be condensed with the diethylenetriamine followed by condensation with one equivalent of a second succinimidyl ester different from the first ester. After neutralization of the N-hydroxysuccinimide salt, the secondary amine intermediate is condensed with a carboxylic acid of the general formula $R(CH_2)_n$ COOH, wherein group R is a reactive electrophilic or nucleophilic moiety, and wherein n is from 1 to 5. The carboxylic acid is first activated by reaction with 1,3-dicyclohexylcarbodiimide and N-hydroxysuccinimide, and affords upon reaction with the secondary amine intermediate a reagent of General Formula I.

Figure 7:
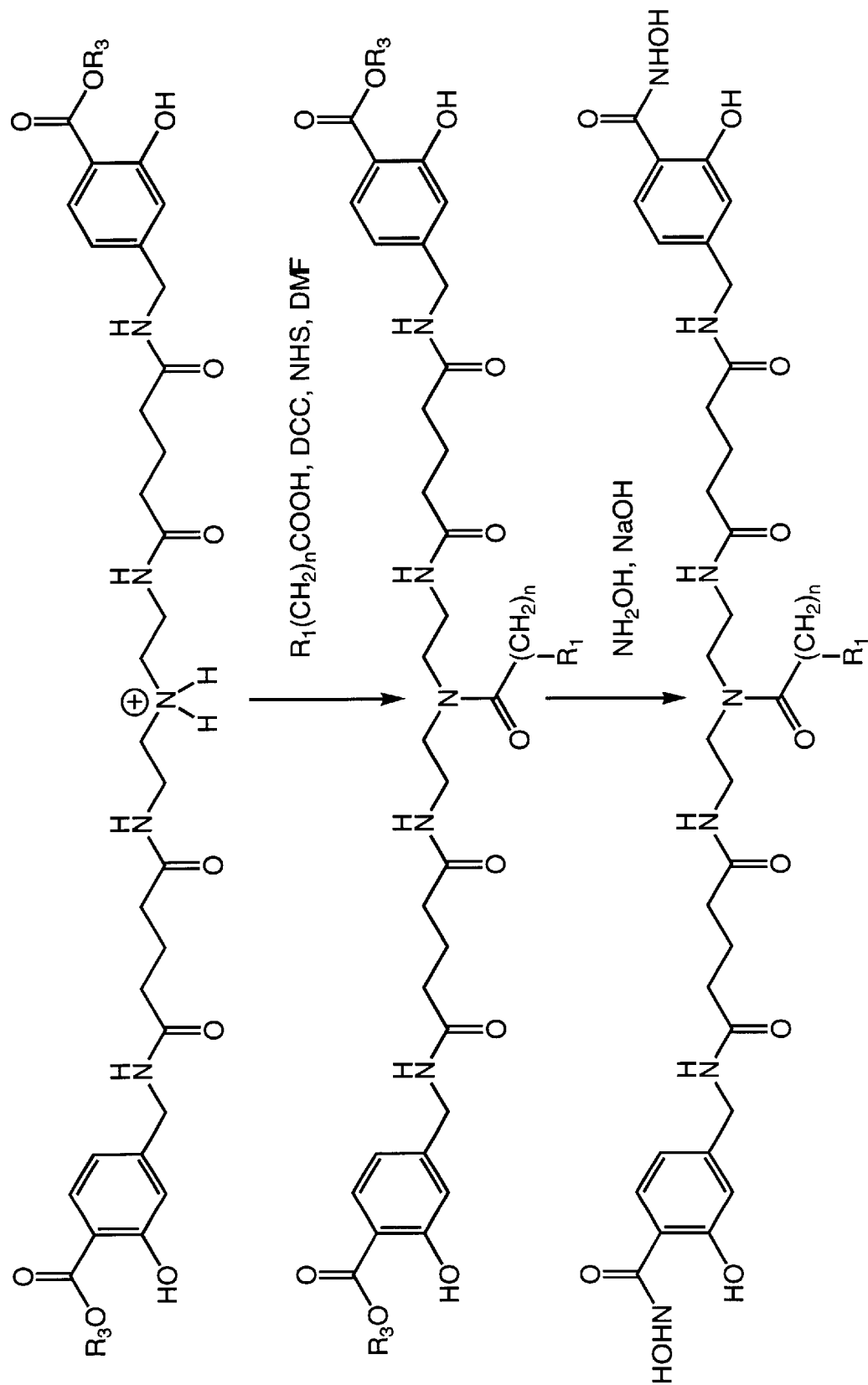
FIG. 7 summarizes a method for the preparation of reagents of General Formula VI derived from diethylenetriamine, wherein group R$_1$ is a reactive electrophilic or nucleophilic moiety, wherein group Z is (CH$_2$)$_n$, wherein n is from 1 to 5, and wherein group Z$_2$ and group Z$_3$ are each CH$_2$CH$_2$NHCO(CH$_2$)$_3$CO—NHCH$_2$Ar, wherein the group Ar represents the aromatic ring to which the spacer Z$_2$ or Z$_3$ is appended.

FIG. 7 summarizes a method for the preparation of reagents of General Formula VI, wherein group $R_1$ is a reactive electrophilic or nucleophilic moiety, wherein group Z is $(CH_2)_n$, wherein n is from 1 to 5, and wherein group $Z_2$ or $Z_3$ is $CH_2CH_2NH$—$CO(CH_2)_3CONHCH_2Ar$, wherein the group Ar represents the aromatic ring to which the spacer $Z_2$ or $Z_3$ is appended. A reagent of General Formula I, prepared as described above with reference to FIG. 6, is further reacted with an excess of aqueous hydroxylamine, to afford a reagent of General Formula VI.

Figure 8:
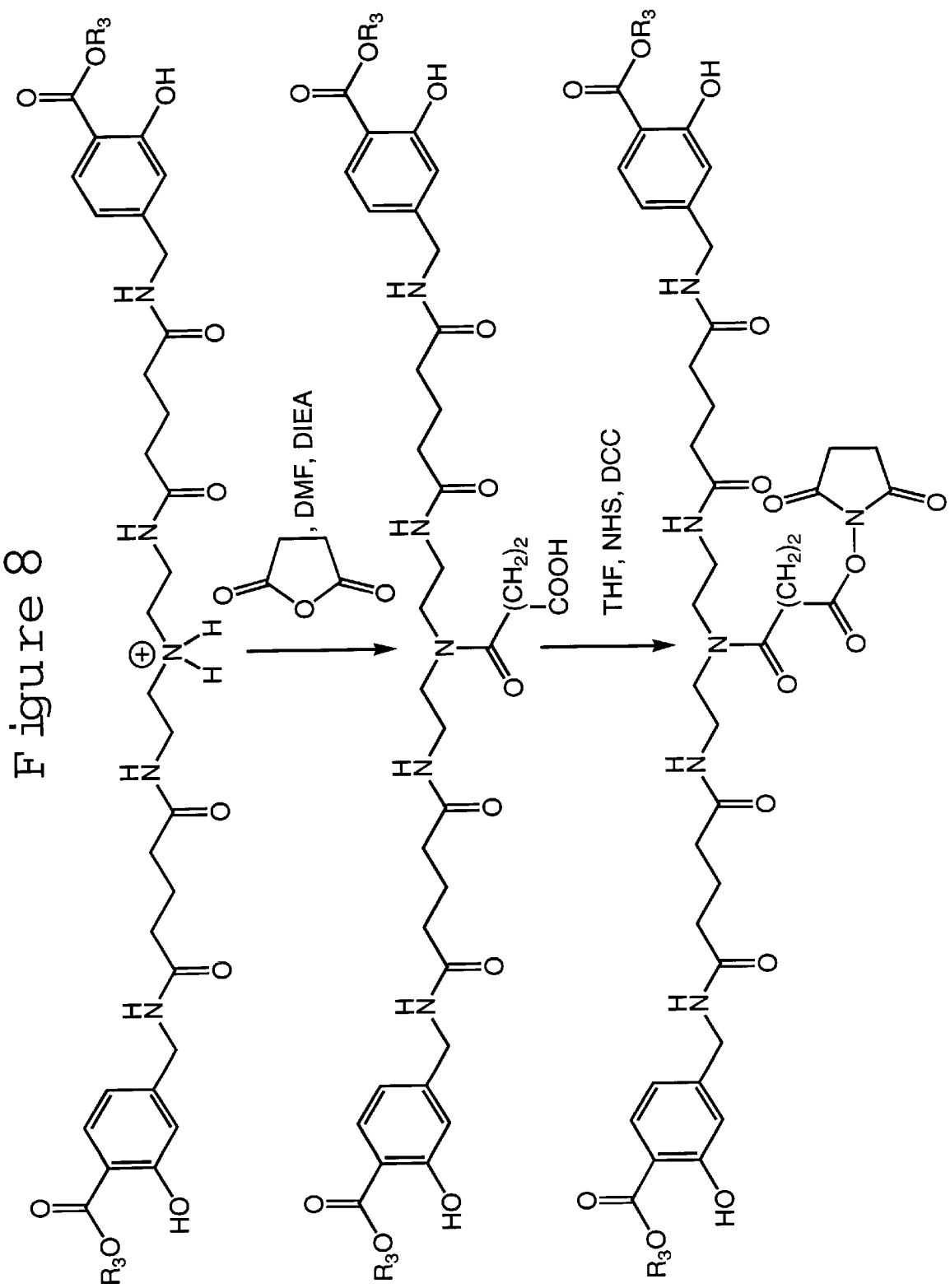
FIG. 8 summarizes a method for the preparation of reagents of General Formula I derived from diethylenetriamine, wherein group R is a reactive electrophilic N-hydroxysuccinimidyl ester moiety, wherein group R$_3$ is selected from one of an alkyl (e.g., methyl, ethyl, etc.) and a methylene bearing an electronegative substituent, wherein group Z is (CH$_2$)$_2$, and wherein group Z$_2$ and group Z$_3$ are each CH$_2$CH$_2$NHCO(CH$_2$)$_3$CONHCH$_2$Ar, wherein the group Ar represents the aromatic ring to which the spacer Z$_2$ or Z$_3$ is appended.

FIG. 8 summarizes a method for the preparation of reagents of General Formula I, wherein group R is a reactive electrophilic N-hydroxysuccinimidyl ester moiety, wherein group $R_3$ is selected from one of an alkyl (e.g., methyl, ethyl, etc.) and a methylene bearing an electronegative substituent, wherein group Z is $(CH_2)_2$, and wherein group $Z_2$ or $Z_3$ is $CH_2CH_2NHCO(CH_2)_3CONHCH_2Ar$, wherein the group Ar represents the aromatic ring to which the spacer $Z_2$ or $Z_3$ is appended. Condensation of the secondary amine intermediate, prepared as described above with reference to FIG. 6, with succinic anhydride affords the corresponding carboxylic acid intermediate, wherein Z is $(CH_2)_2$. Finally, reaction of the carboxylic acid intermediate with 1,3-dicyclohexylcarbodiimide and N-hydroxysuccinimide affords a reagent of General Formula I, wherein group R is a reactive electrophilic N-hydroxysuccinimidyl ester moiety.

Figure 9:
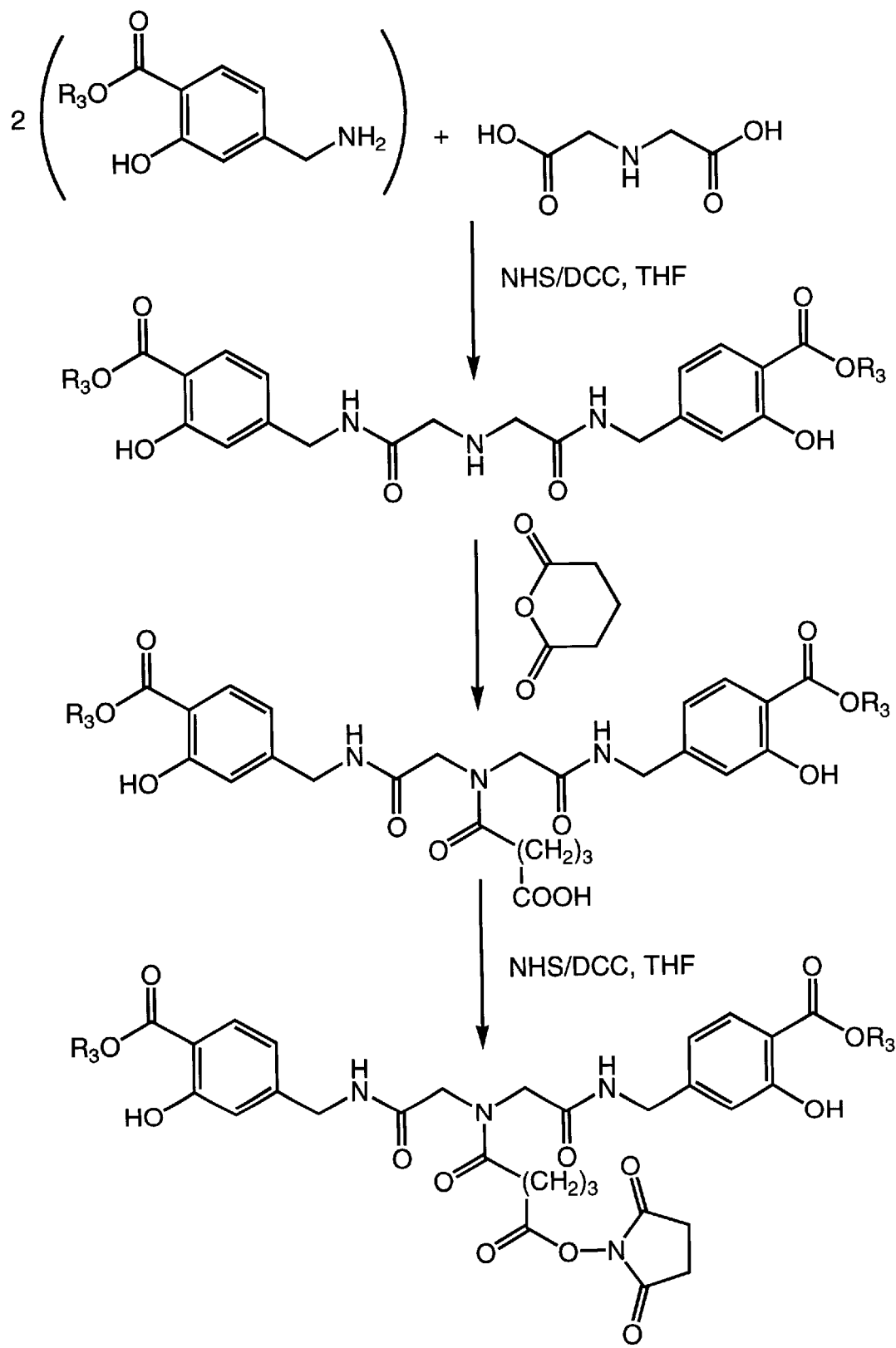
FIG. 9 summarizes a method for the preparation of reagents of General Formula I derived from iminodiacetic acid, wherein group R is a reactive electrophilic N-hydroxysuccinimidyl ester moiety, wherein group R$_3$ is selected from one of an alkyl (e.g., methyl, ethyl, etc.) and a methylene bearing an electronegative substituent, wherein group Z is (CH$_2$)$_3$, and wherein group Z$_2$ and group Z$_3$ are each CH$_2$CONHCH$_2$Ar, wherein the group Ar represents the aromatic ring to which the spacer Z$_2$ or Z$_3$ is appended.

FIG. 9 summarizes a method for the preparation of reagents of General Formula I, wherein group R is a reactive electrophilic N-hydroxysuccinimidyl ester moiety, wherein group $R_3$ is selected from one of an alkyl (e.g., methyl, ethyl, etc.) and a methylene bearing an electronegative substituent, wherein group Z is $(CH_2)_3$, wherein group $Z_2$ and group $Z_3$ are each $CH_2CONHCH_2Ar$, wherein the group Ar represents the aromatic ring to which the spacer $Z_2$ or $Z_3$ is appended. Condensation of iminodiacetic acid, 1,3-dicyclohexylcarbodiimide, and N-hydroxysuccinimide with two equivalents of a reagent selected from one of methyl, ethyl and cyanomethyl 4-aminomethyl-2-hydroxybenzoate affords the secondary amine intermediate, which is isolated as the corresponding hydrochloride salt. To afford different spacers for each of $Z_2$ and $Z_3$, one equivalent of a first hydroxybenzoate may be condensed with the iminodiacetic acid followed by condensation with one equivalent of a second hydroxybenzoate different from the first hydroxybenzoate. After neutralization of the hydrochloride salt, the secondary amine intermediate is next condensed with glutaric anhydride to afford the corresponding carboxylic acid intermediate, wherein Z is $(CH_2)_3$. Finally, reaction of the carboxylic acid synthetic intermediate with 1,3-dicyclohexylcarbodiimide and N-hydroxysuccinimide affords a reagent of General Formula I, wherein group R is a reactive electrophilic N-hydroxysuccinimidyl ester moiety.

Figure 10:
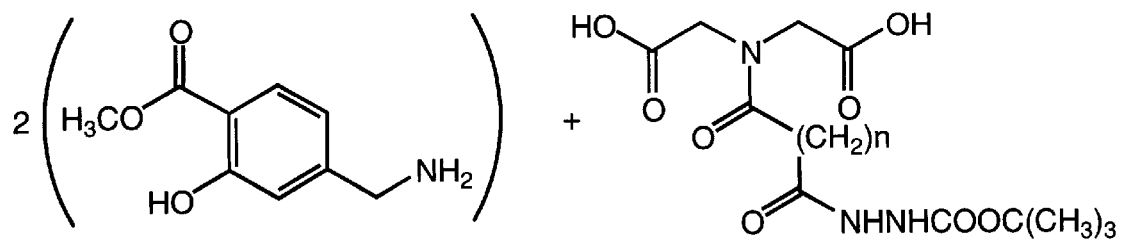
FIG. 10 summarizes a method for the preparation of reagents of General Formula VI derived from iminodiacetic acid, wherein group R$_1$ is a reactive nucleophilic hydrazide moiety, wherein group Z is (CH$_2$)$_3$, and wherein group Z$_2$ and group Z$_3$ are each CH$_2$CONHCH$_2$Ar, wherein the group Ar represents the aromatic ring to which the spacer Z$_2$ or Z$_3$ is appended.
Figure 10:
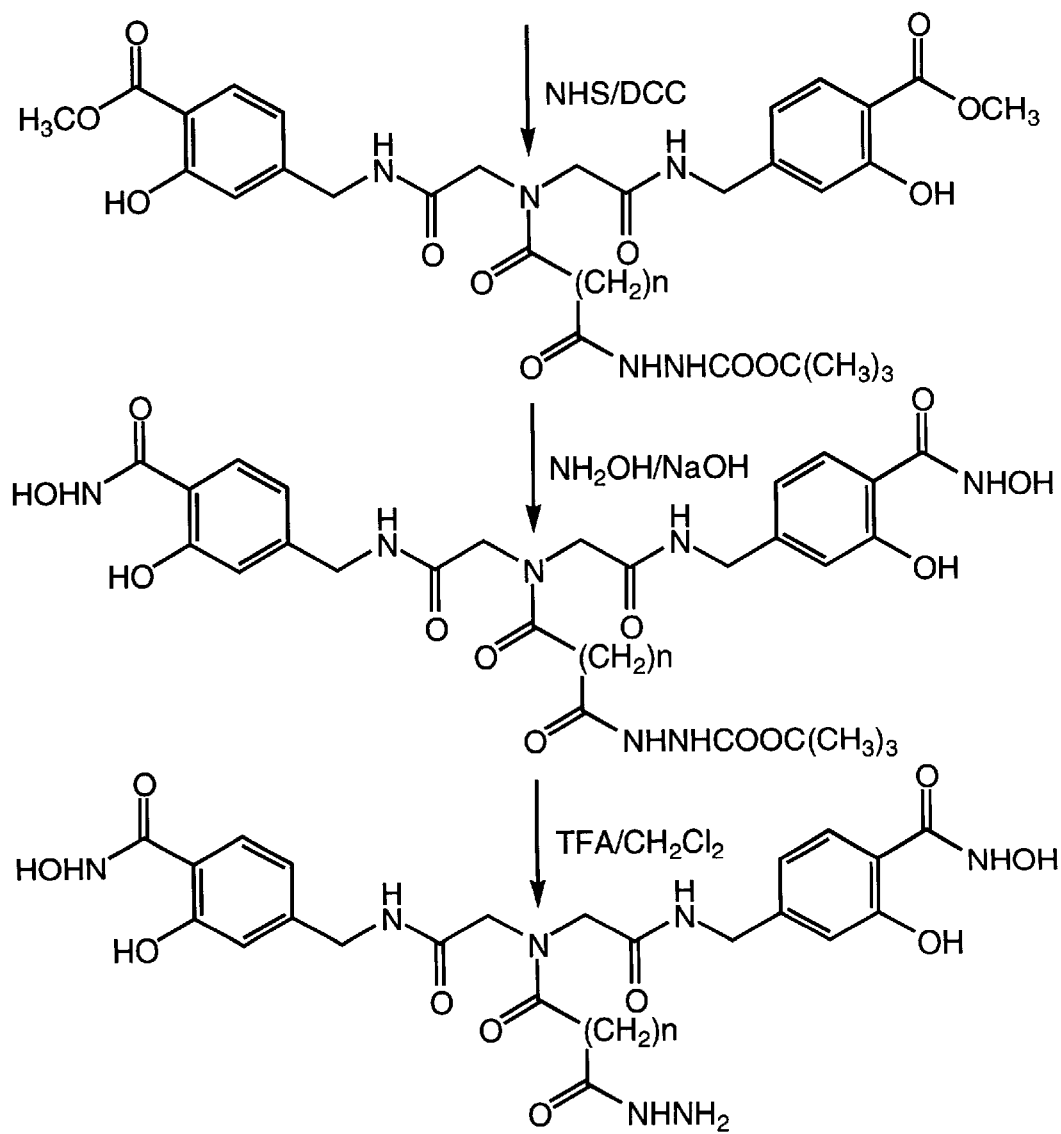

FIG. 10 summarizes a method for the preparation of reagents of General Formula VI, wherein group $R_1$ is a reactive nucleophilic hydrazide moiety, wherein group Z is $(CH_2)_3$, and wherein group $Z_2$ and group $Z_3$ are each CH₂CONHCH₂Ar, wherein the group Ar represents the aromatic ring to which the spacer $Z_2$ or $Z_3$ is appended. The iminodiactetic acid adduct depicted in FIG. 10 is first prepared by condensing iminodiacetic acid with an aliphatic dicarboxylic acid having one terminal tert-butyloxycarbonylhydrazide moiety, to afford the protected hydrazide iminodiacetic acid adduct. Reaction of the iminodiactetic adduct with two equivalents of methyl 4-aminomethyl-2-hydroxybenzoate affords the corresponding diamide intermediate, which is converted into the corresponding dihydroxamic acid intermediate by reaction with an excess of hydroxylamine. Finally, the protecting group is removed by reaction with trifluoroacetic acid to afford a reagent of General Formula VI, wherein group $R_1$ is a reactive nucleophilic hydrazide moiety. To afford alternative spacers for $Z_2$ and $Z_3$, one equivalent each of two different hydroxybenzoate esters may be condensed with the iminodiacetic adduct.

Figure 11:
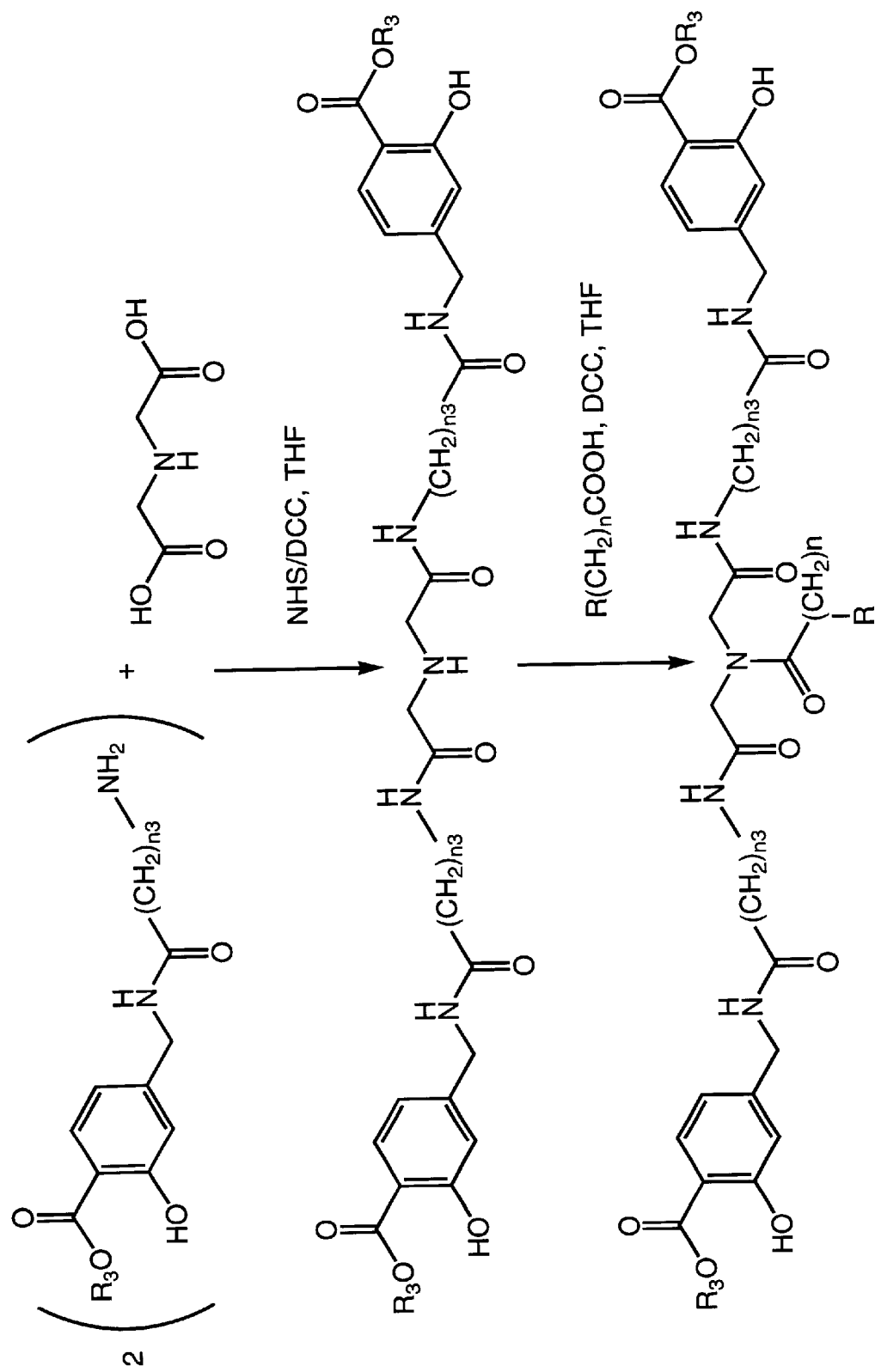
FIG. 11 summarizes a method for the preparation of reagents of General Formula I derived from iminoacetic acid, wherein group R is a reactive electrophilic or nucleophilic moiety, wherein group R$_3$ is selected from one of an alkyl (e.g., methyl, ethyl, etc.) and a methylene bearing an electronegative substituent, wherein group Z is (CH$_2$)$_n$, wherein n is from 1 to 5, wherein group Z$_2$ and group Z$_3$ are each CH$_2$CONH(CH$_2$)$_{n_3}$CONHCH$_2$Ar, wherein n$_3$ is from 1 to 5, and wherein the group Ar represents the aromatic ring to which the spacer Z$_2$ or Z$_3$ is appended.

FIG. 11 summarizes a method for the preparation of reagents of General Formula I, wherein group R is a reactive electrophilic or nucleophilic moiety, wherein group Z is $(CH_2)_n$, wherein n is from 1 to 5, wherein group $Z_2$ and group $Z_3$ are each $CH_2CONH(CH_2)_{n_3}CONHCH_2Ar$, wherein $n_3$ is from 1 to 5, and wherein the group Ar represents the aromatic ring to which the spacer $Z_2$ or $Z_3$ is appended. Condensation of iminodiacetic acid; 1,3-dicyclohexylcarbodiimide; and N-hydroxysuccinimide with two equivalents of a reagent selected from one of methyl, ethyl and cyanomethyl 4-aminomethyl-2-hydroxybenzoate affords the secondary amine intermediate, which is isolated as the corresponding hydrochloride salt. After neutralization of the hydrochloride salt, the secondary amine intermediate is next condensed with a carboxylic acid of the general formula $R(CH_2)_nCOOH$, wherein group R is a reactive electrophilic or nucleophilic moiety, and wherein n is from 1 to 5. The carboxylic acid is first activated by reaction with 1,3-dicyclohexylcarbodiimide and N-hydroxysuccinimide, and affords upon reaction with the secondary amine intermediate a reagent of General Formula I.

EXAMPLES

The following examples present a detailed description of the synthesis of reagents of General Formulas I and VI. Additional examples present a detailed description of the preparation of conjugates of General Formulas III and VII and bioconjugates of General Formulas V and VIII.

Example I

Preparation of Ethyl 4-(Bromomethyl)-2-hydroxybenzoic Acid

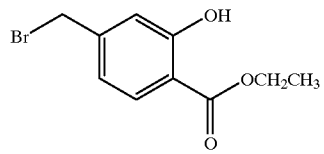

Ethyl 4-Methyl-2 hydroxybenzoate

4-Methyl-2-hydroxybenzoic acid (20.0 g, 131 mmoles) was dissolved in ethanol (300 mL) and concentrated sulfuric acid (2.0 mL) was added. The mixture was refluxed for 40 hours. The volume of the reaction mixture was reduced to 100 mL, transferred to a separatory funnel, and diluted with chloroform (250 mL) and water (200 mL). Solid sodium bicarbonate was added in small portions until the pH of the aqueous layer was about 8 (pH test paper). The mixture in the funnel was shaken well and the layers separated. The organic layer was washed first with water (150 mL) and then saturated aqueous sodium chloride (150 mL). Finally, the organic solution was dried over anhydrous magnesium sulfate, filtered, and the solvent evaporated to afford 14.0 g (59% yield) of liquid ethyl 4-methyl-2-hydroxybenzoate.

¹H NMR (300 MHz, CHCl₃-d) δ 1.40 (triplet, J=7 Hz, 3H, CH₂CH₃), 2.33 (singlet, 3H, ArCH₃), 4.38 (quartet, J=7 Hz, 2H, CH₂CH₃), 6.67 (doublet, J=8 Hz, 1H, ArH), 6.78 (singlet, 1H, ArH), 7.72 (doublet, J=8 Hz, 1H, ArH), 10.81 (singlet, 1H, OH). ¹³C NMR (75 MHz, CHCl₃-d) δ 14.0, 21.7, 61.1, 110.1, 117.7, 120.4, 129.7, 146.9, 161.7, 170.3.

Ethyl 4-Bromomethyl-2-hydroxybenzoic Acid

Ethyl 4-methyl-2-hydroxybenzoate (13.1 g, 72.5 mmoles) was dissolved in carbon tetrachloride (150 mL) and N-bromosuccinimide (13.1 g, 73.2 mmoles) and benzoyl peroxide (0.2 g, 0.8 mmoles) were added. The mixture was refluxed for 3.5 hours and then allowed to cool to room temperature. The solids were removed by filtration and the filtrate was evaporated to dryness. The crude solid product was crystallized from hexane (100 mL) to afford 5.0 g (27% yield) of ethyl 4-bromomethyl-2-hydroxybenzoic acid (m.p. 64–66° C.).

¹H NMR (300 MHz, CHCl₃-d) δ 1.41 (triplet, J=7 Hz, 3H, CH₂CH₃), 4.40 (quartet, J=7 Hz, 2H, CH₂CH₃), 4.40 (singlet, 2H, CH₂Br), 6.90 (doublet, J=8 Hz, 1H, ArH), 6.99 (singlet, 1H, ArH), 7.82 (doublet, J=8 Hz, 1H, ArH), 10.88 (singlet, 1H, OH). ¹³C NMR (75 MHz, CHCl₃-d) δ 14.0, 31.9, 61.5, 112.4, 117.9, 119.8, 130.5, 145.5, 161.8, 169.9.

Example II

Preparation of Ethyl 4-(Aminomethyl)-2-hydroxybenzoate Hydrochloride

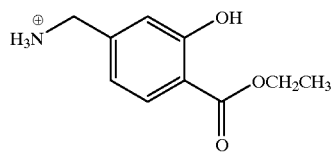

Ethyl 4-Aminomethyl-2-hydroxybenzoate Hydrochloride

Ethyl 4-(bromomethyl)-2-hydroxybenzoate (4.8 g, 18.6 mmoles) was dissolved in dry N,N-di-methylformamide (50 mL) and sodium azide (1.2 g, 18.9 mmoles) was added. The suspension was stirred at room temperature for 2 hours. The reaction mixture was then diluted with dichloromethane (150 mL) and extracted with 1 N aqueous hydrochloric acid (100 mL), water (100 mL), and saturated aqueous sodium chloride (50 mL). Finally, the solution was then dried over anhydrous magnesium sulfate, filtered, and evaporated to dryness to give ethyl 4-azidomethylsalicyalte as an oil.

Palladium on carbon (0.5 g; 10% [w/w]) was added to a IL hydrogenation flask under a nitrogen atmosphere. The crude ethyl 4-azidomethyl-2-hydroxybenzoate was dissolved in ethanol (200 mL) and transferred to the hydrogenation flask. Concentrated aqueous hydrochloric acid (2 mL) was then added, and the flask was affixed to the Parr hydrogenator. The reaction mixture was shaken under 35 psi of hydrogen for 4 hours at room temperature. The mixture was then filtered through Celite to remove the catalyst, and the filtrate was evaporated to dryness to afford an off-white solid. Finally, this solid was crystallized from EtOH to afford 3.1 g (71% yield) of ethyl 4-(aminomethyl)-2-hydroxybenzoate hydrochloride (m.p. 240–241° C.).

$^1$H NMR (300 MHz, DMSO-d$_6$) δ 1.30 (triplet, J=7 Hz, 3H, CH$_2$CH$_3$), 3.99 (singlet, 2H, CH$_2$NH$_3$), 4.33 (quartet, J=7 Hz, 2H, CH$_2$CH$_3$), 7.06 (doublet, J=8 Hz, 1H, ArH), 7.15 (singlet, 1H, ArH), 7.77 (doublet, J=8 Hz, 1H, ArH), 8.71 (broad singlet, 3H, NH$_3$), 10.62 (broad singlet, 1H, OH). $^{13}$C NMR (75 MHz, DMSO-d$_6$) δ 14.0, 38.7, 41.6, 61.5, 112.9, 117.7, 119.8, 130.3, 142.2, 160.2, 168.9.

Example III

Preparation of Methyl 4-(Aminomethyl)-2,6-dihydroxybenzoate Hydrochloride

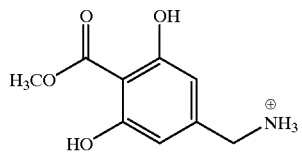

Methyl 4-Methyl-2,6-diacetoxybenzoate

Methyl 4-methyl-2,6-dihydroxybenzoate (14.0 grams, 76.8 mmoles) was dissolved in anhydrous dichloromethane (250 mL) and acetic anhydride (21 mL, 223 mmoles) and anhydrous pyridine (18 mL, 223 mmoles) were added carefully. The solution was refluxed under dry nitrogen for 30 hours, then cooled to room temperature. The solution was washed twice with 1 M aqueous hydrochloric acid (200 mL portions) and then with saturated aqueous sodium chloride (200 mL). The dichloromethane solution was dried over anhydrous magnesium sulfate, filtered, and evaporated to an off-white solid. This crude product was flash chromatographed on silica gel (250 grams) using hexanes:ethyl acetate (70:30 [v/v]) as the eluting solvent. Fractions containing the major product (R$_f$=0.3) were pooled and evaporated to dryness to afford 19.0 grams (98% yield) of a white solid of methyl 4-methyl-2,6-diacetoxybenzoate (m.p. 70–71° C., open capillary, uncorrected).

$^1$H NMR (300 MHz, CHCl$_3$-d) δ 2.27 (singlet, 6H, COCH$_3$), 2.37 (singlet, 3H, ArCH$_3$), 3.83 (singlet, 3H, OCH$_3$), 6.84 (singlet, 2H, ArH). $^{13}$C NMR (75 MHz, CHCl$_3$-d) δ 20.9, 21.5, 52.4, 116.5, 122.1, 143.8, 150.2, 163.9, 169.4.

Methyl 4-(Bromomethyl)-2,6-diacetoxybenzoate

Methyl 4-methyl-2,6-diacetoxybenzoate (14.9 grams, 56.0 mmoles) was dissolved in carbon tetrachloride (200 mL), and N-bromosuccinimide (11.1 grams, 62.2 mmoles) and benzoyl peroxide (0.2 grams, 0.8 mmoles) were added. The mixture was refluxed under nitrogen. After 3.5 hours, an additional portion (0.2 grams) of N-bromosuccinimide was added. Reflux was continued for an additional hour. The reaction mixture was cooled to room temperature and then in ice for 1 hour, and the solid removed by filtration. The filtrate was evaporated to dryness. Hexanes (250 mL) was added to the residue, and the mixture was boiled until dissolution was obtained. The hexanes solution was concentrated to about 75 mL when a solid just began to precipitate. The mixture was heated to dissolve the solid, and the solution was allowed to cool slowly to room temperature. White crystals formed slowly, and the mixture was chilled in ice for 2 hours to complete crystallization. The solid was filtered, washed with cold hexanes (100 mL), and dried in vacuo to afford 11.9 grams (62% yield) of methyl 4-bromomethyl-2,6-diacetoxy-benzoate (m.p. 93–95° C., open capillary, uncorrected). The product was contaminated with a small amount of methyl 2,6-diacetoxy-4-dibromomethylbenzoate, which did not interfere with subsequent reactions.

$^1$H NMR (300 MHz, CHCl$_3$-d) δ 2.29 (singlet, 6H, COCH$_3$), 3.85 (singlet, 3H, OCH$_3$), 4.41 (singlet, 2H, CH$_2$), 7.08 (singlet, 2H, ArH). $^{13}$C NMR (75 MHz, CHCl$_3$-d) 820.9, 30.9, 52.7, 119.6, 121.8, 142.4, 150.2, 163.5, 169.1.

Methyl 4-(Aminomethyl)-2,6-dihydroxybenzoate Hydrochloride

Methyl 4-(bromomethyl)-2,6-diacetoxybenzoate (45.8 grams, 133 mmoles) was dissolved in N,N-dimethylformamide (150 mL), and sodium azide (8.8 g, 135 mmoles) was added. The reaction mixture was stirred for 6 hours at room temperature. Dichloromethane (350 mL) was added to the reaction mixture, and this solution was washed with water (250 mL), 1 M aqueous hydrochloric acid (250 mL), and saturated aqueous sodium chloride (150 mL). The organic solution was dried over anhydrous magnesium sulfate, filtered, and evaporated to a clear, pale yellow oil. The oil was dissolved in methanol (750 mL) and transferred to a 2 L Parr hydrogenation flask.

Palladium on carbon catalyst (10% [w/w], 1.5 g) in water (10 mL) was added, followed by concentrated hydrochloric acid (15 mL). The flask was affixed to a Parr hydrogenator, and the mixture was shaken at room temperature under 30 psi of hydrogen for 24 hours. The reaction mixture was filtered through a 0.45 mm nylon filter. The retained solid was then washed with methanol (150 mL), and concentrated hydrochloric acid (7 mL) was added to the filtrate. The filtrate was heated to reflux for 2 hours, cooled to room temperature, and evaporated to dryness to give an off-white solid. This solid was dissolved in hot denatured ethanol (250 mL) and the solution was allowed to cool to room temperature. White crystals formed quickly. The mixture was then chilled for 16–18 hours at 4° C. to complete crystallization. The solid was filtered, washed with a little cold ethanol (50 mL) and then diethyl ether (150 mL), and dried in vacuo over potassium hydroxide pellets to afford 16.0 grams (52% yield based on monobromo starting material) of methyl 4-aminomethyl-2,6-dihydroxybenzoate hydrochloride (m.p. >260° C., open capillary, uncorrected).

$^1$H NMR (300 MHz, DMSO-d$_6$) δ 3.77 (singlet, 3H, OCH$_3$), 3.83 (singlet, 2H, CH$_2$), 6.44 (singlet, 2H, ArH), 8.35 (broad singlet, 3H, NH$_3$), 10.20 (singlet, 2H, OH). $^{13}$C NMR (75 MHz, DMSO-d$_6$) 641.9, 52.1, 107.2, 107.3, 138.5, 157.6, 168.3.

Example IV

Preparation of Ethyl 4-[(6-aminohexanoylamino)methyl]-2-hydroxybenzoate Trifluoroacetate

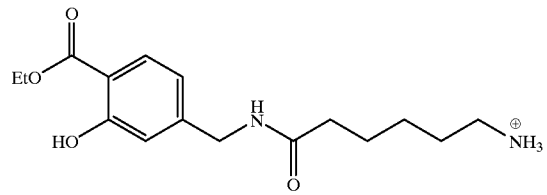

Ethyl (N-tert-Butoxycarbonyl-6-aminohexanoyl)aminomethyl-2-hydroxybenzoate Ethyl 4-aminomethyl-2-hydroxybenzoate hydrochloride (0.52 g, 1.28 mmoles) was suspended in anhydrous N,N-dimethylformamide (25 mL), and N,N-diisopropylethylamine (0.79 mL, 4.53 mmoles) was added, followed by N-tert-butoxycarbonyl-6-aminohexanoic acid succinimidyl ester (0.74 g, 2.26 mmoles). The mixture was stirred under dry nitrogen for 18 hours, during which time all solids dissolved. The reaction mixture was diluted with ethyl acetate (100 mL) and extracted with 1 N aqueous hydrochloric acid (100 mL). The layers were separated, and the ethyl acetate solution was washed with water (100 mL) and saturated aqueous sodium chloride (500 mL). The ethyl acetate solution was dried over anhydrous magnesium sulfate, filtered, and evaporated to afford an amorphous off-white solid. Finally, the solid was crystallized from ethyl acetate, filtered, and dried in vacuo to afford 0.67 g (73% yield) of ethyl (N-tert-butoxycarbonyl-6-aminohexanoyl)aminomethyl-2-hydroxybenzoate (m.p. 120–121° C., open capillary, uncorrected).

$^1$H NMR (300 MHz, DMSO-$d_6$) δ 1.19 (multiplet, 2H, NHCH$_2$CH$_2$CH$_2$CH$_2$CH$_2$CO), 1.34 (multiplet, 5H, CH$_2$CH$_2$CO and CH$_2$CH$_3$), 1.34 (singlet, 9H, C(CH$_3$)$_3$), 1.49 (multiplet, 2H, NHCH$_2$CH$_2$), 2.12 (triplet, J=7 Hz, 2H, CH$_2$CH$_2$CO), 2.87 (quartet, J=6 Hz, 2H, NHCH$_2$CH$_2$), 4.23 (doublet, J=6 Hz, 2H, CH$_2$Ar), 4.32 (quartet, J=7 Hz, CH$_2$CH$_3$), 6.74 (triplet, J=6 Hz, 1H, CONHCH$_2$CH$_2$), 6.80 (doublet, J=8 Hz, 1H, ArH), 6.81 singlet, 1H, ArH), 7.71 (doublet, J=8 Hz, 1H, ArH), 8.34 (triplet, J=6 Hz, 1H, CONHCH$_2$Ar), 10.58 (singlet, 1H, OH). $^{13}$C NMR (75 MHz, DMSO-$d_6$) δ 14.0, 25.1, 26.3, 28.3, 29.7, 36.3, 40.2, 42.9, 61.4, 79.0, 111.6, 116.0, 118.3, 130.4, 146.9, 156.2, 161.9, 170.1, 173.0.

Ethyl (6-Aminohexanoyl)aminomethyl-2-hydroxybenzoate Trifluoroacetate

Ethyl (N-tert-butoxycarbonyl-6-aminohexanoyl) aminomethyl-2-hydroxybenzoate (0.58 g, 1.41 mmoles) was dissolved in dichloromethane (5 mL) and the solution was cooled in an ice/water bath. Trifluoroacetic acid (5 mL) was added, and the reaction was allowed to warm to room temperature. After 2 hours, the reaction mixture was evaporated to dryness to give the product as an oil, which was dried in vacuo over potassium hydroxide pellets to afford 0.59 g (99% yield) of ethyl (6-aminohexanoyl) aminomethyl-2-hydroxybenzoate trifluoroacetate.

$^1$H NMR (300 MHz, DMSO-$d_6$) δ 1.28 (multiplet, 5H, H$_3$CH$_2$CH$_2$CH$_2$CH$_2$CH$_2$CO and CH$_2$CH$_3$), 1.53 (multiplet, 4H, NH$_3$CH$_2$CH$_2$CH$_2$CH$_2$CH$_2$CO), 2.15 (triplet, J=8 Hz, 2H, CH$_2$CH$_2$CO), 2.71 (multiplet, 2H, NH$_3$CH$_2$CH$_2$), 4.21 (doublet, J=6 Hz, 2H, CH$_2$Ar), 4.30 (quartet, J=8 Hz, 2H, CH$_2$CH$_3$), 6.79 (doublet, J=8 Hz, 1H, ArH), 6.81 (singlet, 1H, ArH), 7.68 (doublet, J=8 Hz, 1H, ArH), 8.18 (broad singlet, 3H, NH$_3$), 8.60 (triplet, J=6 Hz, 1H, CONHCH$_2$Ar), 10.58 (broad singlet, 1H, OH). $^{13}$C NMR (75 MHz, DMSO-$d_6$) δ 14.0, 24.8, 25.6, 26.7, 35.1, 38.6, 41.7, 61.3, 111.5, 115.5, 118.3, 130.1, 148.6, 160.6, 169.2, 172.6.

Example V

Preparation of Methyl 4-[(6-Aminohexanoylamino) methyl]-2,6-dihydroxybenzoate Hydrochloride

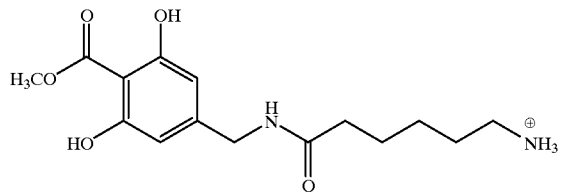

Methyl (N-tert-Butoxycarbonyl-6-aminohexanoyl) aminomethyl-2,6-dihydroxybenzoate Methyl 4-(aminomethyl)-2,6-dihydroxybenzoate hydrochloride (1.50 grams, 6.4 mmoles) was suspended in anhydrous N,N-dimethylformamide (25 mL), and N,N-diisopropylethylamine (2.2 mL, 12.8 mmoles) was added, followed by N-tert-butoxycarbonyl- 6-aminohexanoic acid succinimidyl ester (2.10 grams, 6.4 mmoles). The mixture was stirred under dry nitrogen for 4 hours, during which time all solids dissolved. The solvent was then evaporated to leave a light brown syrup, which was partitioned between ethyl acetate (70 mL) and 1 M aqueous hydrochloric acid (50 mL). The layers were separated, and the ethyl acetate solution was washed with saturated aqueous sodium bicarbonate (50 mL) and saturated aqueous sodium chloride (50 mL). The ethyl acetate solution was dried over anhydrous sodium sulfate, filtered, and evaporated to an amorphous off-white solid.

The solid was crystallized from ethyl acetate/hexanes, filtered, and dried in vacuo to afford 2.10 grams (80% yield) of methyl (N-tert-butoxycarbonyl-6-aminohexanoyl) aminomethyl-2,6-dihydroxybenzoate (m.p. 73–76° C., open capillary, uncorrected).

$^1$H NMR (300 MHz, DMSO-$d_6$) δ 1.26 (multiplet, 2H, NHCH$_2$CH$_2$CH$_2$CH$_2$CH$_2$CO), 1.36 (multiplet, 2H, CH$_2$CH$_2$CO), 1.36 (singlet, 9H, C(CH$_3$)$_3$), 1.50 (multiplet, 2H, NHCH$_2$CH$_2$), 2.10 (triplet, J=7 Hz, 2H, CH$_2$CH$_2$CO), 2.87 (quartet, J=6 Hz, 2H, NHCH$_2$CH$_2$), 3.78 (singlet, 3H, OCH$_3$), 4.08 (doublet, J=6 Hz, 2H, CH$_2$Ar), 6.23 (singlet, 2H, ArH), 6.75 (triplet, J=6 Hz, 1H, CONHCH$_2$CH$_2$), 8.26 (triplet, J=6 Hz, 1H, CONHCH$_2$Ar), 10.04 (singlet, 2H, OH). $^{13}$C NMR (75 MHz, CHCl$_3$-d) δ 25.0, 26.0, 28.3, 29.3, 35.3, 41.7, 52.0, 77.4, 104.3, 105.6, 145.8, 155.8, 158.2, 169.0, 172.4.

Methyl (6-Aminohexanoyl)aminomethyl-2,6-dihydroxybenzoate Hydrochloride

Methyl (N-tert-butoxycarbonyl-6-aminohexanoyl) aminomethyl-2,6-dihydroxybenzoate (2.00 grams, 4.87 mmoles) was dissolved in ethyl acetate (50 mL), and dry hydrogen chloride was bubbled slowly through the solution. The reaction mixture warmed as the gas dissolved. After 5 minutes, the gas was shut off, and the solution was stirred at room temperature. A white precipitate formed in the solution. After 30 minutes, the reaction mixture was chilled in ice for 2 hours, then the solid was filtered, washed with ethyl acetate (50 mL) and then diethyl ether (50 mL), and dried in vacuo over potassium hydroxide pellets to afford 1.68 grams (99% yield) of methyl (6-aminohexanoyl)aminomethyl-2,6-dihydroxybenzoate hydrochloride (m.p. shrinks at 145° C., decomposes with effervescence at 152–154° C., open capillary, uncorrected).

$^1$H NMR (300 MHz, DMSO-$d_6$) δ 1.29 (multiplet, 2H, 1 H$_3$CH$_2$CH$_2$CH$_2$CH$_2$CH$_2$CO), 1.55 (multiplet, 4H, NH$_3$CH$_2$CH$_2$CH$_2$CH$_2$CH$_2$CO), 2.13 (triplet, J=8 Hz, 2H, CH$_2$CH$_2$CO), 2.70 (multiplet, 2H, NH$_3$CH$_2$CH$_2$), 3.75 (singlet, 3 H, OCH$_3$), 4.07 (doublet, J=6 Hz, 2H, CH$_2$Ar), 6.26 (singlet, 2H, ArH), 8.05 (broad singlet, 3H, NH$_3$), 8.39 (triplet, J=6 Hz, 1H, CONHCH$_2$Ar), 9.84 (broad singlet, 2H, OH). $^{13}$C NMR(75 MHz, CHCl$_3$-d) δ 24.8, 25.6, 26.7, 35.1, 41.8, 52.0, 104.7, 105.5, 145.5, 158.1, 169.0, 172.3.

Example VI

Preparation of N-Hydroxysuccinimidyl 3-(N-{[3-hydroxy-4-(methoxycarbonyl)phenyl]methyl}carbamoyl)propionate

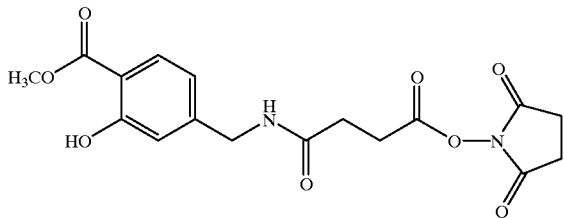

Methyl 4-Methyl-2-hydroxybenzoate

4-Methyl-2-hydroxybenzoic acid (100 g, 658 mmoles) was dissolved in anhydrous methanol (500 mL) and concentrated sulfuric acid (25 mL) was added carefully. The solution was refluxed for 18 hours, then cooled to room temperature. The reaction mixture was concentrated to about 150 mL, and ethyl acetate (250 mL) was added. The ethyl acetate solution was washed twice with saturated aqueous sodium bicarbonate (250 mL portions) and then with saturated aqueous sodium chloride (100 mL). The ethyl acetate solution was dried over anhydrous sodium sulfate, filtered, and evaporated to a clear, reddish-brown liquid. This crude product was vacuum distilled (oil pump) to afford a clear, viscous liquid that solidified on standing to afford 98.1 g (90% yield) of methyl 4-methyl-2-hydroxybenzoate.

$^1$H NMR (300 MHz, CHCl$_3$-d) δ 2.32 (singlet, 3H, ArCH$_3$), 3.91 (singlet, 3H, OCH$_3$), 6.67 (doublet, J=8 Hz, 1H, ArH), 6.78 (singlet, 1H, ArH), 7.69 (doublet, J=8 Hz, 1H, ArH), 10.71 (singlet, 1H, OH). $^{13}$C NMR (75 MHz, CHCl$_3$d) δ 21.8, 52.1, 110.0, 117.9, 120.6, 129.9, 147.3, 161.9, 170.9.

Methyl 4-(Bromomethyl)-2-hydroxybenzoate

Methyl 4-methyl-2-hydroxybenzoate (98.1 g, 590 mmoles) was dissolved in carbon tetrachloride (600 mL), and N-bromosuccinimide (105.0 g, 590 mmoles) and benzoyl peroxide (0.7 g, 3 mmoles) were added. The mixture was refluxed under nitrogen. After 2 hours, an additional portion (0.7 g) of N-bromosuccinimide was added. Reflux was continued for 16 hours. The reaction mixture was cooled to room temperature and the solid removed by filtration. The yellow filtrate was evaporated to dryness to afford a thick yellow syrup that solidified on standing. Hexanes (500 mL) was added to the solid, and the mixture was boiled until almost all solids dissolved. The hot hexanes solution was filtered and concentrated until a solid just began to precipitate. The mixture was heated to dissolve the solid, and the solution was allowed to cool slowly to room temperature. Pale yellow crystals formed slowly. The mixture was then chilled in ice for 2 hours to complete crystallization. Finally, the solid was filtered, washed with cold hexanes (100 mL), and dried in vacuo to afford 83.5 g (58% yield) of methyl 4-bromomethyl-2-hydroxybenzoate (m.p. 73–75° C., open capillary, uncorrected).

$^1$H NMR (300 MHz, CHCl$_3$-d) δ 3.95 (singlet, 3H, OCH$_3$), 4.40 (singlet, 2H, CH$_2$), 6.90 (doublet, J=8 Hz, 1H, ArH), 7.00 (singlet, 1H, ArH), 7.80 (doublet, J=8 Hz, 1H, ArH), 10.78 (singlet, 1H, OH). $^{13}$C NMR (75 MHz, CHCl$_3$d) δ 32.1, 52.5, 112.4, 118.2, 120.1, 130.7, 145.8, 162.0, 170.5.

Methyl 4-(Azidomethyl)-2-hydroxybenzoate

Methyl 4-(bromomethyl)-2-hydroxybenzoate (83.5 g, 341 mmoles) was dissolved in dry N,N-dimethylformamide (150 mL) and sodium azide 25.0 g, 380 mmoles) was added. The yellow suspension was stirred at room temperature, and the solids rapidly dissolved. The solution turned brown, and a precipitate of sodium bromide formed. The reaction mixture was stirred 16 hours, then filtered. The filtrate was evaporated to a brown oil, which was dissolved in a mixture of hexanes and ethyl acetate (1:1 [v/v]. 100 mL). Silica gel (25 g, flash chromatography grade) was added to the brown solution, and the mixture was swirled well. The silica was removed by filtration on a glass frit, and washed three times with hexanes:ethyl acetate (1:1 [v/v], 50 mL portions). The silica gel was dried on the frit, and the combined filtrates were evaporated to dryness to afford a dark yellow liquid. The crude product (which was utilized for the following reaction) was found to contain some residual N,N-dimethylformamide.

$^1$H NMR (300 MHz, CHCl$_3$-d) δ 3.94 (singlet, 3H, OCH$_3$), 4.32 (singlet, 2H, CH$_2$), 6.82 (doublet, J=8 Hz, 1H, ArH), 6.93 (singlet, 1H, ArH), 7.83 (doublet, J=8 Hz, 1H, ArH), 10.80 (singlet, 1H, OH). $^{13}$C NMR (75 MHz, CHCl$_3$, d) δ 52.5, 54.3, 112.3, 117.0, 118.7, 130.8, 143.9, 162.1, 170.5.

Methyl 4-(Aminomethyl)-2-hydroxybenzoate Hydrochloride

Crude methyl 4-(azidomethyl)-2-hydroxybenzoate was dissolved in methanol (750 mL) in a 2 L Parr hydrogenation flask. Palladium on carbon catalyst (10% [w/w], 3.8 g) in water (25 mL) was added, followed by concentrated hydrochloric acid (35 mL). The flask was affixed to a Parr hydrogenator, and the mixture was shaken at room temperature under 40 psi of hydrogen for 16 hours. The reaction mixture was then filtered through a 0.45 mm nylon filter. The retained solid was then washed with methanol (150 mL), water (100 mL), and methanol again (150 mL). The combined filtrates were evaporated to dryness to afford a tan solid. This solid was dissolved in hot denatured ethanol (150 mL) and the solution was allowed to cool to room temperature. White crystals formed quickly. Finally, the mixture was then chilled for 16–18 hours at 4° C. to complete crystallization. The solid was filtered, washed with a little cold ethanol (50 mL) and then diethyl ether (150 mL), and dried in vacuo over potassium hydroxide pellets to afford 51.5 g (65% yield based on methyl 4-bromomethyl-2-hydroxybenzoate) of methyl 4-aminomethyl-2-hydroxybenzoate hydrochloride (m.p. 225–227° C., open capillary, uncorrected).

$^1$H (300 MHz, DMSO-d$_6$) δ 3.87 (singlet, 3H, OCH$_3$), 4.00 (singlet, 2H, CH$_2$), 7.06 (doublet, J=8 Hz, 1H, ArH), 7.13 (singlet, 1H, ArH), 7.77 (doublet, J=8 Hz, 1H, ArH), 8.59 (broad singlet, 3H, NH$_3$Cl), 10.55 (singlet, 1H, OH). $^{13}$C NMR (75 MHz, DMSO-d$_6$)641.6, 52.6, 113.0, 117.7, 119.8, 130.4, 142.1, 160.0, 169.1

Methyl 4-Succinylaminomethyl-2-hydroxybenzoate

Methyl 4-(aminomethyl)-2-hydroxybenzoate hydrochloride (3.00 g, 13.8 mmoles) was suspended in dry pyridine (25 mL), and N,N-diisopropylethylamine (2.7 mL, 15.5 mmoles) was added. The suspension was stirred in an ice/water bath for 15 minutes, and then succinic anhydride (1.36 g, 13.6 mmoles) was added. The mixture was allowed to warm to room temperature, during which time the starting solids dissolved. After stirring for 2 hours, the mixture was evaporated to dryness, and the resulting solid was partitioned between ethyl acetate (300 mL) and 1 M aqueous hydrochloric acid (100 mL). The layers were separated, and the ethyl acetate solution was washed with 1 M hydrochloric acid (100 mL) and saturated aqueous sodium chloride (100 mL). The solution was dried over anhydrous sodium sulfate, filtered, and evaporated to dryness to yield a white solid. Finally, the solid was crystallized from ethyl acetate/hexanes, filtered, and dried in vacuo to afford 3.02 g (87% yield) of methyl 4-succinylaminomethyl-2-hydroxybenzoate (m.p. 161–163° C.).

$^1$H NMR (300 MHz, DMSO-$d_6$) δ 2.43 (triplet, J=6 Hz, 2H, CH$_2$CONH), 2.49 (triplet, J=6 Hz, 2H, HO$_2$CCH$_2$), 3.87 (singlet, 3H, OCH$_3$), 4.27 (doublet, J=6 Hz, 2H, ArCH$_2$NH), 6.83 (doublet, J=8 Hz, 1H, ArH), 6.86 (singlet, 1H, ArH), 7.71 (doublet, J=8 Hz, 1H, ArH), 8.43 (triplet, J=6 Hz, 1H, NH), 10.54 (singlet, 1H, OH), 12.12 (singlet, 1H, CO$_2$H). $^{13}$C NMR (75 MHz, DMSO-$d_6$) δ 29.1, 30.1, 41.9, 52.5, 111.3, 115.6, 118.4, 130.1, 148.7, 160.7, 169.7, 171.7, 174.2.

Methyl 4-Succinylaminomethyl-2-hydroxybenzoate Succinimidyl Ester

Methyl 4-succinylaminomethyl-2-hydroxybenzoate (2.60 g, 10.2 mmoles) was dissolved in dry tetrahydrofuran (100 mL), and N-hydroxysuccinimide (1.29 g, 11.2 mmoles) and 1,3-di-cyclohexylcarbodiimide (2.10 g, 10.2 mmoles) were added. The mixture was stirred at room temperature under dry nitrogen, and the solids rapidly dissolved. After about 20 minutes, a white precipitate formed. The reaction mixture was stirred 16–18 hours, then chilled several hours at −20° C. The mixture was filtered cold, and the solid washed with a little tetrahydrofuran (25 mL). The combined filtrates were evaporated to dryness, and the residue was crystallized from ethyl acetate/hexanes, filtered, and dried in vacuo to afford 2.39 g (62% yield) of methyl 4-succinylaminomethyl-2-hydroxybenzoate succinimidyl ester (m.p. 133–135° C.).

$^1$H NMR (300 MHz, DMSO-d6) δ 2.56 (triplet, J=7 Hz, 2H, CH$_2$CONH), 2.80 (singlet, 4H, COCH$_2$CH$_2$CO), 2.91 (triplet, J=7 Hz, 2H, NO$_2$CCH$_2$), 3.87 (singlet, 3H, OCH$_3$), 4.27 (doublet, J=6 Hz, 2H, ArCH$_2$NH), 6.83 (doublet, J=9 Hz, 1H, ArH), 6.84 (singlet, 1H, ArH), 7.71 (doublet, J=9 Hz, 1H, ArH), 8.51 (triplet, J=6 Hz, 1H, NH), 10.50 (singlet, 1H, OH). $^{13}$C NMR (75 MHz, DMSO-$d_6$) δ 25.4, 25.9, 29.2, 41.8, 52.4, 111.4, 115.6, 118.4, 130.2, 148.2, 160.4, 168.9, 169.4, 170.2, 170.4.

Example VII

Preparation of N-Hydroxysuccinimidyl 4-[N-({4-({cyanomethyl)oxycarbonyl]-3-hydroxyphenyl}methyl)carbamoyl]butanoate

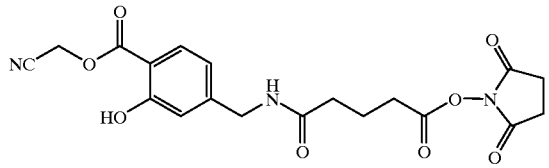

Methyl N-tert-Butoxycarbonylaminomethyl-2-hydroxybenzoate

Methyl 4-aminomethyl-2-hydroxybenzoate hydrochloride (10.9 g, 50 mmoles) was suspended in anhydrous methanol (200 mL) and di-tert-butyldicarbonate (10.9 g, 50 mmoles) and triethylamine (7.0 mL, 50 mmoles) were added. The solid rapidly dissolved with the slow evolution of gas. The reaction mixture was stirred at room temperature for 18 hours under dry nitrogen, then evaporated to dryness to afford a white amorphous mass. This mass was partitioned between ethyl acetate (200 mL) and water (100 mL). The layers were separated, and the ethyl acetate solution was dried over anhydrous sodium sulfate. The solution was filtered and evaporated to a white solid. This solid was crystallized from ethyl acetate/hexanes, filtered, and dried in vacuo to afford 13.7 g (97% yield) of methyl N-tert-butoxycarbonylaminomethyl—2-hydroxybenzoate (m.p. 95–96° C., open capillary, uncorrected).

$^1$H NMR (300 MHz, CHCl$_3$-d) δ 1.42 (singlet, 9H, C(CH$_3$)$_3$), 3.90 (singlet, 3H, OCH$_3$), 4.26 (doublet, J=6 Hz, 2H, CH$_2$Ar), 4.99 (triplet, J=6H, 1H, NH), 6.75 (doublet, J=8 Hz, 1H, ArH), 6.84 (singlet, 1H, ArH), 7.73 (doublet, J=8 Hz, 1H, ArH), 10.72 (singlet, 1H, OH). $^{13}$C NMR (75 MHz, CHCl$_3$-d) δ 28.5, 44.4, 52.4, 80.0, 111.5, 115.9, 118.2, 130.5, 150.0, 156.3, 162.1, 170.8.

N-tert-Butoxycarbonylaminomethyl-2-hydroxybenzoic Acid

Methyl N-tert-butoxycarbonylaminomethyl-2-hydroxybenzoate (8.7 g, 30.9 mmoles) was dissolved in dry tetrahydrofuran (100 mL), and potassium trimethylsilanolate (4.4 g, 30.9 mmoles, 90% pure) was added. The yellow solution was refluxed for 24 hours, during which time a tan precipitate formed and the solvent turned light brown. The mixture was evaporated to dryness, and the solid was dissolved in cold water (100 mL). The brown solution was chilled in an ice bath, and saturated aqueous potassium hydrogen sulfate solution was used to titrate the stirred solution to pH 2–3. An off-white solid precipitated during the titration. The solid was filtered, washed with cold water, and dried in vacuo over potassium hydroxide to afford 6.7 g, (81% yield) of crude N-tert-butoxycarbonylaminomethyl-2-hydroxybenzoic acid (m.p. 141–144° C., decomposes with effervescence on melting, open capillary, uncorrected).

$^1$H NMR (300 MHz, CHCl$_3$-d) δ 1.47 (singlet, 9H, C(CH$_3$)$_3$), 4.33 (doublet, J=6 Hz, 2H, CH$_2$Ar), 5.07 (triplet, J=6H, 1H, NH), 6.80 (doublet, J=8 Hz, 1H, ArH), 6.88 (singlet, 1H, ArH), 7.81 (doublet, J=8 Hz, 1H, ArH), 10.72 (broad singlet, 2H, OH and CO$_2$H). $^{13}$C NMR (75 MHz, CHCl$_3$-d) δ 28.5, 44.4, 80.5, 111.1, 115.9, 118.3, 131.5, 148.5, 156.6, 162.6, 174.1.

Cyanomethyl N-tert-Butoxycarbonylaminomethyl-2-hydroxybenzoate

N-tert-Butoxycarbonylamino-methyl-2-hydroxybenzoic acid (8.2 g, 30.6 mmoles) was suspended in chloroacetonitrile (25 mL), and triethylamine (4.3 mL, 30.6 mmoles) was added. The mixture was stirred under dry nitrogen at 50° C., and the solids dissolved. The solution was stirred 18 hours, and then cooled to room temperature. The solvent was evaporated, and the residue was partitioned between ethyl acetate (250 mL) and water (250 mL). The layers were separated, and the ethyl acetate layer was washed with saturated aqueous sodium bicarbonate (100 mL) and saturated aqueous sodium chloride (100 mL). The solution was dried over anhydrous sodium sulfate, filtered, and evaporated to dryness. The residual pale tan solid was dissolved in ethyl acetate (100 mL), and silica gel (10 g, flash chromatography grade) was added. The mixture was swirled well and allowed to sit for five minutes at room temperature. The silica was removed by filtration on a grlass frit, and washed with ethyl acetate (100 mL). The filtrate was evaporated to dryness. The solid residue was crystallized from ethyl acetate/hexanes to afford 7.9 g (88% yield) of cyanomethyl N-tert-butoxycarbonylaminomethyl- 2-hydroxybenzoate (m.p. 144–146° C., open capillary, uncorrected).

$^1$H NMR (300 MHz, CHCl$_3$-d) δ 1.45 (singlet, 9H, C(CH$_3$)$_3$), 4.30 (doublet, J=6 Hz, 2H, CH$_2$Ar), 5.00 (singlet, 2H, OCH$_2$CN), 5.05 (triplet, J=6H, 1H, NH), 6.83 (doublet, J=8 Hz, 1H, ArH), 6.91 (singet, 1H, ArH), 7.77 (doublet, J=8 Hz, 1H, ArH), 10.12 (singlet, 1H, OH). $^{13}$C NMR (75 MHz, CHCl$_3$-d) δ 28.4, 44.3, 49.0, 80.1, 109.6, 114.2, 116.1, 118.7, 130.5, 149.7, 156.2, 162.5, 168.5.

Cyanomethyl 4-Aminomethyl-2-hydroxybenzoate Hydrochloride

Cyanomethyl N-tert-butoxycarbonylaminomethyl-2-hydroxybenzoate (7.7 g, 26.2 mmoles) was dissolved in tetrahydrofuran (150 mL), and dry hydrogen chloride was bubbled slowly through the solution. The reaction mixture warmed as the gas dissolved. After 5 minutes, the gas was shut off, and the solution was stirred at room temperature. A thick, creamy white precipitate formed in the solution. After 30 minutes, the reaction mixture was chilled in ice for 2 hours, then the solid was filtered, washed with diethyl ether (100 mL) and dried in vacuo over potassium hydroxide pellets to afford 5.8 g (91% yield) of cyanomethyl aminomethyl-2-hydroxybenzoate hydrochloride (m.p. darkens at 210° C., decomposes at 228° C., open capillary, uncorrected).

$^1$H NMR (300 MHz, DMSO-d6) δ 4.00 (singlet, 2H, CH$_2$Ar), 5.20 (singlet, 2H, OCH$_2$CN), 7.05 (doublet, J=8 Hz, 1H, ArH), 7.15 (singlet, 1H, ArH), 7.75 (doublet, J=8 Hz, 1H, ArH), 8.62 (broad singlet, 3H, NH$_3$), 10.38 (singlet, 1H, OH). $^{13}$C NMR (75MHz,DMSO-d6) δ 41.6, 49.7, 113.0, 116.1, 118.0, 119.7, 131.1, 142.3, 159.5, 166.1.

Cyanomethyl 4-Glutarylaminomethyl-2-hydroxybenzoate

Cyanomethyl 4-aminomethyl-2-hydroxybenzoate hydrochloride (1.22 g, 5.0 mmoles) was suspended in dry dichloromethane (100 mL), and the suspension was stirred in an ice/water bath. A solution of glutaric anhydride (0.57 g, 5.0 mmoles) and triethylamine (0.7 mL, 5.0 mmoles) in dry dichloromethane (25 mL) was then added dropwise over 15 minutes. The mixture was allowed to warm to room temperature, and the reaction was stirred for 18 hours. The mixture was evaporated to dryness, and the resulting solid was triturated under cold 0.1 M aqueous hydrochloric acid (50 mL). The solid was collected by filtration, washed with cold water, and dried in vacuo over potassium hydroxide pellets to afford 1.43 g (89% yield) of cyanomethyl 4-glutarylaminomethyl-2-hydroxybenzoate (m.p. 125–126° C.).

$^1$H NMR (300 MHz, DMSO-d$_6$) δ 1.75 (quintet, J=7 Hz, 2H, CH$_2$CH$_2$CH$_2$), 2.19 (triplet, J=7 Hz, 2H, CH$_2$CONH), 2.22 (triplet, J=7 Hz, 2H, HO$_2$CCH$_2$), 4.24 (doublet, J=6 Hz, 2H, ArCH$_2$NH), 5.17 (singlet, 2H, OCH$_2$CN), 6.81 (doublet, J=8 Hz, 1H, ArH), 6.85 (singlet, 1H, ArH), 7.70 (doublet, J=8 Hz, 1H, ArH), 8.39 (triplet, J=6 Hz, 1H, NH), 10.5 (very broad singlet, 1H, OH), 11.7 (very broad singlet, 1H, CO$_2$H). $^{13}$C NMR (75 MHz, DMSO-d$_6$) δ 20.7, 33.1, 34.5, 41.8, 49.7, 111.2, 115.9, 116.2, 118.5, 130.9, 149.1, 160.2, 166.6, 172.3, 174.5.

Cyanomethyl 4-Glutarylaminomethy-2-hydroxybenzoate Succinimidyl Ester

Cyanomethyl 4-glutarylaminomethyl-2-hydroxybenzoate (1.00 g, 3.1 mmoles) was dissolved in dry tetrahydrofuran (50 mL), and N-hydroxysuccinimide (0.36 g, 3.1 mmoles) and 1,3-dicyclohexylcarbodiimide (0.64 g, 3.1 mmoles) were added. The mixture was stirred at room temperature under dry nitrogen, and the solids rapidly dissolved. After about 60 minutes, a white precipitate formed. The reaction mixture was stirred 24 hours, then chilled several hours at −20° C. The mixture was filtered cold, and the solid washed with a little tetrahydrofuran (10 mL). The combined filtrates were evaporated to dryness, and the residue was crystallized from ethyl acetate/hexanes, filtered, and dried in vacuo to afford 1.04 g (80% yield) of cyanomethyl 4-glutarylaminomethyl-2-hydroxybenzoate succinimidyl ester (m.p. 116–119° C.).

$^1$H NMR (300 MHz, DMSO-d$_6$) δ 1.88 (quintet, J=7 Hz, 2H, CH$_2$CH$_2$CH$_2$), 2.30 (triplet, J=7 Hz, 2H, CH$_2$CONH), 2.71 (triplet, J=7 Hz, 2H, NO$_2$CCH$_2$), 2.80 (singlet, 4H, COCH$_2$CH$_2$CO), 4.26 (doublet, J=6 Hz, 2H, ArCH$_2$NH), 5.18 (singlet, 2H, OCH$_2$CN), 6.82 (doublet, J=8 Hz, 1H, ArH), 6.86 (singlet, 1H, ArH), 7.71 (doublet, J=8 Hz, 1H, ArH), 8.44 (triplet, J=6 Hz, 1H, NH), 10.18 (broad singlet, 1H, OH). $^{13}$C NMR (75 MHz, DMSO-d$_6$) δ 20.4, 25.5, 29.7, 33.6, 41.8, 49.6, 111.2, 115.9, 116.2, 118.4, 130.9, 148.9, 160.1, 166.5, 169.0, 170.5, 171.7.

Example VIII

Preparation of N-Hydroxysuccinimidyl 4-(N-{[3,5-dihydroxy-4-(methoxycarbonyl)phenyl] methyl}carbamoyl)butanoate

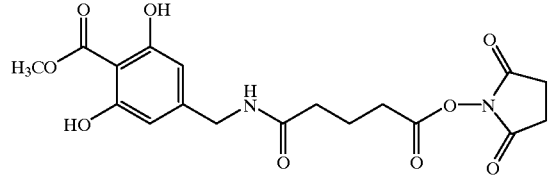

Methyl 4-glutarylaminomethyl-2,6-dihydroxybenzoate

Glutaric anhydride (2.3 grams, 20 mmoles) was dissolved in dry tetrahydrofuran (100 mL), and the suspension was stirred under nitrogen. N,N-diisopropylethylamine (7.0 mL, 40 mmoles) was added, followed by methyl 4-aminomethyl-2,6-dihydroxybenzoate hydrochloride (4.7 grams, 20 mmoles). After stirring for 18 hours, the mixture was evaporated to dryness, and the resulting solid was dissolved in dichloromethane (100 mL) and allowed to sit at room temperature for 2 hours. The dichloromethane solution was evaporated to dryness to give a thick syrup, which was treated with cold 1 M aqueous hydrochloric acid (100 mL) for 30 minutes in ice. An off-white solid precipitated, which was filtered, washed with cold water, and dried in vacuo to afford 5.5 grams (88% yield) of methyl 4-glutarylaminomethyl-2,6-dihydroxybenzoate (m.p. 163–164° C.).

$^1$H (300 MHz, DMSO-d$_6$) δ 1.74 (quintet, J=8 Hz, 2H, CH$_2$CH$_2$CH$_2$), 2.16 (triplet, J=8 Hz, 2H, CH$_2$CONH), 2.20 (triplet, J=8 Hz, 2H, HO$_2$CCH$_2$), 3.78 (singlet, 3H, OCH$_3$), 4.10 (doublet, J=6 Hz, 2H, ArCH$_2$NH), 6.23 (singlet, 2H, ArH), 8.31 (triplet, J=6 Hz, 1H, NH), 10.05 (broad singlet, 3H, OH and CO$_2$H). $^{13}$C NMR (75 MHz, DMSO-d$_6$) δ 20.7, 33.1, 34.4, 41.8, 52.1, 104.4, 105.6, 145.7, 158.2, 169.0, 172.0, 174.5.

Methyl 4-Glutarylaminomethyl-2,6-dihydroxybenzoate Succinimidyl Ester Methyl 4-glutarylaminomethyl-2,6-dihydroxybenzoate (2.0 grams, 6.4 mmoles) was dissolved in dry tetrahydrofuran (80 mL), and N-hydroxysuccinimide (0.8 grams, 7.0 mmoles) and 1,3-dicyclohexylcarbodiimide (1.3 grams, 6.4 mmoles) were added. The mixture was stirred at room temperature under dry nitrogen, and the solids rapidly dissolved. After about 20 minutes, a white precipitate formed. The reaction mixture was stirred 16–18 hours, then chilled several hours at −20° C. The mixture was filtered cold, and the solid washed with a little tetrahydrofuran (25 mL). The combined filtrates were evaporated to dryness, and the residue was crushed under ice-cold water (25 mL). The solid was filtered, washed quickly with cold water (25 mL) and then diethyl ether (100 mL), and dried in vacuo. The solid was recrystallized from ethyl acetate/hexanes to afford 2.5 grams (95% yield) of methyl 4-glutarylaminomethyl-2,6-dihydroxy-benzoate succinimidyl ester (m.p. 161–1630C).

¹H NMR (300 MHz, DMSO-d₆) δ 1.83 (quintet, J=8 Hz, 2H, CH₂CH₂CH₂), 2.26 (triplet, J=8 Hz, 2H, CH₂CONH), 2.73 (triplet, J=8 Hz, 2H, NO₂CCH₂), 2.80 (singlet, 4H, COCH₂CH₂CO), 3.77 (singlet, 3H, OCH₃), 4.10 (doublet, J=6 Hz, 2H, ArCH₂NH), 6.24 (singlet, 2H, ArH), 8.35 (triplet, J=6 Hz, 1H, NH), 10.04 (broad singlet, 2H, OH).
¹³C NMR (75 MHz, DMSO-d₆) δ 20.4, 25.4, 29.7, 33.6, 41.8, 52.0, 104.5, 105.6, 145.5, 158.1, 168.9, 170.5, 171.4.

Example IX

Preparation of Methyl 2-Hydroxy-4-[({[3-hydroxy-4-(methoxycarbonyl)-phenyl]methyl}amino)methyl] benzoate Hydrochloride

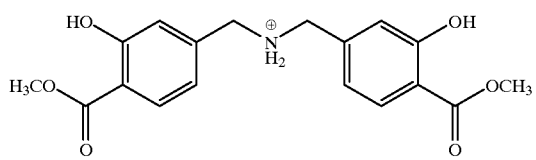

Dissolved methyl 4-aminomethyl-2-hydroxybenzoate hydrochloride (13.07 g, 60.1 mmole) and diisopropylethylamine (28.0 mL, 292 mmole) in 225 mL of N,N-dimethylformamide by heating slightly until a solution was obtained. Allowed the solution to cool to room temperature and added methyl 4-bromomethyl-2-hydroxybenzoate (9.81 g, 40.0 mmole). The reaction was stirred for 1 day at room temperature. The solution was diluted with 200 mL of 1N HCl and 250 mL of ethyl acetate and allowed to cool to room temperature. Precipitate was collected by filtration, washed with ethyl acetate and dried in vacuo under a under high vacuum. Obtained 11.32 grams (74% yield) of product as a white solid.

¹H NMR (300 MHz, DMSO-d₆) 3.88 (singlet, 6H, OCH₃), 4.15 (singlet, 4H, NH₂CH₂Ar), 7.08 (doublet, J=8 Hz, 2H, ArH), 7.17 (singlet, 2H, ArH), 7.80 (doublet, J=8 Hz, 2H, ArH), 9.72 (broad singlet, 2H, NH₂), 10.53 (singlet, 2H, ArH).

Example X

Preparation of Methyl 4-[((tert-butoxy)-N-{[3-hydroxy-4-(methoxycarbonyl)-phenyl] methyl}carbonylamino)methyl]-2-hydroxybenzoate

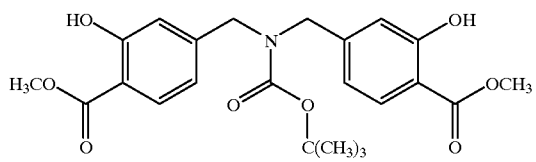

Suspended methyl 2-hydroxy-4-[({[3-hydroxy-4-(methoxycarbonyl)phenyl]-methyl}amino)methyl]benzoate hydrochloride salt (8.89 g, 23.3 mmole) in 250 mL of methanol and added triethylenediamine (6.50 mL, 46.6 mmole). Stirred until the solution was homogenous. Added di-tert-butyldicarbonate and stirred overnight. Removed methanol in vacuo. Passed the material through a large plug of silica gel using 30% ethyl acetate in hexane as eluent. Collected the first UV active material that eluted from the silica. Removed solvents in vacuo and collected 10.59 grams (100% yield) of the protected product.

¹H NMR (300 MHz, DMSO-d₆) 1.34 (singlet, 9H, C(CH₃)₃), 3.86 (singlet, 6H, OCH₃), 4.34 (singlet, 2H, NH₂CH₂Ar), 4.40 (singlet, 2H, NH₂CH₂Ar), 6.79 (broad singlet, 4H, ArH), 7.73 (doublet, J=8 Hz, 2H, ArH), 10.50 (singlet, 2H, ArH).

Example XI

Preparation of Methyl 4-[(((tert-butoxy)-N-{[4-(methoxycarbonyl)-3-(phenylmethoxy)-phenyl] methyl}carbonylamino)methyl]-2-(phenylmethoxy) benzoate

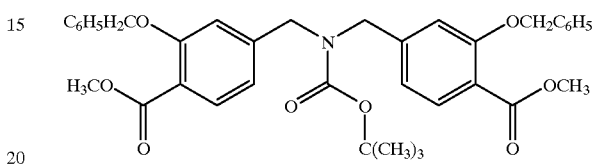

Dissolved methyl 4-[((tert-butoxy)-N-{[3-hydroxy-4-(methoxycarbonyl)phenyl]-methyl}carbonylamino) methyl]-2-hydroxybenzoate (6.86 g, 15.4 mmole) in 125 mL of acetone and added benzyl bromide (3.95 mL, 33.2 mmole) followed by potassium carbonate (10.64 g, 76.98 mmole). Heated to reflux and stirred for 16 hours. Filtered away the solids and removed solvent in vauco. Chromatographed the crude material through a large column of silica gel and collected 9.44 grams (98% yield) of the benzyl-protected product.

¹H NMR (300 MHz, DMSO-d₆) 1.35 (singlet, 9H, C(CH₃)₃), 3.75 (singlet, 6H, OCH₃), 4.33 (singlet, 2H, NH₂CH₂Ar), 4.41 (singlet, 2H, NH₂CH₂Ar), 5.08 (singlet, 4H, ArCH₂OAr), 6.93 (multiplet, 4H, ArH), 7.37 (multiplet, 10H, ArH), 7.66 (doublet, J=8 Hz, 2H, ArH).

Example XII

Preparation of Methyl 4-[({[4-(methoxycarbonyl)-3-(phenylmethoxy)phenyl]-methyl}amino)methyl]-2-(phenylmethoxy)benzoate Hydrochloride

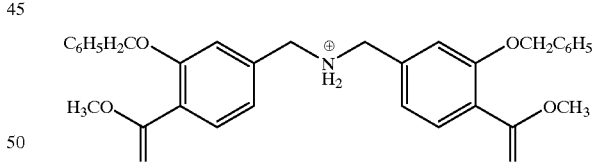

Dissolved the methyl 4-[(((tert-butoxy)-N-{[4-(methoxycarbonyl)-3-(phenylmethoxy)phenyl] methyl}carbonylamino)methyl]-2-(phenylmethoxy) benzoate (9.44 g, 15.1 mmole) into 150 mL of ethyl acetate and bubbled HCl gas through the solution for 15 minutes. Let cool the room temperature and stirred for 1 hour. Removed solvent in vacuo. Dried the oil in vacuo under a high vacuum with NaOH pellets and obtained a crude foam. The material was taken on without further purification.

¹H NMR (300 MHz, DMSO-d₆) 3.78 (singlet, 6H, OCH₃), 4.17 (singlet, 4H, NH₂CH₂Ar), 5.22 (singlet, 4H, ArCH₂OAr), 7.17 (doublet, J=8 Hz, 2H, ArH), 7.48 (multiplet, 14H, ArH), 10.17 (broad singlet, 2H, NH₂).

Example XIII

Preparation of Methyl 4-[(N-{[4-(methoxycarbonyl)-3-(phenylmethoxy)phenyl]methyl}-6-[(phenylmethoxy)carbonylamino]hexanoylamino)methyl]-2-(phenylmethoxy)benzoate

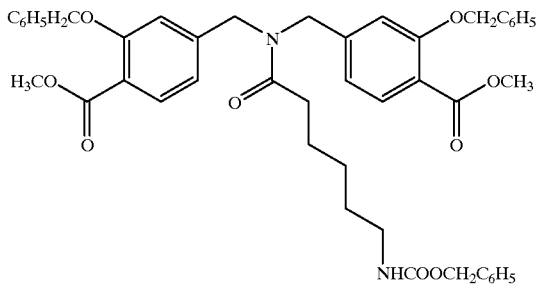

Dissolved N-Cbz-6-aminohexanoic acid (784 mg, 2.96 mmole) into 10 mL of N,N-dimethylformamide and cooled to 0° C. Added triethylamine (1.65 mL, 11.8 mmole), stirred for 10 minutes, then added isobutylchloroformate (385 uL, 2.68 mmole). Stirred for 45 minutes and then added the crude methyl 4-[({[4-(methoxycarbonyl)-3-(phenylmethoxy)phenyl]methyl}-amino)-methyl]-2-(phenylmethoxy)benzoate hydrochloride from the step above (830 mg, 1.48 mmole). Let warm to room temperature and stirred for 3 hours. Diluted the reaction mixture with 1 N HCl and extracted with ethyl acetate. Dried the ethyl acetate layers with brine and anhydrous magnesium sulfate. Filtered, removed solvents in vacuo, and chromatographed on silica gel. Collected 870 mg (76% yield) of product.

$^1$H NMR (300 MHz, DMSO-$d_6$) 1.20 (multiplet, 2H, $CH_2CH_2CH_2$), 1.36 (multiplet, 2H, $CH_2CH_2CH_2$), 1.50 (multiplet, 2H, $CH_2CH_2CH_2$), 2.28 (triplet, J=7.3 Hz, 2H, $COCH_2$), 2.94 (quartet, J=6.4 Hz, 2H, $CONHCH_2$), 3.75 (singlet, 3H, $CO_2CH_3$), 3.76 (singlet, 3H, $CO_2CH_3$), 4.50 (singlet, 2H, $ArCH_2N$), 4.53 (singlet, 2H, $ArCH_2N$), 4.97 (singlet, 2H, $ArCH_2CO_2$), 5.09 (singlet, 2H, $ArCH_2OAr$), 5.12 (singlet, 2H, $ArCH_2OAr$), 6.81 (doublet, J=7.9 Hz, 1H, ArH), 6.86 (doublet, J=7.9 Hz, 1H, ArH), 6.91 (singlet, 1H, ArH), 7.01 (singlet, 1H, ArH), 7.20 (triplet, J=6.4 Hz, 1H, $CO_2NH$), 7.36 (multiplet, 15H, ArH), 7.64 (doublet, J=7.9 Hz, 1H, ArH), 7.67 (doublet, J=7.9 Hz, 1H, ArH).

Example XIV

Preparation of Methyl 4-[(6-amino-N-{[3-hydroxy-4-(methoxycarbonyl)-phenyl]methyl}hexanoylamino)methyl]-2-hydroxybenzoate

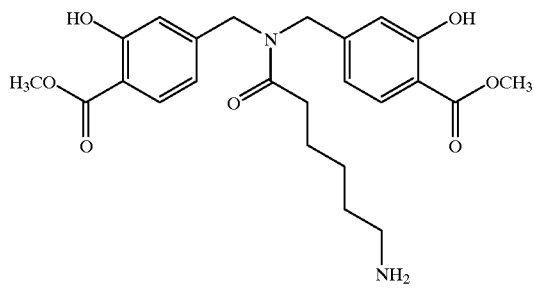

Dissolved methyl 4-[(N-{[4-(methoxycarbonyl)-3-(phenylmethoxy)phenyl]-methyl}-6-[(phenylmethoxy)carbonylamino]hexanoylamino)methyl]-2-(phenylmethoxy)-benzoate (1.20 g, 1.56 mmole) in 400 mL of methanol and then added conc. HCl (400 uL) and a small scoop of palladium on carbon (10%). Hydrogenated for 4 hours using a Parr shaker at 40 psi. Filtered away the palladium on carbon and removed the methanol in vacuo. Collected 730 mg (95% yield) of the product as the hydrochloride salt.

$^1$H NMR (300 MHz, DMSO-$d_6$) 1.27 (multiplet, 2H, $CH_2CH_2CH_2$), 1.51 (multiplet, 4H, $CH_2CH_2CH_2CH_2$), 2.34 (triplet, J=7.3 Hz, 2H, $COCH_2$), 2.71 (multiplet, 2H, $NH_3CH_2$), 3.87 (singlet, 6H, $CO_2CH_3$), 4.50 (singlet, 2H, $ArCH_2N$), 4.57 (singlet, 2H, $ArCH_2N$), 6.76 (multiplet, 4H, ArH), 7.71 (doublet, J=7.9 Hz, 1H, ArH), 7.75 (doublet, J=7.9 Hz, 1H, ArH), 7.91 (broad singlet, 3H, $CH_2NH_3$), 10.51 (broad singlet, 2H, ArOH).

Example XV

Preparation of Cyanomethyl 4-{[2-(3-[(tert-Butoxy)carbonylamino]-N-{[N-({ 4-[(cyanomethyl)oxycarbonyl]-3-hydroxyphenyl}methyl)carbamoyl]methyl}-propanoylamino)acetylamino]methyl}-2-hydroxybenzoate

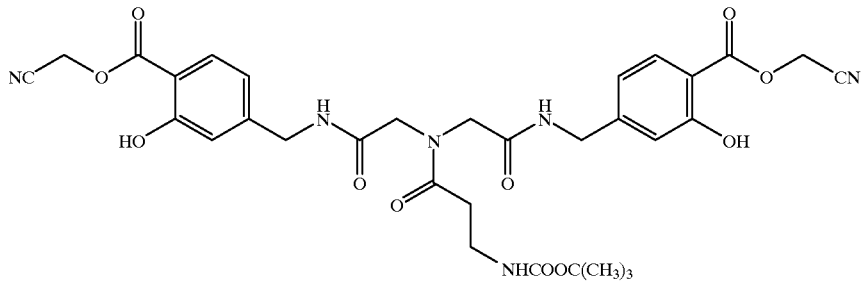

To a solution of 2-{3-[(tert-butoxy)carbonylamino]-N-(carboxymethyl)-propanoylamino}acetic acid (1.87 g, 6.15 mmole) in 40 mL of N,N-dimethylformamide (DMF) was added N-hydroxysuccinimide (1.53 g, 13.3 mmole) and 1,3-dicyclohexylcarbodiimide (2.66 g, 12.9 mmole). The reaction was stirred for 8 hours at room temperature. To the solution was added disiopropylethylamine (2.70 mL, 28.2 mmole) and cyanomethyl 4-aminomethyl-2-hydroxybenzoate hydrochloride (3.14 g, 12.9 mmole), and the reaction is stirred for 16 hours at room temperature. The solution has diluted with ethyl acetate and extracted with 1N HCl and brine. The organic phase was dried over anhydrous magnesium sulfate and the solvent removed in vacuo to afford crude product.

Example XVI

Preparation of Cyanomethyl 4-{[2-(3-Amino-N-[N-({4-[(cyanomethyl)oxycarbonyl]-3-hydroxyphenyl}methyl)carbamoyl]methyl}propanoylamino)acetylamino]methyl}-2-hydroxybenzoate (9Y-SA(OCH$_2$CN)-β-Ala-amine)

The crude Cyanomethyl 4-{ [2-(3-[(tert-Butoxy)carbonylamino]-N-{ [N-({4-[(cyanomethyl) oxycarbonyl]-3-hydroxyphenyl}methyl) carbamoyl]methyl}propanoylamino)acetylamino]methyl)-2-hydroxybenzoate from above was dissolved in 20 mL of dichloroethane and 10 mL of trifluoroacetic acid (26.0 mmole) was added. The deprotection reaction was stirred for 2 hours at room temperature. Dichloroethane and trifluoroacetic acid were removed in vacuo. The resulting oil was dissolved in 10 mL of ethyl acetate, and the resulting solution was added dropwise to 150 mL of rapidly stirred methyl tert-butyl ether. The product precipitated over the course of one hour and was collected by filtration, washed with methyl tert-butyl ether and dried in vacuo under a high vacuum. Obtained 2.78 grams (65% for two steps) of product as a white solid.

$^1$H NMR (300 MHz, DMSO-d$_6$) 2.64 (triplet, J=7 Hz, 2H, NCH$_2$CH$_2$N$_2$), 2.98 (multiplet, 2H, NCH$_2$CH$_2$NH$_2$), 4.03 (singlet, 2H, COCH$_2$N), 4.19 (singlet, 2H, COCH$_2$N), 4.28 (doublet, J=6 Hz, 2H, ArCH$_2$NH), 4.32 (doublet, J=6 Hz, 2H, ArCH$_2$NH), 5.19 (singlet, 4H, OCH$_2$CN), 6.81 (doublet, J=8 Hz, 2H, ArH), 6.86 (singlet, 1H, ArH), 6.89 (singlet, 1H, ArH), 7.72 (multiplet, 4H, CH$_2$NH$_2$, ArH), 8.75 (triplet, J=6 Hz, 1H, NHCO), 9.14 (triplet, J=6 Hz, 1H, NHCO), 10.21 (singlet, 2H, ArOH).

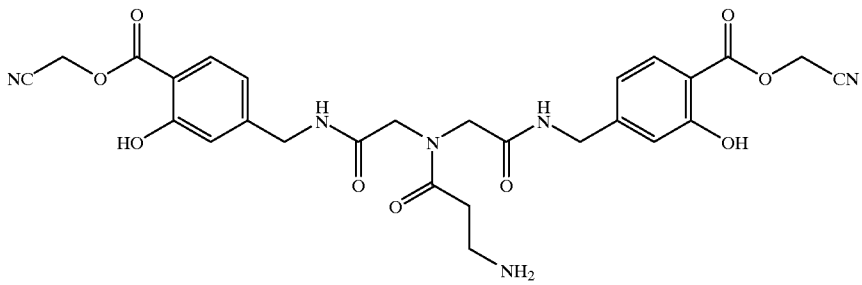

Example XVII

Preparation of Methyl 4-[(2-{N-[(N-{(3,5-dihydroxy-4-(methoxycarbonyl)phenyl]-methyl}carbamoyl)methyl]-6-[(tert-butoxy) carbonylamino]hexanoylamino}acetylamino) methyl]-2,6-dihydroxybenzoate

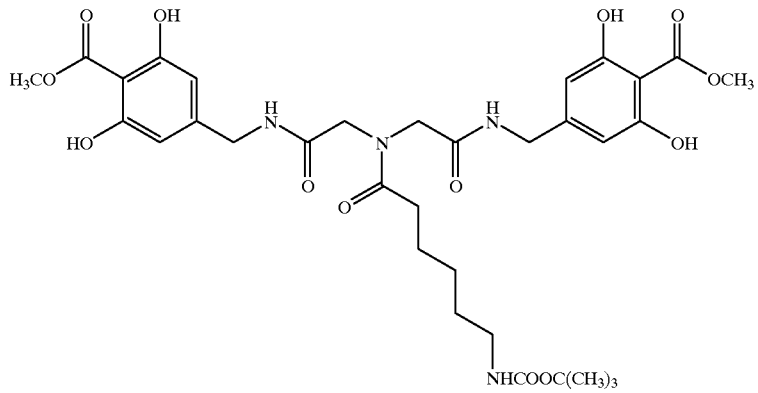

To a solution of 2-{6-[(tert-butoxy)carbonylamino]-N-(carboxymethyl)hexanoyl-amino}acetic acid (1.91 g, 5.51 mmole) in 25 mL of N,N-dimethylformamide (DMF) was added N-hydroxysuccinimide (1.31 g, 11.4 mmole) and 1,3-dicyclohexylcarbodiimide (2.28 g, 11.1 mmole). The reaction was stirred for 16 hours at room temperature. A solution containing methyl 4-(aminomethyl)-2,6-dihydroxybenzoic acid hydrochloride ((2.58 g, 11.0 mmole) and disiopropylethylamine (1.60 mL, 9.19 mmole) in 30 mL of DMF was added, and the reaction is stirred for 8 hours at room temperature. Solids were removed by filtration, and the solution has diluted with ethyl acetate (250 mL) and then extracted with 1N HCl (100 mL) and brine (100 mL). The organic phase was dried over anhydrous magnesium sulfate and the product precipitated by addition of hexane. Obtained 2.41 grams (62% yield) of product.

$^1$H NMR (300 MHz, DMSO-d6) 1.17 (multiplet, 2H, $CH_2$), 1.31 (multiplet, 2H, $CH_2$), 1.34 (singlet, 9H, BOC), 1.43 (multiplet, 2H, $CH_2$), 2.18 (triplet, J=7.3 Hz, 2H, $CH_2CONR_2$), 2.84 (quartet, J=6.0 Hz, 2H, $CH_2NHBOC$), 3.78 (singlet, 6H, $CO_2CH_3$), 3.96 (singlet, 2H, $NCH_2CO$), 4.09 (singlet, 2H, $NCH_2CO$), 4.13 (doublet, J=5.7 Hz, 2H, $ArCH_2N$), 4.15 (doublet, J=5.7 Hz, 2H, $ArCH_2N$), 6.26 (singlet, 4H, ArH), 6.69 (triplet, J=5.4 Hz, 1H, NHBOC), 8.62 (triplet, J=5.9 Hz, 1H, $ArCH_2NH$), 9.11 (triplet, J=6.0 Hz, 1H, $ArCH_2NH$), 10.06 (singlet, 4H, ArOH).

Example XVIII

Preparation of Methyl 4-[(2-{6-Amino-N-[(N-{[3,5-dihydroxy-4-(methoxycarbonyl)-phenyl]methyl}carbamoyl)methyl]hexanoylamino}acetylamino)methyl]-2,6-dihydroxybenzoate (9Y-DHBA(OCH$_3$)-Hexanoylamine)

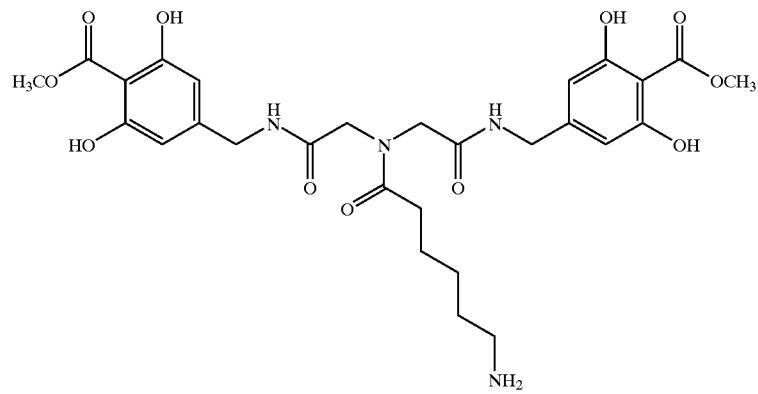

The methyl 4-[(2-{N-[(N-{(3,5-dihydroxy-4-(methoxycarbonyl)phenyl]methyl}-carbamoyl)methyl]-6-[(tert-butoxy)carbonylamino]hexanoylamino}acetylamino)methyl]-2,6-dihydroxybenzoate (2.31 g, 3.28 mmole) was suspended in 10 mL of dichloroethane and 2 mL of trifluoroacetic acid (26.0 mmole) was added. The deprotection reaction was stirred for 3 hours at room temperature. Dichloroethane and trifluoroacetic acid were removed in vacuo, and the resulting residue was dissolved in 20 mL of methanol, and the product precipitated by addition of ethyl ether. The product was collected by filtration, waashed with ethyl acetate and dried in vacuo under a high vacuum. Obtained 2.24 grams (97% yield) of product as the trifluoroacetate salt.

$^1$H NMR (300 MHz, DMSO-d6) 1.22 (multiplet, 2H, CH$_2$), 1.47 (multiplet, 4H, CH$_2$), 2.20 (triplet, J=7.0 Hz, 2H, CH$_2$CONR$_2$), 2.73 (quartet, J=6.7 Hz, 2H, CH$_2$NHBOC), 3.79 (singlet, 6H, CO$_2$CH$_3$), 3.96 (singlet, 2H, NCH$_2$CO), 4.11 (singlet, 2H, NCH$_2$CO), 4.13 (doublet, J=5.7 Hz, 2H, ArCH$_2$N), 4.15 (doublet, J=5.7 Hz, 2H, ArCH$_2$N), 6.27 (singlet, 4H, ArH), 7.75 (broad singlet, 3H, NH$_3$), 8.67 (triplet, J=5.9 Hz, 1H, ArCH$_2$NH), 9.18 (triplet, J=5.9 Hz, 1H, ArCH$_2$NH), 10.11 (singlet, 4H, ArOH).

Example XIX

Preparation of Methyl 4-[(2-{4-{N-[(tert-butyloxy)carbonylamino]carbamoyl}-N-[(N-{[3-hydroxy-4-(methoxycarbonyl)phenyl]methyl}carbamoyl)methyl]butanoylamino}-acetylamino)methyl]-2-hydroxybenzoate

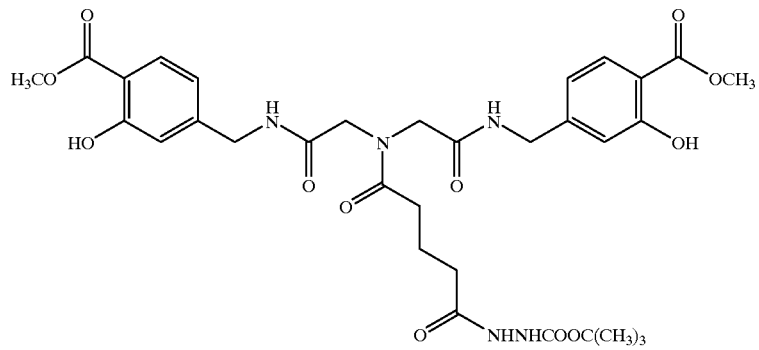

To a solution of 2-(4-{N-[(tert-butoxy)carbonylamino]carbamoyl}-N-(carboxymethyl)butanoylamino)acetic acid (1.66 g, 4.59 mmole) in 20 mL of N,N-dimethylformamide (DMF) was added N-hydroxysuccinimide (1.10 g, 9.56 mmole) and 1,3-dicyclohexylcarbodiimide (1.90 g, 9.21 mmole). The reaction was stirred overnight at room temperature. A solution containing methyl 4-aminomethyl-2-hydroxybenzoic acid hydrochloride (2.00 g, 9.19 mmole) and disiopropylethylamine (1.60 mL, 9.19 mmole) in 25 mL of DMF was added, and the reaction is stirred for 8 hours at room temperature. The solution has diluted with ethyl acetate (250 mL) and then extracted with 1N HCl (2×100 mL) and brine (100 mL). The organic phase was dried over anhydrous magnesium sulfate and the product precipitated by addition of hexane. Obtained 2.00 grams (63% yield) of product as a white powder. $^1$H NMR (300 MHz, DMSO-d$_6$) 1.37 (singlet, 9H, C(CH$_3$)$_3$), 1.71 (pentet, J=7 Hz, 2H, COCH$_2$CH$_2$CH$_2$CO), 2.07 (triplet, J=7 Hz, 2H, COCH$_2$CH$_2$CH$_2$CO), 2.28 (triplet, J=7 Hz, 2H, COCH$_2$CH$_2$CH$_2$CO), 3.86 (singlet, 6H, OCH$_3$), 4.00 (singlet, 2H, COCH$_2$N), 4.17 (singlet, 2H, COCH$_2$N), 4.28 (doublet, J=6 Hz, 2H, ArCH$_2$N), 4.32 (doublet, J=6 Hz, 2H, ArCH$_2$N), 6.81 (doublet, J=8 Hz, 2H, ArH), 6.85 (singlet, 2H, ArH), 7.69 (doublet, J=8 Hz, 1H, ArH), 7.70 (doublet, J=8 Hz, 1H, ArH), 8.64 (singlet, 1H, NHNHBOC), 8.75 (triplet, J=6 Hz, 1H, NHCO), 9.20 (triplet, J=6 Hz, 1H, NHCO), 9.46 (singlet, 1H, NHNHBOC), 10.51 (singlet, 2H, ArOH).

Example XX

Preparation of N,N-bis-({N-[(4-(N-hydroxycarbamoyl)-3-hydroxyphenyl)methyl]-carbamoyl}methyl)-N'-[(tert-butoxy)carbonylamino]pentane-1,5-diamide

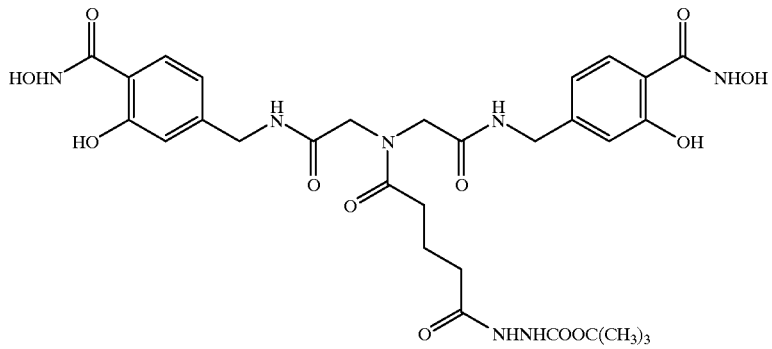

To 10 mL of water cooled to 0° C. was added hydroxylamine sulfate (1.02 g, 6.21 mmole), NaOH (4.75 mL of 6.25 N, 29.9 mmole) and Methyl 4-[(2-{4-{N-[(tert-butyloxy)carbonyl-amino]carbamoyl}-N-[(N-{[3-hydroxy-4-(methoxycarbonyl)phenyl]methyl}carbamoyl)methyl]-butanoylamino}acetylamino) methyl]-2-hydroxybenzoate (2.03 g, 2.95 mmole). The stirred solution was allowed to warm to room temperature and then stirred for approx. 24 hours. The solution was extracted with ethyl acetate and the aqueous phase was adjusted to the pH range 5 to 6 by addition of conc. HCl. A precipitate formed which became oily upon standing. The oily material was washed with water and solidified when dried in vacuo under high vacuum.

$^1$H NMR (300 MHz, DMSO-d$_6$) 1.36 (singlet, 9H, C(CH$_3$)$_3$), 1.70 (pentet, J=7 Hz, 2H, COCH$_2$CH$_2$CH$_2$CO), 2.07 (triplet, J=7 Hz, 2H, COCH$_2$CH$_2$CH$_2$CO), 2.27 (triplet, J=7 Hz, 2H, COCH$_2$CH$_2$CH$_2$CO), 3.97 (singlet, 2H, COCH$_2$N), 4.13 (singlet, 2H, COCH$_2$N), 4.23 (multiplet, 4H, ArCH$_2$N), 6.67 (doublet, J=8 Hz, 2H, ArH), 6.71 (singlet, 2H, ArH), 7.62 (doublet, J=8 Hz, 1H, ArH), 7.70 (doublet, J=8 Hz, 1H, ArH), 8.65 (singlet, 1H, NHNHBOC), 8.71 (triplet, J=6 Hz, 1H, NHCO), 9.15 (triplet, J=6 Hz, 1H, NHCO), 9.53 (singlet, 1H, NHNHBOC), 10.25 (broad singlet, 6H, ArOH, CONHOH).

Example XXI

Preparation of N,N-bis({N-[{4-(N-hydroxycarbamoyl)-3-hydroxyphenyl)-methyl]carbamoyl}methyl)-N'-aminopentane-1,5-diamide The crude N,N-bis-({N-[(4-(N-hydroxycarbamoyl)-3-hydroxyphenyl)methyl]-carbamoyl}methyl)-N'-[(tert-butoxy)carbonylamino]pentane-1,5-diamide from above was suspended in 20 mL of dichloroethane and 10 mL of trifluoroacetic acid was added. The deprotection reaction was stirred for 4 hours at room temperature. Dichloroethane and trifluoroacetic acid were removed in vacuo, and the resulting residue was dissolved in 10 mL of methanol, which was added dropwise to 150 mL of stirred ethyl acetate. A precipitate formed which was collected by filtration, washed with ethyl acetate and then dried in vacuo under a high vacuum. Obtained 1.41 grams (68% yield) of product as a white powder.

$^1$H NMR (300 MHz, DMSO-d$_6$) 1.74 (multiplet, 2H, COCH$_2$CH$_2$CH$_2$CO), 2.21 (multiplet, 4H, COCH$_2$CH$_2$CH$_2$CO), 3.99 (singlet, 2H, COCH$_2$N), 4.16 (singlet, 2H, COCH$_2$N), 4.26 (multiplet, 4H, ArCH$_2$N), 6.67 (doublet, J=8 Hz, 2H, ArH), 6.76 (singlet, 2H, ArH), 7.62 (multiplet, 2H, ArH), 8.73 (triplet, J=6 Hz, 1H, NHCO), 9.18 (triplet, J=6 Hz, 1H, NHCO), 9.40 (broad singlet, 2H, NHNH$_2$), 11.43 (broad singlet, 2H, ArOH), 12.32 (broad singlet, 2H, HONHCO).

Example XXII

Preparation of Methyl 2-Hydroxy-4-[(4-{N-[2-(t 2-[4-(N-{(3-hydroxy-4-(methoxycarbonyl)phenyl]methyl}carbamoyl)butanoylamino]ethyl}dimethylamino)ethyl]-carbamoyl}butanoylamino)methyl]benzoate

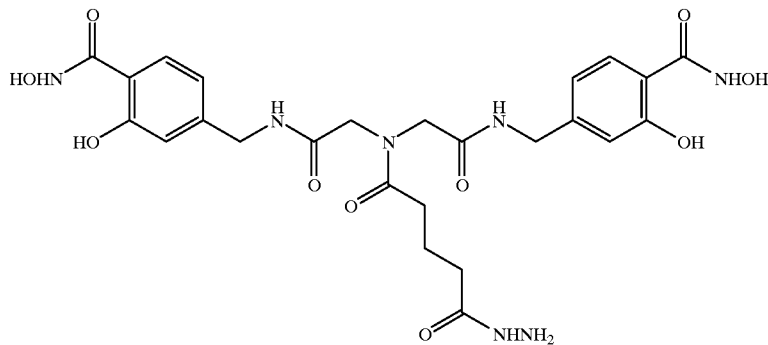

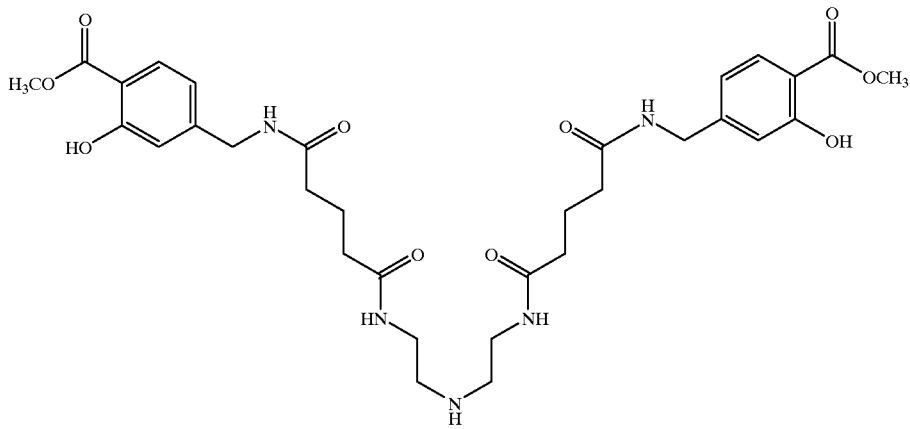

NHS 4-(N-i (3-hydroxy-4-(methoxycarbonyl)phenyl]methyl}carbamoyl)butanoate (6.97 g, 17.8 mmole) was dissolved in 200 mL of tetrahydrofuran (THF) and diethylenetriamine (960 uL, 8.9 mmole) was slowly added. A precipitate formed immediately upon addition of diethylenetriamine. The reaction was stirred for 2 hours at room temperature. Precipitate was collected by filtration, washed with THF and dried overnight in vacuo under high vacuum. Obtained 7.52 grams of crude product as the corresponding N-hydroxysuccinimide salt.

$^1$H NMR (300 MHz, DMSO-$d_6$) 1.70 (multiplet, 4H, COCH$_2$CH$_2$CH$_2$CO), 2.06 (triplet, J=7 Hz, 4H, COCH$_2$CH$_2$CH$_2$CO), 2.14 (triplet, J=7 Hz, 4H, COCH$_2$CH$_2$CH$_2$CO), 2.53 (multiplet, 4H, NHCH$_2$CH$_2$NH$_2$), 2.54 (singlet, 4H, NHS), 3.08 (quartet, J=6 Hz, 4H, NHCH$_2$CH$_2$NH$_2$), 3.86 (singlet, 6H, OCH$_3$), 4.23 (doublet, J=6 Hz, 4H, ArCH$_2$NH), 6.79 (doublet, J=8 Hz, 2H, ArH), 6.81 (singlet, 2H, ArH), 7.70 (doublet, J=8 Hz, 2H, ArH), 7.75 (triplet, J=6 Hz, 2H, CONH), 8.36 (triplet, J=6 Hz, 2H, CONHCH$_2$Ar). $^{13}$C NMR (75 MHz, DMSO-$d_6$) 21.5, 25.2, 34.7, 34.8, 41.7, 48.4, 52.4, 52.5, 111.4, 115.6, 118.3, 130.2, 148.5, 160.4, 169.4, 172.0, 172.2, 173.7.

Example XXIII

Preparation of N-Hydroxysuccinimidyl 5-(N,N-bis-{2-[4-(N-{[3-hydroxy-4-(methoxycarbonyl)phenyl]methyl}carbamoyl)butanoylamino]ethyl}carbamoyl)butanoate

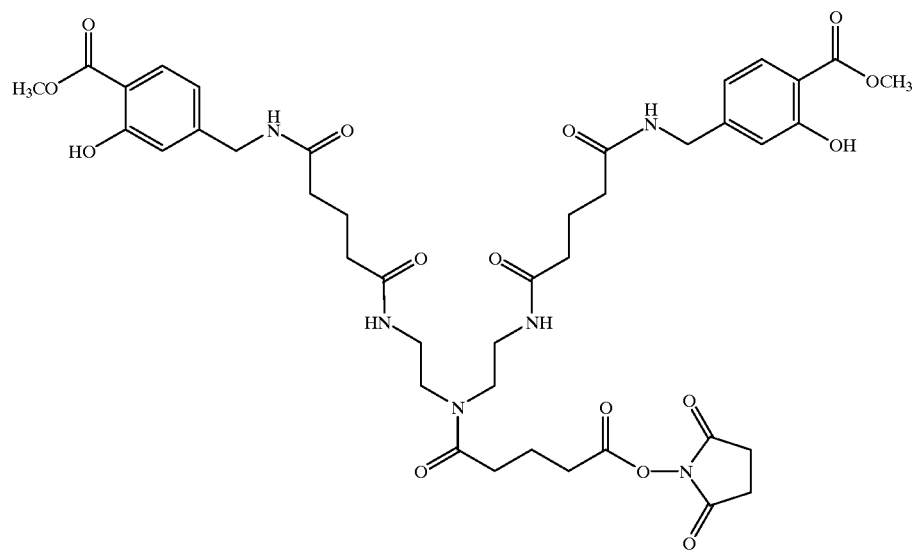

The methyl 2-hydroxy-4-[(4-[N-[2-({2-[4-(N-{(3-hydroxy-4-(methoxycarbonyl)-phenyl]methyl}carbamoyl)butanoylamino]ethyl}dimethylamino)ethyl]carbamoyl)-butanoylamino)methyl]benzoate (850 mg, 1.10 mmole) from above was suspended in 150 mL of N,N-dimethylformamide. Diisopropylethylamine (200 uL, 1.15 mmole) followed by glutaric anhydride (126 mg, 1.10 mmole) were added. The suspension was heated and gently stirred until a solution was obtained. The reaction was stirred for 24 hours at room temperature. The volume of the solution was reduced to approx. 10 mL by rotary evaporation. N-hydroxysuccinimide (135 mg, 1.17 mmole) and 1,3-dicyclohexylcarbodiimide (230 mg, 1.17 mmole) were added and the reaction was stirred for 24 hours at room temperature. Dicyclohexylurea was removed by filtration. While stirring rapidly, 100 mL of diethyl ether was added to the filtrate. The white precipitate that formed was collected by filtration and washed with diethyl ether. The product was dried in vacuo under high vacuum. Obtained 760 mg (79% yield) of product as a white solid.

$^1$H NMR (300 MHz, DMSO-d$_6$) 1.70 (multiplet, 4H, COCH$_2$CH$_2$CH$_2$CO), 1.80 (multiplet, 2H, COCH$_2$CH$_2$CH$_2$CO), 2.06 (triplet, J=7 Hz, 4H, COCH$_2$CH$_2$CH$_2$CO), 2.14 (triplet, J=7 Hz, 4H, COCH$_2$CH$_2$CH$_2$CO), 2.40 (triplet, J=8 Hz, 2H, COCH$_2$CH$_2$CH$_2$CO), 2.68 (triplet, J=8 Hz, 2H, COCH$_2$CH$_2$CH$_2$CO), 2.79 (singlet, 4H, NHS), 3.16 (multiplet, 4H, NHCH$_2$CH$_2$NH$_2$), 3.27 (multiplet, 4H, NHCH$_2$CH$_2$NH$_2$), 3.86 (singlet, 6H, OCH$_3$), 4.23 (doublet, J=6 Hz, 4H, ArCH$_2$NH), 6.78 (doublet, J=8 Hz, 2H, ArH), 6.81 (singlet, 2H, ArH), 7.70 (doublet, J=8 Hz, 2H, ArH), 7.85 (triplet, J=6 Hz, 2H, CONH), 7.96 (triplet, J=6 Hz, 2H, CONH), 8.35 (triplet, J=6 Hz, 2H, CONHCH$_2$Ar), 10.49 (singlet, 2H, ArOH).

Example XXIV

Preparation of Methyl 4-[(4-{N-[2-(4-{N-[(tert-butoxy)carbonylamino]carbamoyl}-N-{2-[4-(N-{[3-hydroxy-4-(methoxycarbonyl)phenyl]methyl}carbamoyl)butanoylamino]-ethyl}butanoylamino)ethyl]carbamoyl}butanoylamino)methyl]-2-hydroxybenzoate Dissolved NHS 5-(N,N-bis-{2-[4-(N-{[3-hydroxy-4-(methoxycarbonyl)phenyl]-methyl}carbamoyl)butanoylamino]ethyl}carbamoyl)butanoate (449 mg, 0.517) in 40 mL of tetrahydrofuran. Had to heat slightly to obtain solution. Let cool to room temperature then added tert-butyl carbazate (70 mg, 0.53 mmoL) and stirred for 16 hours. Quenched reaction mixture with 1 N HCl (5 mL) and diluted with ethyl acetate. Extracted with water and brine. Dried over anhydrous magnesium sulfate, filtered, and removed solvent in vacuo. Collected 380 mg (83%) of crude product.

$^1$H NMR (300 MHz, DMSO-d$_6$) 1.37 (singlet, 9H, C(CH$_3$)$_3$), 1.65–1.76 (multiplet, 6H, COCH$_2$CH$_2$CH$_2$CO), 2.02–2.33 (multiplet, 12H, COCH$_2$CH$_2$CH$_2$CO), 3.15 (multiplet, 4H, NHCH$_2$CH$_2$N), 3.29 (multiplet, 4H, NHCH$_2$CH$_2$N), 3.86 (singlet, 6H, OCH$_3$), 4.23 (doublet, J=6 Hz, 4H, ArCH$_2$NH), 6.78 (doublet, J=8 Hz, 2H, ArH), 6.81 (singlet, 2H, ArH), 7.70 (doublet, J=8 Hz, 2H, ArH), 7.85 (triplet, J=6 Hz, 1H, CONH), 7.96 (triplet, J=6 Hz, 1H, CONH), 8.35 (triplet, J=6 Hz, 2H, CONHCH$_2$Ar), 8.64 (singlet, 1H, BOCNHNH), 9.47 (singlet, 1H, BOCNHNH), 10.49 (singlet, 2H, ArOH).

Example XXV

Preparation of N,N-bis-[2-(4-{N-[(4-(N-hydroxycarbamoyl)-3-hydroxyphenyl)methyl]-carbamoyl}butanoyl amino)ethyl]-N'-[(tert-butoxy)carbonylamino)pentane-1,5-diamide

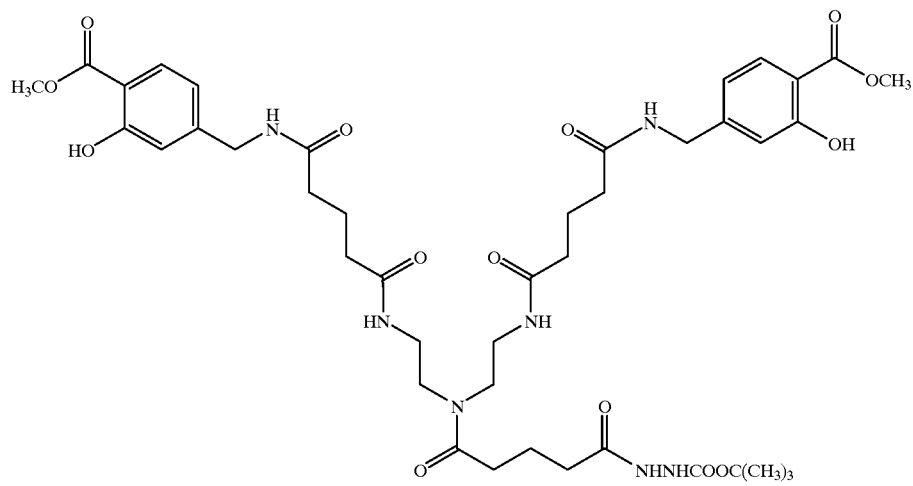

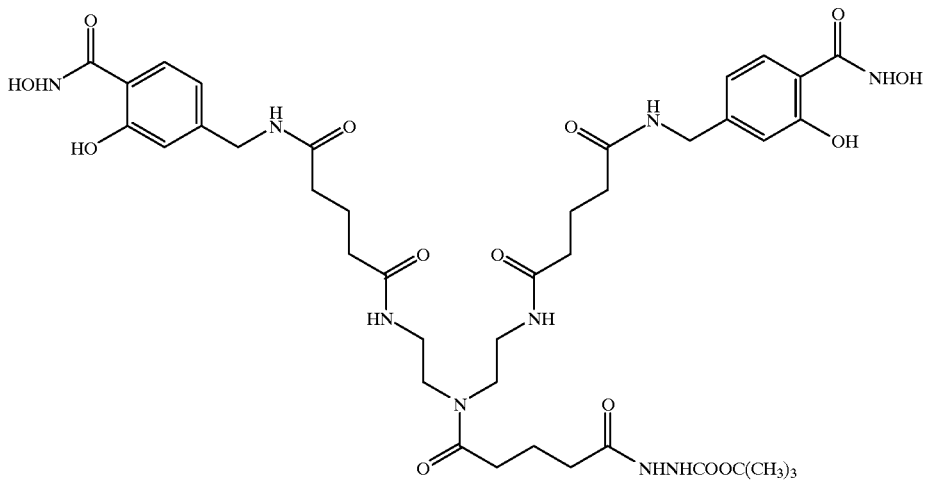

Dissolved hydroxylamine sulfate (365 mg, 2.22 mmoL) in 10 mL of H₂0 and cooled to 0° C. Added 6.25 N NaOH solution (1.80 mL, 11.3 mmoL) followed by methyl 4-[(4-{N-[2-(4-{N-[(tert-butoxy) carbonyl amino] carbamoyl}-N-{2-[4-(N-{[3-hydroxy-4-(methoxycarbonyl)phenyl] ethyl}carbamoyl)butanoylamino]ethyl}butanoylamino)-ethyl]carbamoyl}butanoylamino)-methyl]-2-hydroxybenzoate (980 mg, 1.11 mmoL). Let warm to room temperature and stirred for 16 hours. Filtered away solids. Cooled to 0° C. and added conc. HCl dropwise until a pH of approx. 6 to 7. A precipitate formed initially but oiled out after stirring for 20 minutes. Decanted off water, washed with water, then dried in vacuo under a high vacuum.

¹H NMR (300 MHz, DMSO-d₆) 1.37 (singlet, 9H, C(CH₃)₃), 1.65–1.78 (multiplet, 6H, COCH₂CH₂CH₂CO), 2.02–2.18 (multiplet, 10H, COCH₂CH₂CH₂CO), 2.25–2.33 (multiplet, 2H, COCH₂CH₂CH₂CO), 3.13 (multiplet, 4H, NHCH₂CH₂N), 3.27 (multiplet, 4H, NHCH₂CH₂N), 4.19 (doublet, J=6 Hz, 4H, ArCH₂NH), 6.72 (doublet, J=8 Hz, 2H, ArH), 6.74 (singlet, 2H, ArH), 7.61 (doublet, J=8 Hz, 2H, ArH), 7.88 (triplet, J=6 Hz, 1H, CONH), 7.97 (triplet, J=6 Hz, 1H, CONH), 8.25 (triplet, J=6 Hz, 2H, CONHCH₂Ar), 8.64 (singlet, 1H, BOCNHNH), 9.47 (singlet, 1H, BOCNHNH).

Example XXVI

Praparation of N'-[(4-(N-hydroxycarbamoyl)-3-hydroxyphenyl)methyl]-N-(2-{N-[2-(4-{N-[(N-hydroxycarbamoyl)-3-hydroxyphenyl)methyl] carbamoyl}butanoylamino)ethyl]-4-(N-aminocarbamoyl)butanoylamino}ethyl)pentane-1,5-diamide

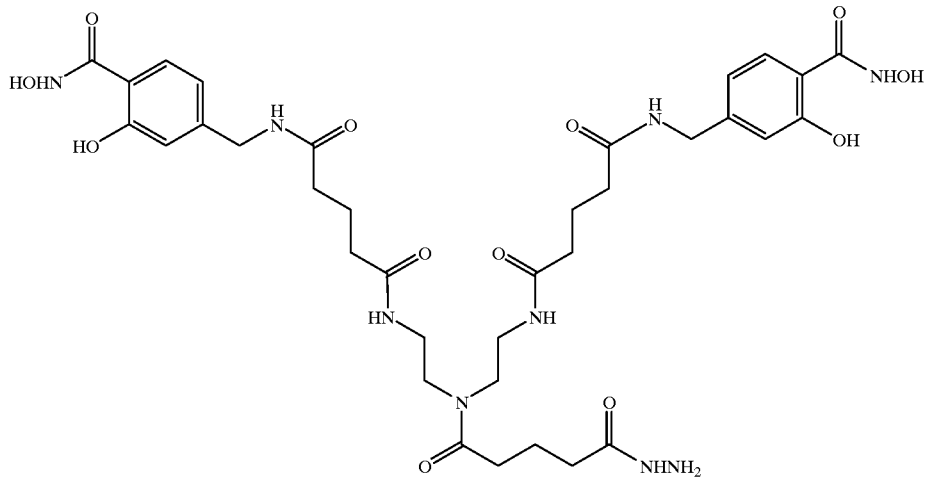

Suspended the crude N,N-bis-[2-(4-{N-[(4-(N-hydroxycarbamoyl)-3-hydroxyphenyl)methyl] carbamoyl}butanoylamino)ethyl]-N'-[(tert-butoxy) carbonylamino)-pentane-1,5-diamide in 10 mL of dichloroethane and added 2 mL of trifluoroacetic acid (material goes into solution after addition of acid). Stirred at room temperature for 3.5 hours. Removed dichloroethane and trifluoroacetic acid in vacuo. Triturated the oil with ethyl acetate, filtered and washed solid with ethyl acetate. Dried in vauco and collected 590 mg (56% yield for 2 steps) of product.

¹H NMR (300 MHz, DMSO-d₆) 1.65–1.78 (multiplet, 6H, COCH₂CH₂CH₂CO), 2.02–2.18 (multiplet, 8H, COCH₂CH₂CH₂CO), 2.21 (multiplet, 2H, COCH$_2$CH$_2$CH$_2$CO), 2.31 (multiplet, 2H, COCH$_2$CH$_2$CH$_2$CO), 3.13 (multiplet, 4H, NHCH$_2$CH$_2$N), 3.27 (multiplet, 4H, NHCH$_2$CH$_2$N), 4.21 (doublet, J=6 Hz, 4H, ArCH$_2$NH), 6.72 (doublet, J=8 Hz, 2H, ArH), 6.74 (singlet, 2H, ArH), 7.61 (doublet, J=8 Hz, 2H, ArH), 7.88 (triplet, J=6 Hz, 1H, CONH), 8.02 (triplet, J=6 Hz, 1H, CONH), 8.36 (triplet, J=6 Hz, 2H, CONHCH$_2$Ar), 9.25 (broad singlet, 2H), 11.38 (singlet, 2H), 12.28 (broad singlet, 2H).

Preparation of Conjugates of General Formulas III and VII and Bioconjugates of General Formulas V and VIII

Example XXVII

Synthesis of 5'-PDBA-labeled Oligodeoxyribonucleotide Conjugates

Oligodeoxyribonucleotide 7172 (sequence 5'-GATTACGCCAGTTGTACGGAC-3') was synthesized on a 1 μmole scale using standard automated phosphoramidite chemistry (Beckman Instruments Oligo 1000 and associated reagents). A protected amine-containing phosphoramidite (Aminolink 2, Applied Biosystems or UniLink Amino Modifier, Clontech) was employed on the same instrument to introduce one to four, reactive primary amines onto the 5'-end of the oligodeoxyribonucleotide using standard chemistry. The completed oligodeoxyribonucleotide was then cleaved from the support and the nucleobases deprotected using an UltraFast Deprotection kit (Beckman Instruments) and the protocol supplied by the manufacturer.

The amino-oligonucleotides were purified by ethanol precipitation, dissolved in 0.8 mL of 0.1 M NaHCO$_3$, and condensed with of succinimidyl 1-carboxamidohexanoyl-3,5-diborylbenzene 1,3-propanediol diester (PDBA-X-NHS) (5 mgs per mmole of primary amino groups on the amino-oligonucleotide in 0.2 ML of anhydrous N,N-dimethylformamide) for 2–18 hours at room temperature.

The crude PDBA-modified oligonucleotide was isolated from the reaction mixture by gel filtration on a KwikSep Dextran column (Pierce Chemical) in 0.1 M aqueous triethylammonium acetate, pH 6.5. The PDBA-modified oligonucleotide was then concentrated in a vacuum centrifuge to 1 mL, and purified by reverse phase HPLC on a 4.6 mm×250 mm C18 column, with a triethylammonium acetate-acetonitrile gradient. The desired product peak was collected and evaporated to a small pellet in a vacuum centrifuge, dissolved in 0.5 mL of water, and stored frozen.

Example XXVIII

Preparation of Bifunctional 2-Hydroxybenzohydroxamic Acid (Bifunctional-SHA) Magnetic Beads Ten milliliters of unmodified M280 or M450 magnetic beads (Dynal) were gradually dehydrated into acetonitrile, and converted to aldehyde modified beads using oxalyl chloride activated N,N-dimethylsulfoxide and triethylamine in dichloromethane at −78° C. The resulting aldehyde bearing beads were gradually rehydrated and suspended in 5 mL of 0.1 M sodium acetate pH 5.5. The aldehyde groups were coupled N'-[(4-(N-hydroxycarbamoyl)-3-hydroxy-phenyl)methyl]-N-(2-{N-[2-(4-{N-[(N-hydroxycarbamoyl)-3-hydroxyphenyl)methyl]carbamoyl}-butanoylamino)ethyl]-4-(N-aminocarbamoyl)butanoylamino}ethyl)pentane-1,5-diamide (21Y-SHA-hydrazide) by adding 25 milligrams dissolved in 200 uL N,N-dimethylsulfoxide, and rotating coupling reaction over night at room temperature. The beads were then washed extensively with water and stored in 5 mL of 10% ethanol.

Example XXIX

Preparation of Bifunctional 2-Hydroxybenzohydroxamic Acid Bifunctional-SHA-Sepharose 4B Bifunctional-SHA-Sepharose 4B was prepared by mixing 130 mg cyanomethyl 4-{[2-(3-amino-N-{[N-({4-[(cyanomethyl)oxycarbonyl]-3-hydroxyphenyl}methyl)carbamoyl]methyl}-propanoyl-amino)acetyl amino]methyl}-2-hydroxybenzoate (9Y-SA(OCH$_2$CN)-β-Ala-amine), dissolved in 30 mL 0.2 M NaHCO$_3$, with. 6.5 g HCl washed CNBr activated Sepharose 4B (Pharmacia) overnight at room temperature. After the coupling reaction, the gel was washed with water and suspended in 50 mL 0.5 M NH$_2$OH, pH 9, and rotated at room temperature for two hours. After the conversion reaction, 2 mL 0.5 M Tris, pH 8.5 were added and the gel slurry mixed at room temperature for 1 hour, and washed with water, 0.5 M NaCl, and water again. The resulting Bifunctional-SHA-Sepharose 4B was suspended in 30 mL of 20% ethanol, and stored at 4° C.

Example XXX

Preparation of Bifunctional 2,6-Dihydroxybenzohydroxamic Acid Bifunctional-DHBHA Sepharose 4B Bifunctional-DHBHA-Sepharose 4B was prepared by mixing 200 milligrams of methyl 4-[(2-{6-amino-N-[(N-{[3,5-dihydroxy-4-(methoxycarbonyl)phenyl]methyl}-carbamoyl)methyl]hexanoylamino}acetylamino)methyl]-2,6-dihydroxybenzoate (9Y-DHBA(OCH$_3$)-amine) dissolved in 30 mL 0.2 M NaHCO$_3$, with 5 g HCl washed CNBr activated Sepharose 4B (Pharmacia), overnight at room temperature. After the coupling reaction, the gel was washed with water and suspended in 50 mL 0.1 M NH$_2$OH, pH 9, and rotated at room temperature for two hours. Finally, the gel was washed with water and suspended in 30 mL of 20% ethanol, and stored at 4° C.

Example XXXI

Preparation of a Phenyldiboronic Acid-α-Biotin Antibody Conjugate

One milliliter of anti-Biotin monoclonal IgG$_1$ antibody (6.5 mg/mL in 0.1 M NaHCO$_3$) was conjugated with 440 nmoles of PDBA-X-NHS (7.4 ul of 60 mM PDBA-X-NHS dissolved in N,N-dimethylsulfoxide) for 1 hour at room temperature. Unconjugated PDBA-X-NHS and its hydrolysis products were removed by dialysis. The ultra-violet absorbance spectrum of the resulting conjugate (PDBA-anti-Biotin) exhibited an increase in A$_{260}$ relative to A$_{280}$ consistent with phenyldiboronic acid modification.

Example XXXII

Preparation of a Phenyldiboronic Acid-Alkaline Phosphatase Conjugate

One milliliter of alkaline phosphatase (Sigma, 6 mg/mL) was dialyzed against one liter of 0.1 M NaHCO$_3$, and conjugated with 700 nmoles of PDBA-X-NHS (10 uL of 70 mM stock in N,N-dimethylformamide) for two hours on ice.

Unconjugated PDBA-X-NHS and its hydrolysis products were removed by dialysis in 0.1 M NaHCO$_3$. The ultraviolet absorbance spectrum of the resulting conjugate (PDBA-AP) exhibited an increase in $A_{260}$ relative to $A_{280}$ consistent with phenylboronic acid modification. The conjugate was stored at 4° C.

Example XXXIII

Preparation of a Bifunctional 2,6-Dihydroxybenzohydroxamic Acid Alkaline Phosphatase Conjugate One milliliter of alkaline phosphatase (Sigma, 6 mg/mL) was dialyzed against one liter of 0.1 M NaHCO$_3$, and conjugated with 714 nmoles of N-hydroxysuccinimidyl 4-(N,N-bis{2-[4-(N-{[3,5-dihydroxy-4-(methoxycarbonyl)phenyl]methyl}carbamoyl)butanoylamino]ethyl}carbamoyl)butanoate (21Y-DHBA(OCH$_3$)-NHS) in N,N-dimethylformamide) for two hours on ice. The methyl ester of the conjugate was converted to a hydroxamic acid by adding one milliliter of 2 M NH$_2$OH, pH 10, and incubating the reaction at 4° C. for six days. The NH$_2$OH reaction mixture was then dialyzed against 0.1 M NaHCO$_3$ and stored at 4° C.

Example XXXIV

Preparation of a Bifunctional 2-Hydroxybenzohydroxamic Acid Goat α-Mouse Antibody Conjugate Two milliliters of goat a-mouse antibody (Rockland, 8.8 mg/mL in 0.1 M NaHCO$_3$) were conjugated with 2.35 umoles N-Hydroxysuccinimidyl 5-(N,N-bis-{2-[4-(N-{[3-hydroxy-4-(methoxycarbonyl)phenyl]methyl}carbamoyl)butanoylamino]-ethyl}carbamoyl)butanoate (21Y-SA(OCH$_3$)-NHS) for one hour at room temperature. The methyl ester of the conjugate was converted to a hydroxamic acid by adding two milliliters of 2 M NH$_2$OH, pH 10, adjusting the pH to 10 with 1 N NaOH, and incubating the reaction at room temperature for three days. NH$_2$OH and unconjugated butanoate (21Y-SA(OCH$_3$)-NHS) and its hydrolysis products were removed by gel filtration on a G-25 Sephadex column (Pharmacia) in 0.1 M NaHCO$_3$, and the conjugate (SHA-goat α-mouse) was stored at 40 C.

Example XXXV

Preparation of a Bifunctional 2,6-Dihydroxybenzohydroxamic Acid Goat α-Mouse Antibody Two milliliters of goat α-mouse antibody (Rockland, 8.8 mg/mL in 0.1 M NaHCO$_3$) were conjugated with 2.5 umoles of with (21Y-DHBA(OCH$_3$)-NHS) for 1 hour at room temperature. The methyl ester of the conjugate was converted to a hydroxamic acid by adding two milliliters of 2 M NH$_2$OH, pH 10, adjusting the pH to 10 with 1 N NaOH, and incubating the reaction at room temperature for three days. NH$_2$OH and unconjugated (21Y-DHBA(OCH$_3$)-NHS) and its hydrolysis products were removed by gel filtration on a G-25 Sephadex column (Pharmacia) in 0.1 M NaHCO$_3$, and the conjugate (Bifunctional-DHBHA-goat α-mouse) stored at 4° C.

Example XXXVI

Polymerase Chain Reaction (PCR) Protocol

A region of Lambda DNA (801bp) was amplified by the polymerase chain reaction. The PCR reaction contained 200 uM dATP, dCTP, dGTP, and dTTP in addition to Biotin- and PDBA-modified oligonucelotide primers at 1 uM in 1× X PCR Buffer II (Perkin Elmer), Lambda DNA (1 ng/uL), and 1 U of *Thermus aquaticus* DNA polymerase. The reaction mixture was denatured at 92° C. for one minute and amplified by 35 cycles of PCR at 95° C. for 10 seconds, 620 C for 20 seconds, and 720 C for 30 seconds, with a final extension at 72° C. for 5 minutes. The reaction produced 50–100 ng of amplified product (801 bp), which exhibited retarded mobility relative to unmodified PCR product during electrophoresis on 1% agarose gels in 50 mM Tris, 100 mM borate, 2 mM EDTA, pH 8.3.

Example XXXVII

Sandwich Hybridization Detection of Nucleic Acid Probes on Magnetic Particles

A 42-mer oligonucleotide was hybridized with two 21-mer oligonucleotides bearing 5'-PDBA and Biotin labels in 1.5 M NaCl, 150 mM sodium citrate, pH 7, at 45° C. for ten minutes. Twenty-five microliters of the hybridization mixture was mixed with twentyfive microliters of M280 streptavidin-magnetic particles (Dynal) in a polypropylene multiwell plate well. After 30 minutes, the magnetic particles were captured in the bottom of the well with a magnetic plate, and washed five times with 150 mM NaCl, 20 mM Tris-HCl, 0.02% Tween 20, pH 8.

One hundred microliters of Bifunctional-DHBHA-AP (1 ug/mL in 1 mg/mL BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween 20, pH 8. Alkaline phosphatse substrate (1 mg/mL p-nitrophenylphosphate in 1 M diethanolamine buffer, 1 mM MgCl$_2$, 0.1 mM ZnCl$_2$, pH 10.4) was added, and incubated at 37° C. for 90 minutes. The Absorbance at 405 nm ($A_{405}$) was measured with an ELISA plate reader (Molecular Devices).

A strong A405 was produced when all components of the hybridization sandwich were present, and the signal was proportional to the amount of 42-mer present. Experimental controls lacking either the 42-mer, the Biotin-oligonucleotides and PDBA-oligonucleotides did not produce a significant $A_{405}$.

Example XXXVIII

Sandwich Hybridization Detection of Nucleic Acid Probes in Multiwell Plates

The wells of a polystyrene multiwell plate (Becton Dickinson) were coated with Bifunctional-DHBHA by filling the wells with 200 uL of Bifunctional-DHBHA-goat α-mouse conjugate (30 ug/mL in 0.1 M NaHCO$_3$ pH 9.0) and incubating overnight at 4° C. The coating solution was removed and the plate backcoated with 5 mg/mL BSA (300 ul per well in 0.2 M NaHCO$_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0).

One hundred microliters of unpurified PDBA and biotin labeled PCR product were added to 900 ul of 1.5N NaCl, 150 mM sodium citrate, pH 7.0 (10× SSC) and serially-diluted in 10× SSC. One hundred microliters of the diluted PCR products were added to the wells and incubated for one hour at room temperature. The plate was then washed five times with ELISA Wash Buffer, and 100 ul of Streptavidin-Alkaline Phosphatase (Boehringer Mannheim, 0.2 U/mL in 1 mg/ml BSA, 140 mM NaCl, 10 mM Tris-HCl, pH 8.0) were added to each well and incubated for thirty minutes at room temperature.

The plate was washed 5 times with ELISA Wash Buffer, and 200 ul of p-nitrophenyl-phosphate (1 mg/mL in diethanolamine, 1 mM $MgCl_2$, 0.1 mM $ZnCl_2$, pH 10.4) were added to the plate and incubated at 37° C. for 30–60 minutes. Less than 1 uL of PCR product was detected. PCR product lacking either PDBA or biotin labels was not detected.

Example XXXIX

Detection of PDBA- & Biotin-Labeled PCR Product on Bifunctional-SHA-Magnetic Beads PDBA- and biotin-labeled PCR product (0.02 $\mu$L–5 $\mu$L) was diluted into 25–100 $\mu$L of 1.5 M NaCl, 150 mM sodium citrate, pH 7 (10× SSC), and added to a polypropylene multiwell plate well containing Bifunctional-SHA-magnetic particles (10–50 ul). The particles and PCR product were mixed occasionally for 30–60 minutes at room temperature. The magnetic particles were captured in the bottom of the wells with a magnetic plate and washed five times in 150 mM NaCl, 20 mM Tris-HCl, 0.02% Tween 20, pH 8 (ELISA Wash Buffer). One hundred microliters of streptavidin alkaline-phosphatase (Boehringher Mannheim, 0.2 U/mL in 1 mg/mL BSA, NaCl, Tris-HCl, pH 8) were added and mixed with the magnetic particles for 30 minutes at room temperature. The magnetic particles were captured in the bottom of the wells with a magnetic plate and washed 5 times with ELISA Wash. Alkaline phosphatase substrate was added (1 mg/ml p-nitrophenyl phosphate in 1 M diethanolamine buffer, 1 mM $MgCl_2$, 0.1 mM $ZnCl_2$, pH 10.4), and the color developed at 37° C. for 10–60 minutes. The lower limit of detection was 50 pg of PCR product.

Example XXXX

Detection of a PDBA-Labeled Oligonucleotide Hybridized to a Biotin-Labeled Oligonucleotide A 42-mer oligonucleotide was hybridized with two 21-mer oligonucleotides bearing 5'-PDBA and Biotin labels in 1.5 M NaCl, 150 mM sodium citrate, pH 7, at 45 C for ten minutes. Twenty-five microliters of the hybridization mixture was mixed with 1–50 uL of Bifunctional-SHA-magnetic particles (Dynal, M450) in a polypropylene multiwell plate well. After 30 minutes, the magnetic particles were captured in the bottom of the well with a magnetic plate, and washed five times with 150 mM NaCl, 20 mM Tris-HCl, 0.02% Tween 20, pH 8.

One hundred microliters of streptavidin-alkalive phosphatase conjugate (SA-AP) (1 ug/mL in 1 mg/mL BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween 20, pH 8. The particles were mixed with alkaline phosphatse substrate (1 mg/mL p-nitrophenyl phosphate in 1 M diethanolamine buffer, 1 mM $MgCl_2$, 0.1 mM $ZnCl_2$, pH 10.4) and incubated at 37° C. for 90 minutes. The A405 was measured with a ELISA plate reader (Molecular Devices). As little as 45 pg of oligonucleotide 42-mer was detected. Experimental controls lacking either the 42-mer, or the PDBA or Biotin labeled oligonucleotides did not produce a significant $A_{405}$.

Example XXXXI

Immobilization of a PDBA-anti-Biotin Conjugate on Bifunctional-SHA-Sepharose 4B

One mg of PDBA-anti-Biotin, diluted to 1 mL with Tris buffered saline, was applied to small column of Bifunctional-SHA-Sepharose 4B (1.0×2.0 cm), and washed extensively with Tris buffered saline. The size of the $A_{280}$ peak of the material not binding to the column indicated that almost all of the PDBA-conjugate was immobilized on the column.

Biotin binding activity of the column was assayed by applying to the column 5 mL of 1 ug/mL biotinylated alkaline phosphatase in Tris buffered saline containing 5 mg/mL bovine serum albumin (BSA). A sample of the peak of the material flowing through the column was collected for comparison of the enzymatic activity with a sample of the alkaline phosphatase dilution applied to column. After applying the sample, the column was washed with 20 mL of buffer. After washing, a very small sample of column material (25 uL liquid containing about 1 uL gel) was collected to measure the enzymatic activity bound to the gel as a result of capture by the immobilized anti-biotin antibody.

The alkaline phosphatase activity was measured by incubating 25 uL of the enzyme samples in 250 uL of 1 mg/mL p-nitrophenylphosphate in 1 M diethanolamine buffer, 1 mM $MgCl_2$, and 0.1 mM $ZnCl_2$, pH 10.4, for 20 minutes and then adding 650 uL of 0.1 M $NaHCO_3$, 10 mM EDTA. Relative to a buffer blank, the $A_{405}$ of the sample applied to the column was 1.57, while the $A_{405}$ of the peak of the material not retained by the column was only 0.042, indicating that virtually all the enzyme conjugate was captured by the column. The small amount of gel assayed produced an $A_{405}$ of 1.30, demonstrating that the enzyme was in fact captured by the column.

Example XXXXII

Immobilization of a PDBA-Alkaline Phosphatase Conjugate on Bifunctional-SHA-Magnetic Beads PDBA-conjugated alkaline phosphatase was diluted to 5 ug/mL in Tris buffered saline containing 5 mg/mL bovine serum albumin. Two hundred microliters of diluted PDBA-conjugated enzyme were mixed with 5, 10, or 20 uL of Bifunctional-SHA-magnetic beads (Dynal, M280). The enzyme was also mixed with 40 uL of unmodified beads as a control. The beads were mixed gently for 10 minutes on ice, after which the beads were captured with a rare earth magnet and washed 4 times with Tris buffered saline. The beads were then suspended in 250 uL of 1 mg/mL p-nitrophenylphosphate in 1 M diethanolamine buffer, 1 mM $MgCl_2$, and 0.1 mM $ZnCl_2$, pH 10.4, and mixed occasionally at 37° C. for 10 minutes. The reactions were terminated with 750 uL of Tris buffered saline, 5 mM EDTA. The $A_{405}$ relative to a buffer blank was measured to determine the alkaline phosphatase activity bound to the magnetic beads. The control beads produced an $A_{405}$ of only 0.15, while the Bifunctional-SHA-magnetic beads produced an $A_{405}$ of 0.62, 0.97, and 1.33 for 5, 10, and 20 uL of beads, respectively, indicating the immobilization of significant amounts of PDBA-AP conjugate on the surface of the beads.

Example XXXXIII

Capture of a PDBA-Labeled PCR product Hybridized to a Biotin-Labeled Oligonucleotide The wells of an amine-coated polystyrene multiwell plate (Coming Costar) were modified with Bifunctional-SHA.

The plate was backcoated with 5 mg/mL bovine serum albumin (BSA) (300 ul per well in 0.2 M NaHCO$_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0).

PDBA-labeled PCR product (2 μL to 10 μL) was serially diluted into 200 μL of 1.5 M NaCl, 150 mM sodium citrate, pH 7 (10× SSC), 0.05% Tween 20. One-hundred microliter aliquots of the diluted reactions were added to the multiwell plate. The PDBA-labeled PCR product was hybridized with a 5'-biotin labeled 21-mer oligonucleotide for 45 minutes at 50° C. The plate was then washed five times with ELISA Wash Buffer, and 100 ul of Streptavidin-Alkaline Phosphatase (Boehringer Mannheim, 0.2 U/mL in 1 mg/ml BSA, 140 mM NaCl, 10 mM Tris-HCl, pH 8.0) were added to each well and incubated for thirty minutes at room temperature.

The plate was washed 5 times with ELISA Wash Buffer, and 200 ul of p-nitrophenyl-phosphate (1 mg/mL in diethanolamine, 1 mM MgCl$_2$, 0.1 mM ZnCl$_2$, pH 10.4) were added to the plate and incubated at 37° C. for 30–60 minutes. Less than 90 ng of hybridized product was detected. Experimental controls lacking either the Biotin-oligonucleotide or the PDBA-PCR product did not produce a significant A$_{405}$.

Example XXXXIV

Detection of a PDBA-dUTP PCR product Hybridized to a Biotin-Labeled Oligonucleotide PDBA-dUTP labeled PCR product (10 μL) was diluted into 200 μL of 1.5 M NaCl, 150 mM sodium citrate, pH 7 (10× SSC), 0.05% Tween 20 containing 100 ng of a 5'-biotin labeled 21-mer oligonucleotide, and added to a streptavidin plus coated polystyrene multiwell plate. Hybridized for 60 minutes at 50° C., and then washed five times in 150 mM NaCl, 20 mM Tris-HCl, 0.02% Tween 20, pH 8 (ELISA Wash Buffer). One hundred microliters of Bifunctional-SHA-alkaline phosphatase (1 ug/mL in 1 mg/mL BSA, NaCl, Tris-HCl, pH 8) were added and the plate was incubated for 30 minutes at room temperature. Washed the plate 5 times with ELISA Wash. Alkaline phosphatase substrate was added (1 mg/ml p-nitrophenyl phosphate in 1M diethanolamine buffer, 1 mM MgCl$_2$, 0.1 mM ZnCl$_2$, pH 10.4), and the color developed at 37° C. for 10–60 minutes. A strong yellow color developed indicating the detection of significant amounts of immobilized PDBA-dUTP-labeled PCR product. Experimental controls lacking either the incorporated PDBA-dUTP label, or the Biotin-labeled oligonucleotide did not produce a significant A$_{405}$.

Example XXXXV

Comparison of Binding of PDBA-Alkaline Phosphatase, PBA-Alkalinephosphatase and PBA-Oxime on modified Bifunctional-SHA Multiwell Plates The wells of an amine-coated polystyrene multiwell plate (Corning Costar) were modified with Bifunctional-SHA. The plate was backcoated with 5 mg/mL bovine serum albumin (BSA) (300 ul per well in 0.2 M NaHCO$_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0). The plate was blocked by incubating with PBA-oxime (100 ul per well of 10 mM solution in 50 mM Tris, pH 7.5) at room temperature for 30 minutes. The PBA-oxime solution was removed by washing the plate five times with ELISA wash buffer.

PBA- or PDBA-conjugated alkaline phosphatase (100 ul per well of 1 ug/mL in 0.1 M NaHCO$_3$) was added to the multiwell plate and incubated for 30 minutes at room temperature. The plate was then washed five times with ELISA Wash Buffer, and 200 ul of p-nitrophenyl-phosphate (1 mg/mL in diethanolamine, 1 mM MgCl$_2$, 0.1 mM ZnCl$_2$, pH 10.4) were added to the plate and incubated at 37° C. for 30–60 minutes. Lower A$_{405}$ was observed in wells containing PBA-alkaline phosphatase than PDBA-alkaline phosphatase consistent with more PDBA-alkaline phosphatase being bound. Experimental controls containing only 0.1 M NaHCO$_3$ or unconjugated alkaline phosphatase did not produce a significant A405.

What is claimed is:

1. A reagent having the general formula of General Formula I:

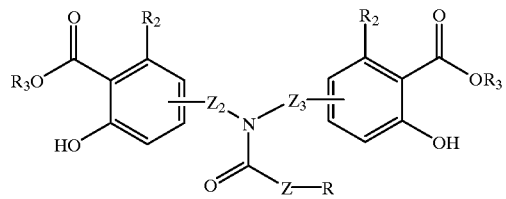

General Formula I wherein group R is an electrophilic or a nucleophilic moiety suitable for reaction of the reagent with a biologically active species;

wherein group R$_2$ is selected from one of H and OH moieties;

wherein group R$_3$ is selected from one of an alkyl and a methylene bearing an electronegative substituent;

wherein group Z is a spacer selected from one of (CH$_2$)$_n$ and CH$_2$O(CH$_2$CH$_2$O)$_{n_2}$, and n is an integer of from 1 to 5, and n$_2$ is an integer of from 1 to 4; and wherein each of group Z$_2$ and Z$_3$ is a spacer selected from one of CH$_2$, CH$_2$CONHCH$_2$, CH$_2$CONH(CH$_2$)$_{n_3}$CONHCH$_2$, and (CH$_2$)$_{n_4}$NHCO(CH$_2$)$_{n_5}$CONHCH$_2$, and n$_3$ is an integer of from 1 to 5, n$_4$ is an integer selected from one of 2 and 3, and n$_5$ is an integer of from 1 to 4.

2. The reagent of claim 1, wherein group R is selected from one of acrylamido, bromo, bromoacetamido, chloro, chloroacetamido, dithiopyridyl, hydrazido, N-hydroxysuccinimido ester, N-hydroxysulfosuccinimido ester, imido ester, imidazolido, iodo, iodoacetamido, maleimido, amino, and thiol moieties.

3. The reagent of claim 1, wherein group R$_3$ is selected from one of CH$_3$, CH$_2$CH$_3$, CH$_2$CN, CH$_2$COOH, CH$_2$CONH$_2$ and CH$_2$OCH$_3$.

4. A conjugate of a biologically active species with a reagent, the conjugate having the general formula of General Formula II:

General Formula II

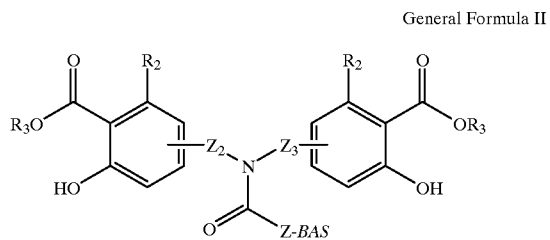

wherein group $R_2$ is selected from one of H and OH moieties;

wherein group $R_3$ is selected from one of an alkyl and a methylene bearing an electronegative substituent;

wherein group Z is a spacer selected from one of $(CH_2)_n$ and $CH_2O(CH_2CH_2O)_{n_2}$, and n is an integer of from 1 to 5, and $n_2$ is an integer of from 1 to 4;

wherein each of group $Z_2$ and group $Z_3$ is a spacer selected from one of $CH_2$, $CH_2CONHCH_2$, $CH_2CONH(CH_2)_{n_3}CONHCH_2$, and $(CH_2)n_4NHCO(CH_2)_{n_5}CONHCH_2$, and $n_3$ is an integer of from 1 to 5, $n_4$ is an integer selected from one of 2 and 3, and $n_5$ is an integer of from 1 to 4; and wherein BAS represents a biologically active species.

5. The conjugate of claim 4, wherein group $R_3$ is selected from one of $CH_3$, $CH_2CH_3$, $CH_2CN$, $CH_2COOH$, $CH_2CONH_2$ and $CH_2OCH_3$.

6. A conjugate having the general formula of General Formula III:

General Formula III

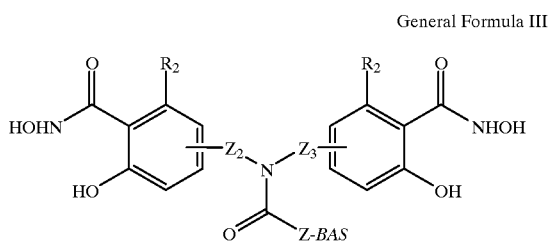

wherein group $R_2$ is selected from one of H and OH moieties;

wherein group Z is a spacer selected from one of $(CH_2)_n$ and $CH_2O(CH_2CH_2O)_{n_2}$, and n is an integer of from 1 to 5, and $n_2$ is an integer of from 1 to 4;

wherein each of group $Z_2$ and $Z_3$ is a spacer selected from one of $CH_2$, $CH_2CONHCH_2$, $CH_2CONH(CH_2)_{n_3}CONHCH_2$, and $(CH_2)_{n_4}NHCO(CH_2)_{n_5}CONHCH_2$, and $n_3$ is an integer of from 1 to 5, $n_4$ is an integer selected from one of 2 and 3, and $n_5$ is an integer of from 1 to 4; and wherein BAS represents a biologically active species.

7. The conjugate of claim 6, wherein group R is selected from one of acrylamido, bromo, bromoacetamido, chloro, chloroacetamido, dithiopyridyl, hydrazido, N-hydroxysuccinimido ester, N-hydroxysulfosuccinimido ester, imido ester, imidazolido, iodo, iodoacetamido, maleimido, amino, and thiol moieties.

8. A reagent having the general formula of General Formula VI:

General Formula VI

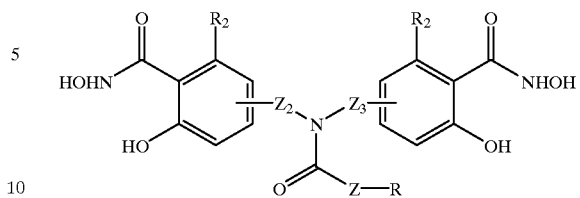

wherein group $R_2$ is selected from one of H and OH moieties wherein group Z is a spacer selected from one of $(CH_2)_n$ and $CH_2O(CH_2CH_2O)n_2$, wherein n is an integer of from 1 to 5, and $n_2$ is an integer of from 1 to 4;

wherein each of group $Z_2$ and group $Z_3$ is a spacer selected from one of $CH_2$, $CH_2CONHCH_2$, $CH_2CONH(CH_2)_{n_3}CONHCH_2$, and $(CH_2)_{n_4}NHCO(CH_2)_{n_5}CONHCH_2$, and $n_3$ is an integer of from 1 to 5, $n_4$ is an integer selected from one of 2 and 3, and $n_5$ is an integer of from 1 to 4; and wherein group $R_1$ is a reactive electrophilic or nucleophilic moiety suitable for reaction with a bioactive species.

9. The reagent of claim 8, wherein group $R_1$ is selected from one of acrylamido, amino, dithiopyridyl, hydrazido, imido ester, maleimido, and thiol moieties.

10. A bioconjugate comprising a bifunctional boronic compound complexing conjugate bonded through a boronic acid complex to at least one boronic compound complexing conjugate, the bioconjugate having the general formula of General Formula V:

General Formula V

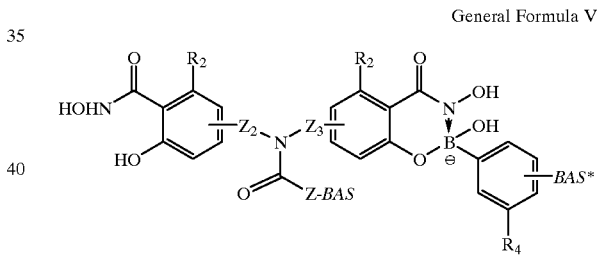

wherein group $R_2$ is selected from one of H and OH moieties;

wherein group $R_4$ is selected from one of H and $B(OH)_2$ moieties;

wherein group Z is a spacer selected from one of $(CH_2)n$;

wherein each of group $Z_2$ and group $Z_3$ is a spacer selected from $CH_2$, $CH_2CONHCH_2$, $CH_2CONH(CH_2)_{n_3}$ $CONHCH_2$, and $(CH_2)_{n_4}NHCO(CH_2)_{n_5}CONHCH_2$, and $n_3$ is an integer of from 1 to 5, $n_4$ is an integer selected from one of 2 and 3, and $n_5$ is an integer of from 1 to 4;

wherein BAS represents a first biologically active species; and wherein BAS* represents a second biologically active.

11. The bioconjugate of claim 10, wherein group BAS and group BAS* are different biologically active species.

12. The bioconjugate of claim 10, wherein the group BAS and the group BAS* are selected from at least one of proteins, peptides, polysaccharides, hormones, nucleic acids, liposomes, cells, drugs, radionuclides, toxins, haptens, inhibitors, fluorophores, ligands, and solid-phase supports.

* * * * *

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

Title page,
Item [56] References Cited, OTHER PUBLICATIONS,
Please insert the following:
-- Wilcheck, M. & Bayer, E.A.;"Introduction to Avidin-Biotin Technology"; Methods in Enzymology; Vol. 184; 1990 (USA).
Kessler et al.;"Non-radioactive Labeling and Detection of Nucleic Acids"; Biol. Chem. Hoppe-Seyler; Vol. 371, pp. 917-27; 1990 USA .
Singhal, R.P. & DeSilva, S.S.M.;"Boronate Affinity Chromatography"; Advances in Chromatography; Vol. 31, pp. 293-335; 1992 (USA).
Mazzeo, J.R. & Krull, I.S.; "Immobilized Boronates for the Isolation and Separation of Bioanalytes"; Biochromatography; Vol. 4, pp. 124-30; 1989.
Bergold, A. & Scouten, W.H.; "Borate Chromatography"; Solid Phase Biochemistry; Ch. 4, pp.149-87; 1983 (USA).
Lorand, J.P. & Edwards, J.O.;"Polyol Complexes and Structure of the Benzeneboronate Ion"; J. Org. Chem.; Vol. 24, p. 769; 1959 (USA).
Bowie, R.A. & Musgrave, O.C.; "Organoboron Compounds. Part V. " The Hydrolysis of Cyclic Phenylboronates"; J. Amer. Chem. Soc.; pp. 3945-49; 1963 (USA).
Sienkiewicz, P.A. & Roberts, D.C.; " pH Dependence of Boronic Acid-Diol Affinity in Aqueous Solution"; J. Inorg. Nucl. Chem.; Vol. 42, pp. 1559-1571; 1980 (USA).
Tanner, D.W. & Bruice, T.C.; "Boric Acid Esters" J. Amer, Chem, Soc.; Vol. 89, pp. 6954-71; 1967 (USA).
Kliegel, W. & Nanninga, D.; "Borchelate von Salicylaldoxim und Derivaten"; Monatshefte Fur Chemie; Vol. 114, pp. 465-84; 1983 (FRG)
Imagawa et al.; "Characteristics and Evaluation of Antibody-Horseradish Perioxidase Conjugates, etc."; J. Applied Biochemistry; Vol. 4, pp.41-57; 1982 (USA)
Kessler, C.; Advances in Mutagenesis Research (Obe, G. ed.); pp. 105-152; Springer-Verlag, Berlin/Heidelberg; 1990 (USA).

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

Brinkley, M.; "A Brief Survey of Methods for Preparing Protein Conjugates with Dyes, Haptens, and Cross Linking Reagents"; Bioconjugate Chem.; Vol. 3, pp. 2-13; 1992 (USA).
Linder et al.; "Technetium Labeling of Monoclonal Antibodies with Functionalized BATOs 1. TcCl (DMG)$_3$PITC"; Bioconjugate Chem.; Vol. 2, pp. 160-170; 1991 (USA).
Linder et al.;"Technetium Labeling of Monoclonal Antibodies with Functionalized BATOs 2. TcCl(DMG)$_3$CPITC Labeling of B72.3, etc." Bioconjugate Chem.; Vol. 2, pp. 407-15; 1991 (USA).
Burnett et al.;"Synthesis of a Fluorscent Boronic Acid Which Reversibly Binds to Cell Walls, etc."; Biochem. Biophys. Research Commun.; Vol. 96, pp. 157-62; 1980 (USA).
Steinberg, G.M. & Swidler, R.; "The Benzohydroxamate Anion"; J. Org. Chem.Vol. ; Vol. 30, pp. 2362-65; 1965 (USA).
Bauer, L & Exner, O., "The Chemistry of Hydroxamic Acids and N-Hydroxyimides"; Angew. Chem. Internat. Edit. ; Vol. 13, pp. 376-84; 1974 (USA).
Cai, S.X. & Kean, J.;"*o* -Acetomidophenylboronate Esters Stabilized Toward Hydrolysis by an Intramolecular O-B Interation, etc."; Bioconjugate Chem.; Vol. 2, pp 317-22; 1991 (USA).
Ramalingam, K. & Nowotnik, D.; "Syntheses of Some Isothiocyanatophenylboronic Acids"; Org. Prep. Proc. Int.; Vol. 23, 729-34; 1991 (USA).
Kliegel, W. & Nanninga, D.; "Borchelate Von Salicyladehydnitronen"; Journal of Organometallic Chem.; Vol. 243, pp 373-85; 1983 (USA).
Ripan et al.; "Etude Du Systeme Acide Borique-Salicylaldoxime en Solutions Aqueuses"; Revue Roumaine de Chimie; Vol. 10, pp. 965-71; 1965 (FRA) .
Roberts et al.; "Pluripotential Amino Acids"; Tetrahedron Letters; Vol. 21, pp. 3435-38; 1980 (USA).
Kemp, D.S. & Roberts, D.;"New Protective Groups for Peptide Synthesis--II The DOBZ Group, etc."; Tetrahedron Letters; Vol. 52, pp. 4629-32; 1975 (USA).

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

Kliegel, W. & Nanninga, D.;"Borchelate von N-substituierten Hydroxamsauren"; Chem. Ber.; Vol. 116, pp. 2616-29; 1983 (FRG).
Mikesova, M. & Bartusek, M.;"Reaction of Boric Acid with Salicylic and Chromotropic Acids and with Their Derivatives"; Chem. Zvesti; Vol. 32(4), pp. 472-77; 1978.
Feeney, R.E., "Chemical Modification of Proteins: Comments and Perspectives"; Int. J. Peptide Protein Res.; Vol. 29, pp. 145-61 (USA), 1987.
Means, G.E. & Feeney, R.E.; "Chemical Modifications of Proteins: History and Applications"; Bioconjugate Chem.; Vol. 1, pp. 2-12 (USA), 1990.
O'Shannessy, D.J. & Quarles, R.H.; "Labeling of the Oligosaccharide Moieties of Immunoglobulins"; J. Immunological Methods; Vol. 99, pp 153-61 (1987) (USA).
van't Reit, B., Wampler, G.L., & Elford, H.L.; "Synthesis of Hydroxy- and Amino- Substitutes Benzohydroxamic Acids, etc.": J. Medicinal Chem.; Vol. 22, No. 5, 589-92, 1979 (USA).
Soundararajan, et al.; "Boronic Acids for Affinity Chromatography: Spectral Methods for Determination, etc."; Analytical Biochem.; Vol. 178, pp. 125-34, 1989 (USA).
Goodchild, J.; "Conjugates of Oligonucleotides and Modified Oligonucleotides: A Review of Their Synthesis and Properties"; Bioconjugate Chem.; Vol. 1, No. 3, pp. 165-93, 1990 (USA).
Kessler, C.; Nonradioactive Labeling and Detection of Biomolecules; Ch. 1-3, 1992 (USA).
Meares, C.F., "Editorial: Introduction to Bioconjugate Chemistry"; Bioconjugate Chem.; Vol. 1, No.1, 1990 (USA).
Waggoner, A.S.; "Fluorescent Probes for Cytometry"; Flow Cytometry and Sorting; 2nd ed; pp. 209-25; 1990 (USA).
Borrebaeck, C.;"Strategy for the production of human monoclonal antibodies using in vitro activated B cells"; J. Immun Methods; Vol. 123; 157-65; 1989 (USA).

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

Chen, et al.; "Structure-Activity Relationships in a Series of 5-[(2,5-Dihydroxybenzyl) amino]salicylate, etc."; Chemical Abstracts; Vol. 120; 322877v; 1994 (USA).
Hirano, et al.; "Silver halide color photographic material"; Chemical Abstracts; Vol. 116; 140012u; 1992 (USA).
Kawasaki, et al.; "Silver halide photographic material with improved storage stability"; Chemical Abstracts; Vol. 109; 160505r; 1988 (USA).
Priewe, H., et al.; "o-Hydroxybenzohydroxamic Acids"; Chemical Abstracts; Vol. 52; 10184; 1958 (USA)
Regnier, G., et al., No. 473-"Acide-Phenols", Bulletin de la Societe Chimique de France 1966, No. 9, pp. 2821-27.
Meindl, W., et al.; "Antimykobakterielle N-Alkylbenzylamine", Arch. Pharm., 315, 941-46 (1982)
Thompson, A.M., et al.; 'Tyrosine kinase Inhibitors: Synthesis of 2,2'-Dithiobis (1H-indole-3-alkanamides) and Investigation of Their Inhibitory Activity Against Epidermal (cont.) Growth Factor Receptor and pp60$^{vsrc}$ Protein Tyrosine Kinases, J. Med. Chem., 1994, 37, 598-609.
Quelet, R., et al., No. 303-"Chloromethylation de l'acide salicylique et des ethers phenoliques correspondants", Bulletin de la Societe Chimique de France, 1969, No. 5, pp. 1698-1705.
Malmberg, H., et al.; "Stereoselectivity in the transfer of the 2-(1-dimethylaminoethyl) phenyl group, R, from LiR$_2$Cu and Li(R)-(2-thienyl)Cu to enones, "Chem Abstracts; Vol.98;71593e;1982.
Bailey et al., Chemical Abstracts, Vol. 111, abstract 130131, 1989.
Ciba Inc., Chemical Abstracts, Vol. 66, abstract 85610, 1967

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

Title page,
Item [57] ABSTRACT, please delete the existing Abstract and insert the following:
--

ABSTRACT OF THE DISCLOSURE

Reagents suitable for the modification of a bioactive species for the purpose of incorporating a bifunctional boronic compound complexing moiety for subsequent conjugation to a different (or the same) bioactive species having pendant phenylboronic acid moieties of General Formula I,

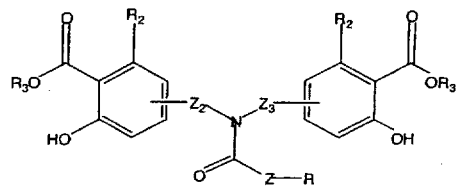

General Formula I wherein group R is an electrophilic or nucleophilic moiety suitable for reaction of the putative bifunctional boronic compound complexing reagent with a bioactive species, wherein group $R_2$ is selected from one of H and OH moieties, and wherein group $R_3$ is selected from one of an alkyl (e.g., methyl, ethyl, etc.) and a methylene bearing an electronegative substituent. Group Z is a spacer selected from $(CH_2)_n$ and $CH_2O(CH_2CH_2O)_{n_2}$, wherein n is an integer of from 1 to 5, and wherein $n_2$ is an integer of from 1 to 4. Each of group $Z_2$ and $Z_3$ is a spacer selected from $CH_2Ar$, $CH_2CONHCH_2Ar$, $CH_2CONH(CH_2)_{n_3}CO\text{-}NHCH_2Ar$, and $(CH_2)_{n_4}NHCO(CH_2)_{n_5}CONHCH_2Ar$, wherein the group Ar represents the aromatic ring in the reagent of General Formula I to which the spacer $Z_2$ or $Z_3$ is appended, wherein $n_3$ is an integer of from 1 to 5, wherein $n_4$ is an integer selected from one of 2 and 3, and wherein $n_5$ is an integer of from 1 to 4. It is to be appreciated that, for a given reagent of General Formula I, spacers $Z_2$ and $Z_3$ need not be the same moiety. Reaction of a reagent of General Formula I with a bioactive species affords a conjugate having pendant putative bifunctional boronic compound complexing moieties (one or more) of General Formula II,

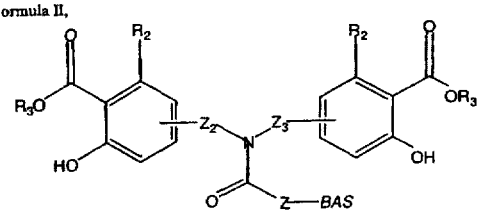

General Formula II

UNITED STATES PATENT AND TRADEMARK OFFICE
CERTIFICATE OF CORRECTION

PATENT NO. : 6,156,884
DATED : December 5, 2000
INVENTOR(S) : Ahlem et al.

It is certified that error appears in the above-identified patent and that said Letters Patent is hereby corrected as shown below:

wherein groups $R_2$, $R_3$, $Z$, $Z_2$ and $Z_3$ are as were previously defined, and wherein the symbol labeled *BAS* represents a biologically active species (or bioactive species) that may or may not contain a portion of a reactive moiety (which may itself have a spacer) used to attach the bioactive species to the reagent. The conjugate of General Formula II may be further reacted with hydroxylamine ($NH_2OH$) by amidation of the benzoic acid ester moiety to afford a class of bifunctional boronic compound complexing conjugate, e.g., conjugate with one or more pendant bifunctional boronic compound complexing moieties of General Formula III,

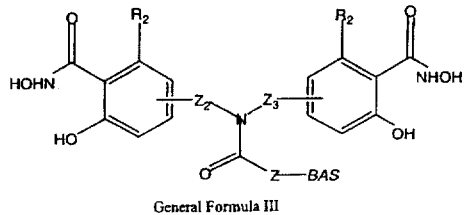

General Formula III wherein groups $R_2$, $Z$, $Z_2$, $Z_3$ and *BAS* are as were previously defined.

Signed and Sealed this

Twenty-sixth Day of March, 2002

Attest:

*Attesting Officer*

JAMES E. ROGAN
*Director of the United States Patent and Trademark Office*